US006958330B1

(12) United States Patent
Audia et al.

(10) Patent No.: US 6,958,330 B1
(45) Date of Patent: Oct. 25, 2005

(54) POLYCYCLIC α-AMINO-ε-CAPROLACTAMS AND RELATED COMPOUNDS

(75) Inventors: James E. Audia, Indianapolis, IN (US); Thomas E. Mabry, Indianapolis, IN (US); Jeffrey A. Nissen, Indianapolis, IN (US); Stacey L. McDaniel, Martinsville, IN (US); Warren J. Porter, Indianapolis, IN (US)

(73) Assignees: Elan Pharmaceuticals, Inc., South San Francisco, CA (US); Eli Lilly and Company, Indianapolis, IN (US)

( * ) Notice: Subject to any disclaimer, the term of this patent is extended or adjusted under 35 U.S.C. 154(b) by 85 days.

(21) Appl. No.: 09/882,777

(22) Filed: Jun. 14, 2001

Related U.S. Application Data

(63) Continuation-in-part of application No. 09/337,408, filed on Jun. 21, 1999, now abandoned.
(60) Provisional application No. 60/160,066, filed on Jun. 22, 1998.

(51) Int. Cl.[7] .................. A61K 31/55; C07D 223/14; C07D 487/00; C07D 491/00; C07D 498/00
(52) U.S. Cl. .................. 514/212.04; 514/212.05; 514/212.06; 514/212.07; 514/212.08; 540/519; 540/520; 540/521; 540/522; 540/523
(58) Field of Search .................. 514/212.04, 212.05, 514/212.06, 212.07, 212.08; 540/519, 520, 521, 522, 523

(56) References Cited

U.S. PATENT DOCUMENTS

| | | | |
|---|---|---|---|
| 2,938,029 A | 5/1960 | Brenner et al. ......... 260/239.3 |
| 3,598,859 A | 8/1971 | Yates et al. | |
| 3,657,341 A | 4/1972 | Thorne | |
| 4,080,449 A | 3/1978 | Croisier et al. | |
| 4,460,579 A | 7/1984 | Karanewsky ............ 424/200 |
| 4,477,464 A | 10/1984 | Slade et al. | |
| 4,666,829 A | 5/1987 | Glenner et al. | |
| 4,977,168 A | 12/1990 | Bernat et al. | |
| 5,238,932 A | 8/1993 | Flynn et al. | |
| 5,283,241 A | 2/1994 | Bochis et al. | |
| 5,284,841 A | 2/1994 | Chu et al. | |
| 5,324,726 A | 6/1994 | Bock et al. | |
| 5,360,802 A | 11/1994 | Chambers et al. | |
| 5,420,271 A | 5/1995 | Warshawsky et al. | |
| 5,478,857 A | 12/1995 | Clemens et al. | |
| 5,556,969 A | 9/1996 | Chambers et al. | |
| 5,618,792 A | * 4/1997 | Gyorkos et al. ............ 514/18 |
| 5,633,251 A | 5/1997 | Claremon et al. | |
| 5,644,055 A | * 7/1997 | De Lombaert ............ 540/522 |
| 5,658,901 A | 8/1997 | Claremon et al. | |
| 5,712,397 A | 1/1998 | Esser et al. | |
| 5,770,573 A | 6/1998 | Arrhenius et al. | |
| 5,968,927 A | * 10/1999 | Karanewsky et al. ....... 514/214 |
| 6,200,969 B1 | * 3/2001 | Fritz et al. ............... 514/214 |

FOREIGN PATENT DOCUMENTS

| | | |
|---|---|---|
| EP | 0 061 187 | 9/1982 |
| EP | 0 167 919 | 1/1986 |
| EP | 0 284 256 | 9/1988 |
| EP | 0 349 949 | 1/1990 |
| EP | 0 376 849 | 7/1990 |
| EP | 0 434 360 | 6/1991 |
| EP | 0 434 364 | 6/1991 |
| EP | 0 434 369 | 6/1991 |
| EP | 0 490 590 | 6/1992 |
| EP | 0 514 133 | 11/1992 |
| EP | 0 523 845 | 1/1993 |
| EP | 0 549 039 | 6/1993 |
| EP | 0591529 | 4/1994 |
| EP | 0 647 632 | 4/1995 |
| EP | 0647632 | 4/1995 |
| EP | 0 652 009 | 8/1995 |
| EP | 0 667 344 | 8/1995 |
| EP | 0 677 517 | 10/1995 |
| EP | 0 732 399 | 9/1996 |
| EP | 810221 A | 3/1997 |
| EP | 0 778 266 | 11/1997 |
| EP | 0945445 | 9/1999 |
| GB | 1 519 495 | 7/1978 |
| GB | 1519495 | 7/1978 |
| GB | 1 573 931 | 8/1980 |
| GB | 2 272 439 | 5/1994 |
| GB | 2 290 788 | 1/1996 |
| HU | 71515 | 12/1995 |
| JP | 5247033 | 9/1993 |
| JP | 06145148 | 5/1994 |
| JP | 04210967 | 8/1994 |
| JP | 6211812 | 8/1994 |
| JP | 07304770 | 11/1995 |
| JP | 10072444 | 3/1998 |
| JP | 179757 | 4/1998 |
| JP | 10101560 | 4/1998 |

(Continued)

OTHER PUBLICATIONS

Aquino, et al. Discovery of 1.5–Benzodiazepines with Peripheral Cholecystokinin (CCK–A) Receptor Agonist Activity. 1. Optimization of the Agonist "Trigger." *J. Med. Chem.* 39: 562–569 (1996).

Bock, et al. "Selective Non–Peptide Ligands for an Accommodating Peptide Receptor. Imidazobenzodiazepines as Potent Cholecystokinin Type B Receptor Antagonists." *Bioorg. and Med. Chem. Lets.* 2(9):987–998 (1994.

(Continued)

*Primary Examiner*—Bruck Kifle
(74) *Attorney, Agent, or Firm*—Burns, Doane, Swecker & Mathis, L.L.P.

(57) ABSTRACT

Disclosed are polycyclic α-amino-ε-caprolactams and related compounds which are useful as synthetic intermediates in the preparation of inhibitors of β-amyloid peptide release and/or its synthesis.

47 Claims, No Drawings

FOREIGN PATENT DOCUMENTS

| WO | 92/01683 | 2/1992 |
|---|---|---|
| WO | WO 92/11246 | 7/1992 |
| WO | WO 92/16524 | 10/1992 |
| WO | 92/16524 | 10/1992 |
| WO | 93/19052 | 9/1993 |
| WO | 93/19063 | 9/1993 |
| WO | WO 94/00438 | 1/1994 |
| WO | 94/04531 | 3/1994 |
| WO | 94/05693 | 3/1994 |
| WO | 94/07486 | 4/1994 |
| WO | 94/10569 | 5/1994 |
| WO | WO 94/25445 | 11/1994 |
| WO | WO 95/03285 | 2/1995 |
| WO | 95/03289 | 2/1995 |
| WO | 95/03290 | 2/1995 |
| WO | 95/09838 | 4/1995 |
| WO | 95/14671 | 6/1995 |
| WO | 95/21840 | 8/1995 |
| WO | 95/23810 | 9/1995 |
| WO | WO 95/25117 | 9/1995 |
| WO | 95/25118 | 9/1995 |
| WO | 95/32191 | 11/1995 |
| WO | 96/05839 | 2/1996 |
| WO | 96/16981 | 6/1996 |
| WO | 96/20725 | 7/1996 |
| WO | 96/22966 | 8/1996 |
| WO | WO 96/25408 | 8/1996 |
| WO | WO 96/29313 | 9/1996 |
| WO | 96/40146 | 12/1996 |
| WO | 96/40653 | 12/1996 |
| WO | 96/40654 | 12/1996 |
| WO | 96/40655 | 12/1996 |
| WO | 96/40656 | 12/1996 |
| WO | WO 97/16410 | 5/1997 |
| WO | 97/30072 | 8/1997 |
| WO | 97/38705 | 10/1997 |
| WO | WO 97/38705 | 10/1997 |
| WO | 98/00405 | 1/1998 |
| WO | WO 98/04539 | 2/1998 |
| WO | WO 98/22430 | 5/1998 |
| WO | WO 98/22433 | 5/1998 |
| WO | WO 98/22494 | 5/1998 |
| WO | WO 98/25911 | 6/1998 |
| WO | 98/25930 | 6/1998 |
| WO | 98/28268 | 7/1998 |
| WO | WO 98/38177 | 9/1998 |
| WO | 98/38177 | 9/1998 |

OTHER PUBLICATIONS

Bock, et al. "Synthesis and Resolution of 3–Amino–1, 3–dihydro–5–phenyl–2H–1,4–benzodiazepin–2–ones." *J. Org. Chem.* 52:3232–3239 (1987).

Bock, et al. "An Expedient Synthesis of 3–Amino–1, 3–Dihydro–5–Phenyl–2H–1,4–Benzodiazepin–2–one." *Tet. Lets.* 28(9): 939–942 (1987).

Chambers, et al. L–708,474: the C5–Cyclohexyl Analogue of L–365,260, A Selective High Affinity Ligand for the CCKB/Gastrin Receptor. *Bioorg. and Med. Chem. Letts.* 3(10):1919–1924 (1993).

Chartier–Harlin, et al. "Early–onset Alzheimer's disease caused by mutations at codon 717 of the β–Amyloid precursor protein gene." *Nature.* 353: 844–846 (1991).

Citron, et al. "Mutation of the β–amyloid precursor protein in familial Alzheimer's disease increases β–amyloid protein production." *Nature* 360:672–674 (1992).

Cordell. "B–Amyloid Formation as a Potential Therapeutic Target for Alzheimer's Disease." *Ann. Rev. Pharmacol. Toxicol.* 34:69–89 (1994).

Evans, et al. "Methods for Drug Discovery: Development of Potent, Selective Orally Effective Cholecystokinin Antagonists," *J. Med. Chem.* 31:2235–2246 (1988).

Evans, et al. "Molecular Mimicry and the Design of Pepidomimetrics." *Molecular Mimicry in Health and Disease.* (A. Lernmark, et al., eds.) Elsevier Science Publishers B.v. (Biomedical Division) (1988) pp. 23–24.

Finizia, et al. "Synthesis and Evaluation of Novel 1,5–Benzodiazepines as potent and selective CCK–B Ligands, Effect of the Substitution of the N–5 Phenyl with Alkyl Groups." *Bioorg. & Medicinal Chemistry Letters.* 6(24):2957–2962 (1996).

Glenner, et al. "Alzheimer's disease: Initial Report of the Purification and Characterization of a Novel Cerebrovascular Amyloid Protein." *Biochem. Biophys. Res. Commun.* 120(3): 885–890 (1984).

Goate, et al. "Segregation of a missense mutation in the amyloid precursor protein gene with familial Alzheimer's disease." *Nature.* 349: 704–706 (1991).

Hirst, et al. "Discovery of 1,5–Benzodiazepines with Peripheral Cholecystokinin (CCK–A) Receptor Agonists Activity (II): Optimization of the C3 Amino Substituent." *J. Med. Chem.* 39: 5236–5245 (1996).

Hofmann, et al. "Interactions of Benzodiazepine Derivatives with Annexins." *J. Biol. Chem.* 273(5):2885–2894 (1998).

Johnson–Wood, et al. "Amyloid precursor protein processing and $A\beta_{42}$ deposition in a transgenic mouse model of Alzheimer's disease." *PNAS USA.* 94: 1550–1555 (1997).

Ksander, G.M., et al. "Dual Angiotensin Converting Enzyme/Thromboxane Synthase Inhibitors." *J. Med. Chem.* 37: 1823–1832 (1994).

Lowe, et al. "A Water Soluble Benzazepine Cholecystokinin–B–Receptor Antagonist." *Bioorg. and Med. Chem. Lets.* 5(17): 1933–1936 (1995).

Lowe, et al. "5–Phenyl–3–ureidobenzzazepin–2–ones as Cholecystokinin–B Receptor Antagonists." *J. Med. Chem.* 37: 3789–3811 (1994).

Mullan, et al. "A pathogenic mutation for probable Alzheimer's disease in the APP gene at the N–terminus of β–amyloid." *Nature Genet.* 1: 345–347 (1992).

Murrell, et al. "A Mutation in the Amyloid Precursor Protein Associate with Hereditary Alzheimer's Disease." *Science.* 254: 97–99 (1991).

Papadopoulos, et al. Anodic Oxidation of N–Acyl and N–Alkoxylcarbonyl Dipeptide Esters as a Key Steop for the Formation of Chiral Heterocyclic Synthetic Building Blocks. *Tetrahedron* 47(4/5):563–572 (1991).

Patel, et al. "Biological Preperties of the Benzodiazepine Amidine Derivative L–740,093, a Choleycystokinin–B/Gastrin Receptor Antagonist with High Affinity in vitro and High Potency in vivo." *Molecular Pharmacology.* 46:943–948 (1994).

Rittle, et al. "A New Amine Resolution Method and its Application to 3–Aminobenzodiazepines." *Tet. Lets.* 28(5):521–522 (1987).

Satoh, et al. "New 1,4–Benzodiazepine–2–one Derivatives as Gastrin/Cholecystokinin–B Antagonists." *Chem. Pharm. Bull.* 43(12): 2159–2167 (1995).

Selkoe, et al. "Amyloid Protein and Alzheimer's Disease." *Scientific American.* 68–78 (1991).

Selkoe, et al. "The Molecular Pathology of Alzheimer's Disease." Neuron. 6:487–498 (1991).

Semple, et al. "Design, Synthesis, and Evolution of a Novel, Selective, and Orally Bioavailable Class of Thrombin Inhibitors: P1–Argininal Derivatives Incorporating P3–P4 Lactam Sulfoamide Moieties." J. Med. Chem. 39: 4531–4536 (1996).

Semple, et al. "A Facile Large Scale Synthesis of Optically Active 3–Amino–5–(2–Pyridyl)–1, 4–Benzodiazepin–2–One Derivatives." Synthetic Communications. 26(4): 721–727 (1996).

Seubert, et al. "Isolation and quanitification of soluble Alzheimer's peptide from biological fluids." Nature. 359: 325–327 (1992).

Sherrill, et al. "An Improved Synthesis and Resolution of 3–Amino–1,3 dihydro–5–phenyl–2H–1, 4–benzodiazepinn–2–ones." J. Org. Chem. 60:730–734 (1995).

Showell, et al. "High Affinity and Potent, Water–Soluble 5–Amino–1,4–Benzodiazepine CCKB/Gastrin Receptor Antagonists Containing a Cationic Solubilizing Group." J. Med. Chem. 37:719–721 (1994).

Smith, et al. "β–APP Processing as a Therapeutic Target for Alzheimer's Disease." Current Pharmaceutical Design. 3:439–445 (1997).

Van Niel, et al. "CCKB Selective Receptor Ligands: Novel 1,3,5–Trisubstituted Benzazepin–2–ones." Bioorganic & Medicinal Chemistry Letters. 5(13):1421–1426 (1995).

Varnavas, et al. "Synthesis of New Benzodiazepine Derivatives as Potential Cholecystokinin Antagonists." Il Farmaco. 46(2):391–401 (1991).

Akhatar, et al., "Bicyclic Imides with Bridgehead Nitrogen.", J. Org. Chem., 55: pp. 5222–5225 (1990).

Armstrong, et al., "An Efficient Asymmetric Synthesis of (R)–3–Amino–2,3,4,5–tetrahydro–1H–[1] benzazepin–2–one", Tetrahedron Letters, 35: pp. 3239–3242 (1994).

Barton, et al., "A New Rearrangement of Ketonic Nitrones . . . ", J. Chem. Soc., pp. 1764–1767 (1975).

Ben–Ishai, et a., "Intra vs Intermolecular Amidoalkylation of Aromatics", Tetrahedron, 43:2, pp. 439–450 (1987).

Blade–Font, "Facile Synthesis of γ–,δ–, and ε–lactams by Cyclodehydration of ω–amino Acids on Alumina or Silica Gel", Tetrahedron Letters, 21: 2443–2446 (1980).

Brown, et al., "A Revision of the Structure of 7–Phenyloxindole", Tetrahedron Letters, 8: pp. 667–670 (1971).

Burkholder, et al., "The Synthesis of 6–Amino–5–Oxo–7–Phenyl–1,4–Oxazepines As Conformationally Constrained Cauche (–) Dipeptide Mimetics", Biog. Med. Chem. Letter, 2: p. 231 (1993).

Busacca, et al., "Synthesis of Novel Tetrahydrobenzazepinones", Tetrahedron Letters, 33:2, pp. 165–168 (1992).

Butcher, et al., "Preparation of 3–Amino–1, 4–Benzodiazepin–2–Ones Via Direct Azidation with Trisyl Azide", Tetrahedron Letters, 37:37, pp. 6685–6688 (1996).

Chartier–Harlin, et al., "Early–onset Alzheimer's disease caused by mutations at codon 717 of the β–Amyloid precursor protein gene.", Nature. 353:31, pp. 844–846 (1991).

Citron, et al., "Mutation of the β–amyloid precursor protein in familial Alzheimer's disease increases β–amyloid protein production.", Nature 360:672–674 (1992).

Clark, et al., "Effects of Remote N–(ters–Butoxycarbonyl) Groups on Heteroatom Directed Lithiation at Benzylic Positions", Tetrahedron, 49:7, pp. 1351–1356 (1993).

Colombo, et al., "Synthesis of 7,5–Fused Bicyclic Lactams by Steroselective Radical Cyclization", Tetrahedron Letters, 35:23, pp. 4031–4034 (1994).

Cornille, et al., "Electrochemical Cyclization of Dipeptides Toward Novel Cicyclic, Reverse–Turn Pepidomimetics", J. Am. Chem. Soc., 117: pp. 909–917 (1995).

Crombie, et al., "Transamidation Reactions of β–Lactams", Tetrahedron Letters, 27:42, pp. 5151–5154 (1986).

Curran, et al., "A Short synthesis of Bicyclic Dipeptides Corresponding to Xxx–L–Pro and Xxx–D–Pro Having Constrained Cis–Proline Amides", Tetrahedron Letters, 36, pp. 191–194 (1995).

Das, et al., "Dual Metalloprotease Inhibitors IV", Biorg. Med. Chem. Lett., 4:18, pp. 2193–2198 (1994).

Desai, et al., "Polymer Bound EDC (P–EDC): A convenient Reagent for Formation of An Amide", Tetrahedron Letters, 34:48, pp. 7685–7688 (1993).

Dickerman, et al., "Studies in Piperdidone Chemisty", J. Org. Chem., 14, p. 530–536 (1949).

Dickerman, et al., "The Schmidt6 Reaction with 2,2,6–Trimethyl–And 1,3–Dimethyl–4–Piperidones", J. Org. Chem., 20: p. 206–209 (1955).

Dickerman, et al., "The Schmidt Reaction with 3–Ethoxycarbonyl–4–P Peripdones and the synthesis of six 5–homo–piperazinones", J. Org. Chem., 19, p. 1855–1861 (1954).

Donaruma, et al., Organic Reactions, Ch. 1, "The Beckmann Rearrangement", pp. 1–156 (1960).

Edwards, et al., "Cyclization and Fragmentation of N–Chloro Lactams", Can. J. Chem., 49: pp. 1648–1658 (1971).

Flynn et al., "Applications of a Conformationally Restricted Phe–Leu Dipeptide Mimetic to the Design of a Combined Inhibitor of Angiotensin I–Converting Enzyme and Neutral Endopeptidase 24.11", J. Med. Chem., 36: pp. 2420–2423 (1993).

Freidinger et al., "Protected Lactam–Bridged Dipeptides for Use as Conformational Constrains in Peptides", J. Org. Chem, 47: pp. 104–109 (1982).

Gaetzi, "Fungicidal Amino azacycloheptanones", Chem. Abs., 66: 28690m.

Games, et al., "Alzheimer–type Neuropathology In Transgenic Mice Overexpressing V717F β–amyloid Precursor Protein", Letters to Nature, 373: pp. 523–527 (19950.

Glenner, et al. "Alzheimer's Disease: Initial Report of the Purification and Characterization of a Novel Cerebrovascular Amyloid Protein," Biochem. Biophys. Res. Commun. 120(3): 885–890 (1984).

Goate, et al. "Segregation of a missense mutation in the amyloid precursor protein gene with familial Alzheimer's disease." Letters to Nature. 349: 704–706 (1991).

Gracias, et al., "Efficient Nitrogen Ring–Expansion Process Facilitated by in Situ Hemiketal Formation", J. Am. Chem. Soc., 117: pp. 8047–8048 (1995).

Grunewald, et al., "Effect of Ring Size or an Additional Heteroatom on the Optency and Selectivity of Bicyclic Benzylamine–Type Inhibitors of Phenylethanolamine N–Methyltransferase", J. Med. Chem., 39, pp. 3539 (1996).

Hansen, et al., "Re–examination and further Development of a Precise and Rapid Dye Method for Measuring Cell Growth", J. Immun. Meth., 119: pp. 203–210 (1989).

Hart, et al., "The Ester Enolate–Imine Condensation Route to β–Lactams", Chem. Rev., 89: pp. 1447–1465 (1989).

Herschmann, "Recherches sur la nature du Methonitrile de Wallach", *Helv. Chim. Acta*, 7:329, p. 2537–2547 (1949).

Hoffman, et al., "Efficient Synthesis of N–Substituted Lactams from (N–Arylsulfonyloxy) Amines and Cyclic Ketones", *Tetrahedron Letters*, 30: pp. 4207–4210 (1989).

Hoffman, et al., "Synthesis and Structure of 7–Methyl–and 7–Pheynl–1,2,3,4–Tetrahydro–1,4–Diazepin–5–ones",*Tetrahydrodiazepinones.*, 27: p. 3565 (1962).

Holladay, et al., "Synthesis of α–Benzyl γ–Lactam, α–Benzyl δ–Lactam and α–Benzylproline Derivatives as Conformationally Restricted Analogues of Phenylalaninamide", *J. Org. Chem.*, 56: 3900–3905 (1991).

Hu, et al., "Two Efficient Syntheses of (+)–anti–N–Benzyl–3–Amino–4– Hydroxyhexahydroazepine", *Tetrahedron Letters*, 36:21, pp. 3659–3662 (1995).

Itoh, K., "Synthesis and Antiotensin Converting Enzyme–Inhibitory Activity of 1,5–benzothiazeine . . . ", *Chemical Abstracts*, vol. 111, No. 15, Oct. 9, 1989, Columbus, OH, Astract No. 126464h.

Kawase, et al., "Electrophilic Aromatic Substituion with N–Methoxy–N–Acylnitrenium Ions Generated from N–Chloro–N–Methoxyamies", *J. Org. Chem.*, 54: pp. 3394–3403 (1989).

King, et al., "Iodotrimthylsilane–Mediated 2–Mononhalogenation of 4–aza–5α–androstan–3–one Steriods", *J. Org. Chem.* 58: pp. 3384 (1993).

Kitagawa, et al., "Structural Aanlysis of β–Turn Mimics Containing a Substituted 6–Aminocaproic Acid Linker", *J. Am. Chem. Soc.*, 117: pp. 5169–5178.

Klolc, "Amino Acids and Peptides LXXXIX Synthesis of L–4–Azalysine, D–4–Azalsine, and L–4–Azalsine0 [6–14C]" *Coll. Czech. Chem. Comm.*, 34, pp. 630 (1969).

Kametani, et al., "A Simple Synthesis of 4–Thiazolidones, Tetrahydro–1,3–Thiazin–4–One and Hexahydro–1, 3–Thiazepin–4–Ones from Amide–Thiols", *Hetercyclces*, 9: pp. 831–840 (1978).

Krimm, "Uber Isonitron", *Chem. Ber.*, 91: p. 1057 (1958).

Krow, et al., "Regioselective Functionalization", *J. Org. Chem.*, 61: pp. 5574–5580 (1996).

Ksander, G.M., et al. "Dual Angiotensin Converting Enzyme/Thromboxane Synthase Inhibitors.",*J. Med. Chem.* 37: 1823–1832 (1994).

Kukolja, et al., "Orally Absorbable Cephalosporin Antibiotics", *J. Med. Chem.*, 28:12, pp. 1886 (1985).

Losse, G., et al., "Synthese Des Depsipeptides Valinomycin", *Tetrahedron*, 27, pp. 1423–1434 (1971).

Lowe, et al., "5,7–Diphenyl–3–Ureidohexahydroazepin–2–Ones as Cholecystokinin–B Receptor Ligands", *Bioorg & Med Chem Letters*, 4:24, pp. 2877–2882 (1994).

McKennis, et al., "The Synthesis of Hydroxycotinine and Studies on Its Structure", *Synthesis and Hydroxycotinine*, pp. 383–387 (1963).

Micouin, et al., "Asymmetric Synthesis", *Tetrahedron*, 52:22, pp. 7719–7726 (1996).

Miller, et al., "Application of Ring–Closing Methathesis to the Synthesis of Rigidified Amino Acids and Peptides", *J. Am. Chem. Soc.*, 118, pp. 9606–9614 (1996).

Mullan, et al., "A Pathogenic Mutuation for Probable Alzheimer's Disease in the APP Gene at the N–Terminus of βAmyloid", *Nature Genetics*m 1, pp. 345–347 (1992).

Murrell, et al., "A Mutation in the Amyloid Precursor Protein Associated with Hereditary Alzheimer's Disease", *Reports*, pp. 97–99 (1991).

Nedenskov, et al., "Synthesis of Potential Hypnotics", *Acta. Chem. Scand.*, 12:7, pp. 1404–1410 (1958).

Ogliaruso and wolfe, *Synthesis of Lactones and Lactams*, Patai, et al., Ed., J. Wiley & Sons, NY:NY, (1993).

Orito, et al., "Benzolactams–1", *Tetrahedron*, 36:8, pp. 1017–1021 (1980).

Overberger, et al., "Optically Active Polyamides", *Brooklyn Polytechnic*, pp. 3431–3435 (1963).

Overberger et al., "The Synthesis of Optically Active C–Methyl–2–oxoheptamethyleminines and C–Methyl–7–aminoheptanoic Acids", *Macromolecules*, 1:1, pp. 1–6 (1968).

Parsons, et al., "Benzolactams. A New Class of Converting Enzyme Inhibitors", *Biochem. Biophys. Res. Comm.*, 117: pp. 108–113 (1983).

Pedersen, et al., "Studies on Organophosphorus Compounds", *Tetrahedron*, 35: p. 2433 (1979).

Reupple, et al., "Abberant Alkaloid Biosynthesis", *J. Am. Chem. Soc.*, 93: 7021 et seq. (1971).

Robl, et al., "Synthesis of Benzo–Fused, 7,5–and 7,6–Fused Azepinones and Conformationally Restricted Dipeptide Mimetics", *Tetrahedron Lett.*, 36:10, pp. 1593–1596 (1995).

Robl, et al., "Dual Metalloprotease Ihibitors", *Bioorg. Med. Che. Letter*, 4: pp. 1789–1794 (1994).

Rodriguez, et al., "Conformationally Restricted Analogues of Methionine", *Tetrahedron*, 52: pp. 7727–7736 (1996).

Sekakida, et al., "Studies on Seven–membered Heterocyclic Compounds Containing Nitrogen", *Bull. Chem. Soc. Japan*, 44: pp. 478–480 (1971).

Selkoe, et al. "Amyloid Protein and Alzheimer's Disease." *Scientific American.* 68–78 (1991).

Selkoe, et al. "The Molecular Pathology of Alzheimer's Disease." *Neuron.* 6:487–498 (1991).

Shirota, et al., "Potential Inhibitors of Collagen Biosynthesis", *J. Med. Chem.*, 20: pp. 1623–1627 (1977).

Skiles, et al., "Eleastase Inhibitors Containing Conformationally Restricted Lactams", *Bioorg. Med. Chem. Letter*, 3: pp. 773–778 (1993).

Slusarchyk, et al., "Dual Metalloprotease Inhibitors. V.", *Bioorg. med. Chem. Lett.*, 5: pp. 753–758 (1995).

Smith, et al., "The Curtius Reaction", *Organic Reacitons*, Ch. 9, pp. 337–449 (1946).

Suda, et al., "Metalloporphyrin–catalysed Rearrangement of Oxaziridines", *J. Chem. Soc. Chem. Comm.*, pp. 949–950 (1994).

Thomas, et al, "Nuclear Magnetic Resonance Studies and Conformational Analysis of Bicyclic Inhibitors of Angiotensin–converting Enzyme", *J. Chem. Soc.* Perkin II, 747 (1986).

Ugi, et al., "Ugi Reactions with Trifunctional αAmino Acids, Aldehydes, Isocyanides and Alcohols", *Tetradedron*, 52:35, pp. 11657–11664 (1996).

Van der Steen, et al., "Synthesis of 3–Amino–2–Azetidinones: A Literature Survey", *Tetrahedron Letters*, 47: pp. 7503–7524 (1991).

Vedejs, et al., "Synthesis of N–Methoxy and N–H Aziridines from Alenes", *Tetradedron Letters*, 33: pp. 3261–3264 (1992).

Wada, et al., "Stereospecific and Stereoselective Reactions", *Bull. Chem. Soc. Japan*, 46: pp. 2833–2835 (1973).

Wasserman, et al., "Total Synthesis of (±)–Dihydropheriphylline", *J. Am. Chem. Soc.,* 103, p. 461–462 (1981).

Watthey, et al., "Synthesis and Biological Properties of (Carboxyalkyl)amino–Substituted Bicyclic Lactam Inhibitors of Angiotensin converting Enzyme", *J. Med. Chem.,* 28: pp. 1511–1516 (1985).

Wheeler, et al., "Formation and Photochemical Wolff Rearrangement of Cyclic α–Diazo Ketones", *Organic Syntheses*, Coll. vol. VI, p. 840.

Wolff, "The Schmidt Reaction", *Organic Reactions*, ch. 8, pp. 307–336 (1946).

Yakoo, et al., "Studies on Seven–Membered Heterocyclic Compounds Containing Nitrogen", *Bull. Chem. Soc. Japan*, 29: p. 631 (1956).

Yanganasawa, et al., "Angiotensin–converting Enzyme Inhibitors", *J. Med. Chem.*, 30: p. 1984–1991 (1987).

* cited by examiner

POLYCYCLIC α-AMINO-ε-CAPROLACTAMS AND RELATED COMPOUNDS

CROSS-REFERENCE TO RELATED APPLICATIONS

This application is a Continuation-in-part of U.S. application Ser. No. 09/337,408, filed Jun. 21, 1999, now abandoned, which claims the benefit of U.S. Provisional Application No. 60/160,066, filed Jun. 22, 1998 now abandoned.

BACKGROUND OF THE INVENTION

1. Field of the Invention

This invention relates to polycyclic α-amino-ε-caprolactams and related compounds which are useful as synthetic intermediates in the preparation of inhibitors of β-amyloid peptide release and/or its synthesis.

2. Reference

The following publications, patents and patent applications are cited in this application as superscript numbers:

1. Glenner, et al., *Biochem. Biophys. Res. Commun.* (1984) 120:885–890.
2. U.S. Pat. No. 4,666,829, issued May 19, 1987, to G. G. Glenner et al., entitled "Polypeptide Marker for Alzheimer's Disease and Its Use for Diagnosis."
3. Selkoe, *Neuron.* (1991) 6:487–498.
4. Goate, et al., *Nature* (1990) 349:704–706.
5. Chartier Harlan, et al., *Nature* (1989) 353:844–846.
6. Murrell, et al., *Science* (1991) 254:97–99.
7. Mullan, et al., *Nature Genet.* (1992) 1:345–347.
8. T. W. Greene et al., *Protecting Groups in Organic Synthesis*, Second Edition, Wiley, New York (1991).
9. R. F. C. Brown et al., *Tetrahedron Letters* 1971, 8, 667–670.
10. A. O. King et al., *J. Org. Chem.* 1993, 58, 3384–3386.
11. *Tetrahedron Letters* 1993, 34(48), 7685.
12. U.S. Provisional Application Ser. No. 60/019,790, filed Jun. 14, 1996.
13. U.S. patent application Ser. No. 08/996,442, filed Dec. 19, 1997.
14. R. D. Clark et al., *Tetrahedron* 1993, 49(7), 1351–1356.
15. Schenk, et al., International Patent Application Publication No. WO 94/10569, "*Methods and Compositions for the Detection of Soluble β-Amyloid Peptide*", published 11 May 1994.
16. Citron, et al., *Nature* (1992) 360:672–674.
17. P. Seubert, *Nature* (1992) 359:325–327.
18. Hansen, et al., *J. Immun. Meth.* (1989) 119:203–210.
19. Games et al., *Nature* (1995) 373:523–527.
20. Johnson-Wood et al., *PNAS USA* (1997) 94:1550–1555.

All of the above publications, patents and patent applications are herein incorporated by reference in their entirety to the same extent as if each individual publication, patent or patent application was specifically and individually indicated to be incorporated by reference in its entirety.

3. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine[595]-methionine[596] to asparagine[595]-leucine[596] (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

Compounds which inhibit β-amyloid peptide release and/or its synthesis in vivo are disclosed in U.S. patent application Ser. No. 08/996,422, filed Dec. 22, 1997 entitled "Cycloalkyl, Lactam, Lactone and Related Compounds, Pharmaceutical Compositions Comprising Same, and Methods for Inhibiting β-Amyloid Peptide Release, and/or its Synthesis by Use of Such Compounds," the disclosure of which is incorporated herein by reference in its entirety. The present invention is directed to intermediates useful in the preparation of such compounds.

SUMMARY OF THE INVENTION

This invention is directed to the discovery of a class of intermediates which are useful in the preparation the cycloalkyl, lactam, lactone and related compounds described in U.S. patent application Ser. No. 08/996,422, which compounds inhibit β-amyloid peptide release and/or its synthesis. Accordingly, in one of its composition aspects, this invention is directed to a compound of formula I:

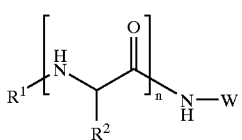

I wherein

W is a substituted ε-caprolactam selected from the group consisting of:

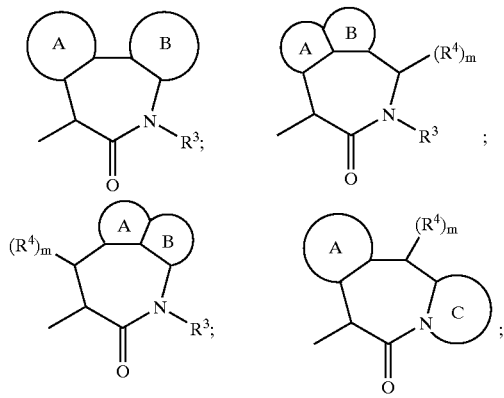

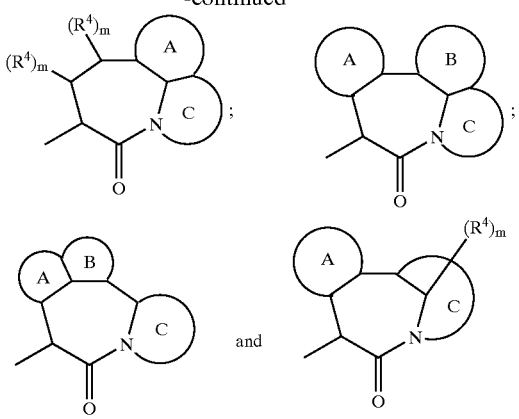

or a substituted 1,5-diazepine of the formula:

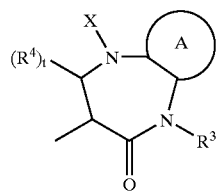

wherein ring A, together with the atoms of the ε-caprolactam or the substituted 1,5-diazepine to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;

ring B, together with the atoms of the ε-caprolactam to which it is attached, forms a carbocyclic or heterocyclic ring selected from the group consisting of aryl, cycloalkyl, substituted cycloalkyl, cycloalkenyl, substituted cycloalkenyl, heteroaryl and heterocyclic;

ring C, together with the atoms of the ε-caprolactam to which it is attached, forms a heteroaryl or heterocyclic ring;

$R^1$ is selected from the group consisting of hydrogen and an amino-blocking group;

$R^2$ is selected from the group consisting of hydrogen, alkyl, substituted alkyl, alkenyl, substituted alkenyl, alkynyl, substituted alkynyl, aryl, cycloalkyl, heteroaryl and heterocyclic;

$R^3$ is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;

each $R^4$ is independently selected from the group consisting of alkyl, substituted alkyl, alkenyl, substituted alkenyl, alkynyl, substituted alkynyl, aryl, cycloalkyl, substituted cycloalkyl, cycloalkenyl, substituted cycloalkenyl, heteroaryl and heterocyclic;

X is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic; or X and one of $R^4$ and the atoms to which they are attached form a double bond;

m is an integer from 0 to 2; n is 0 or 1; t is an integer from 0 to 2; and salts thereof.

Preferably, $R^1$ is hydrogen, tert-butoxycarbonyl (Boc), benzyloxycarbonyl (Cbz), acetyl, 1-(1'-adamantyl)-1- methylethoxycarbonyl (Acm), allyloxycarbonyl (Aloc), benzyloxymethyl (Bom), 2-p-biphenylisopropyloxycarbonyl (Bpoc), tert-butyldimethylsilyl (Bsi), benzoyl (Bz), benzyl (Bn), 9-fluorenyl-methyloxycarbonyl (Fmoc), 4-methylbenzyl, 4-methoxybenzyl, 2-nitrophenylsulfenyl (Nps), 3-nitro-2-pyridinesulfenyl (NPys), trifluoroacetyl (Tfa), 2,4,6-trimethoxybenzyl (Tmob), trityl (Trt), and the like. More preferably, $R^1$ is hydrogen or tert-butoxycarbonyl (Boc).

When n is one, $R^2$ is preferably selected from the group consisting of hydrogen, alkyl, substituted alkyl, alkenyl, cycloalkyl, aryl, heteroaryl and heterocyclic.

Particularly preferred $R^2$ substituents include, by way of example, hydrogen, methyl, ethyl, n-propyl, isopropyl, n-butyl, isobutyl, sec-butyl, tert-butyl, —$CH_2CH(CH_2CH_3)_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —$CH_2$-cyclopropyl, —$CH_2$-cyclohexyl, —$CH_2CH_2$-cyclopropyl, —$CH_2CH_2$-cyclohexyl, —$CH_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2CH_2O$-benzyl, p-$(CH_3)_3COC(O)CH_2O$-benzyl, p-$(HOOCCH_2O)$-benzyl, 2-aminopyrid-6-yl, p-(N-morpholino-$CH_2CH_2O$)-benzyl, —$CH_2CH_2C(O)NH_2$, —$CH_2$-imidazol-4-yl, —$CH_2$-(3-tetrahydrofuranyl), —$CH_2$-thiophen-2-yl, —$CH_2$(1-methyl)cyclopropyl, —$CH_2$-thiophen-3-yl, thiophen-3-yl, thiophen-2-yl, —$CH_2$—$C(O)O$-t-butyl, —$CH_2$—$C(CH_3)_3$, —$CH_2CH(CH_2CH_3)_2$, -2-methylcyclopentyl, -cyclohex-2-enyl, —$CH[CH(CH_3)_2]COOCH_3$, —$CH_2CH_2N(CH_3)_2$, —$CH_2C(CH_3)=CH_2$, —$CH_2CH=CHCH_3$ (cis and trans), —$CH_2OH$, —$CH(OH)CH_3$, —$CH(O$-t-butyl$)CH_3$, —$CH(O$—$CH_2Ph)CH_3$, —$CH_2OCH_3$, —$(CH_2)_4NH$-Boc, —$(CH)4NH_2$, —$CH_2$-pyridyl (e.g., 2-pyridyl, 3-pyridyl and 4-pyridyl), pyridyl (2-pyridyl, 3-pyridyl and 4-pyridyl), —$CH_2$-naphthyl (e.g., 1-naphthyl and 2-naphthyl), —$CH_2$-(4-morpholinyl), p-(4-morpholinyl-$CH_2CH_2O$)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5chlorobenzo[b]thiophen-3-yl, benzo[b]thiophen-5-yl, 6-methoxynaphth-2-yl, —$CH_2CH_2SCH_3$, thien-2-yl, thien-3-yl, and the like.

Preferably, $R^3$ is selected from the group consisting of hydrogen, alkyl, substituted alkyl and cycloalkyl.

Particularly preferred $R^3$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

When present, $R^4$ is preferably alkyl, substituted alkyl or aryl. When W is a substituted 1,5-diazepine, particularly preferred $R^4$ substituents include, by way of example, phenyl and isopropyl.

X is preferably hydrogen, alkyl or aryl; or X and: one of $R^4$ and the atoms to which they are attached preferably form a double bond (i.e., —$C(R^4)=N$—). Particularly preferred X substituents include, by way of example, methyl and phenyl.

Preferably, m is 0 or 1. More preferably, m is 0.

Preferably, t is 0 or 1. In a preferred embodiment, t is 1.

W is preferably a substituted ε-caprolactam selected from the group consisting of:

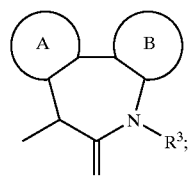
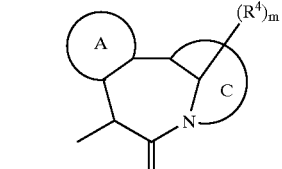
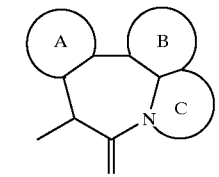
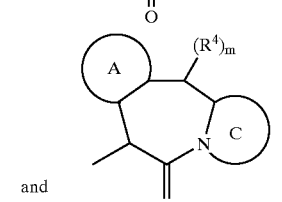

and or a substituted 1,5-diazepine of the formula:

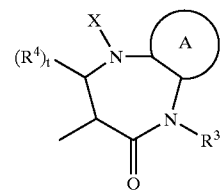

wherein A, B, $R^3$, $R^4$, X, m and t are as defined herein.

More preferably, W is a substituted ε-caprolactam of the formula:

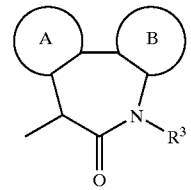

wherein A, B, and $R^3$ are as defined herein. In separate preferred embodiments, this invention is also directed to compounds of formula I wherein W is independently selected from each of the substituted ε-caprolactam or the substituted 1,5-diazepin-2-one illustrated above.

Rings A and B may be the same or different and are preferably independently selected from the group consisting of aryl, cycloalkyl, cycloalkenyl, heteroaryl and heterocyclic. More preferably, rings A and B are independently selected from the group consisting of aryl and cycloalkyl. Still more preferably, rings A and B are independently aryl.

Particularly preferred A and B rings include, by way of example, phenyl, substituted phenyl, including fluoro-substituted phenyl, cyclohexyl and the like. When the A and B rings are fused to one another, they preferably form a naphthyl or substituted naphthyl ring.

Particularly preferred C rings include, by way of example, pyrrolidinyl, piperidinyl, morpholino and the like.

In one preferred embodiment of this invention, W is a substituted ε-caprolactam of the formula:

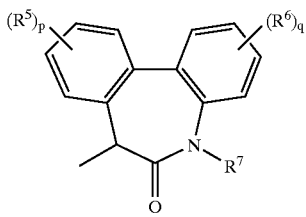

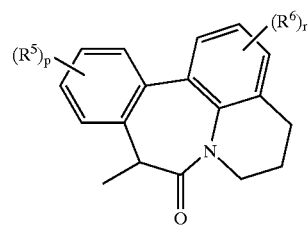

wherein each $R^5$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-akyl, —SO$_2$-substituted alkyl, —SO$_2$-aryl, and —SO$_2$-heteroaryl;

each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;

$R^7$ is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;

p is an integer from 0 to 4; q is an integer from 0 to 4; and salts thereof.

Preferably, $R^5$ and $R^6$ are independently selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy. More preferably, when present, $R^5$ and $R^6$ are fluoro.

$R^7$ is preferably selected from the group consisting of hydrogen, alkyl, substituted alkyl, acyl, aryl, cycloalkyl and substituted cycloalkyl. More preferably, $R^7$ is selected from the group consisting of hydrogen, alkyl, substituted alkyl and cycloalkyl.

Particularly preferred $R^7$ substituents include, by way of example, hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl, cyclohexyl, and the like.

In a preferred embodiment, n is 0; p, q and r are independently 0, 1 or 2; each $R^5$ in the above formula is independently selected from the group consisting of alkyl, substituted alkyl, alkoxy, and halo; each $R^6$ is independently selected from the group consisting of alkyl, substituted alkyl, alkoxy, and halo; and each $R^7$ is independently selected from the group consisting of alkyl, substituted alkyl, cycloalkyl and aryl. Preferably, p and q are independently 0 or 1.

In another preferred embodiment of this invention, W is a substituted ε-caprolactam of the formula:

wherein $R^5$, $R^6$, and p are as defined herein and r is an integer from 0 to 3; and salts thereof.

In a preferred embodiment, n is 0; p and r are independently 0, 1 or 2; each $R^5$ in the above formula is independently selected from the group consisting of alkyl, substituted alkyl, alkoxy, and halo; and each $R^6$ is independently selected from the group consisting of alkyl, substituted alkyl alkoxy, and halo. Preferably, p and r are independently 0 or 1.

In still another preferred embodiment of this invention, W is a substituted ε-caprolactam of the formula:

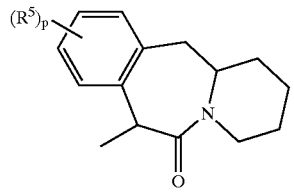

wherein $R^5$, and p are as defined herein; and salts thereof.

In yet another preferred embodiment of this invention, W is a substituted ε-caprolactam of the formula:

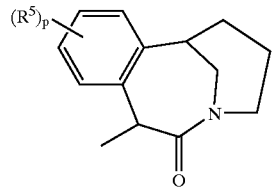

wherein $R^5$ and p are as defined herein; and salts thereof.

In still another preferred embodiment of this invention, W is a 1,5-benzodiazepine of the formula:

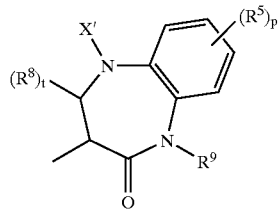

where $R^5$, p and t are as defined herein; each $R^8$ is independently selected from the group consisting of alkyl, heterocyclic and aryl; $R^9$ is alkyl; and X' is selected from the group consisting of hydrogen, alkyl and aryl; or X' and one of $R^8$ and the atoms to which they are attached form a double bond.

Preferably, $R^8$ is alkyl or aryl. More preferably, $R^8$ is isopropyl or phenyl.

X' is preferably hydrogen, methyl or phenyl; or X' and one of $R^8$ and the atoms to which they are attached preferably form a double bond.

When n is 1, W is preferably a substituted ε-caprolactam selected from the group consisting of:

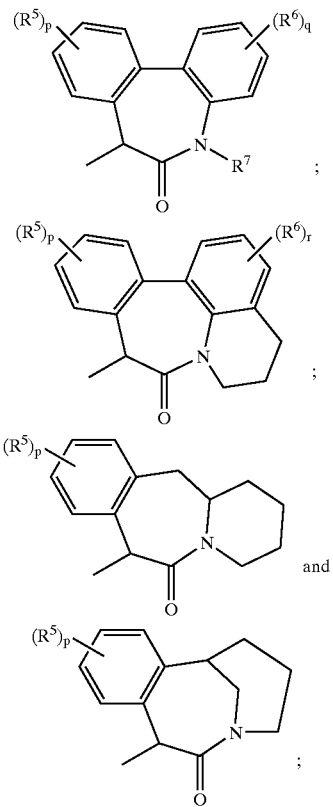

or a 1,5-benzodiazepine of the formula:

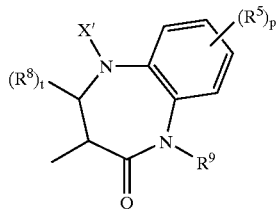

wherein $R^4$, $R^5$, $R^6$, $R^7$, $R^8$, $R^9$, X', m, p, q, r and t are as defined herein. Preferably, in this embodiment, p, q and r are independently 0 or 1; each $R^5$ is independently selected from the group consisting of alkyl, substituted alkyl, cycloalkyl, alkoxy, and halo; each $R^6$ is independently selected from the group consisting of alkyl, substituted alkyl, cycloalkyl, alkoxy, and halo; and each $R^7$ is independently selected from the group consisting of alkyl, substituted alkyl, cycloalkyl and aryl. More preferably, p, q and r are 0.

Preferred substituted ε-caprolactams (i.e., W) include, by way of example, 5,7-dihydro-6H-dibenz[b,d]azepin-6-one-5-yl, 7-methyl-5,7-dihydro-6H-dibenz[b,d]azepin-6-one-5-yl, 7-(2-methylpropyl)-5,7-dihydro-6H-dibenz[b,d]azepin-6-one-5-yl, 7-(methoxyacetyl)-5,7-dihydro-6H-dibenz[b,d]azepin-6-one-5-yl, 7-(3,3-dimethylbutan-2-onyl)-5,7-dihydro-6H-dibenz[b,d]azepin-6-one-yl, 7-phenbutyl-5,7-dihydro-6H-dibenz[b,d]azepin-6-one-yl, 7cyclopropymethyl-5,7-dihydro-6H-dibenz[b,d]azepin-6-one-yl, 7-(2',2',2'-trifluoroethyl)-5,7-dihydro-6H-dibenz[b,d]azepin-6-one-yl, 7-cyclohexyl-5,7-dihydro-6H-dibenz[b,d]azepin-6-one-5-yl, 7-hexyl-5,7-dihydro-6H-dibenz[b,d]azepin-6-one-5-yl, 9-fluoro-7-methyl-5,7-dihydro-6H-dibenz[b,d]azepin-6-one-5-yl, 10-fluoro-7-methyl-5,7-dihydro-6H-dibenz[b,d]azepin-6-one-5-yl, 13-fluoro-7-methyl-5,7-dihydro-6H-dibenz[b,d]azepin-6-one-5-yl and 7-methyl-1,2,3,4,5,7-hexahydro-6H-dicyclohexyl[b,d]azepin-6-one-5-yl.

Preferred substituted 1,5-diazepines include, by way of illustration, 1,3-dihydro-1-methyl-4-phenyl-(2H)-1,5-benzodiazepin-2-one-3-yl, 1,3,4,5-tetrahydro-1-methyl-4-phenyl-(2H)-1,5-benzodiazepin-2-one-3-yl, 1,3-dihydro-1-methyl-4-isopropyl-(2H)-1,5-benzodiazepin-2-one-3-yl, 1,3,4,5-tetrahydro-1-methyl-4-isopropyl-(2H)-1,5-benzodiazepin-2-one-3-yl, 1-methyl-5-phenyl-1,3,4,5-tetrahydro-(2H)-1,5-benzodiazepin-2-one-3-yl and 1,5-bis-methyl-1,3,4,5-tetrahydro-(2H)-1,5-benzodiazepine-2-one-3-yl.

Compounds of this invention include, by way of example, the following:

5-amino-7-methyl-5,7-dihydro-6H-dibenz[b,d]azepin-6-one 5-(N-Boc-amino)-5,7-dihydro-6H-dibenz[b,d]azepin-6-one 5-(N-Boc-amino)-7-(2-methylpropyl)-5,7-dihydro-6H-dibenz[b,d]azepin-6-one 5-amino-7-(2-methylpropyl)-5,7-dihydro-6H-dibenz[b,d]azepin-6-one 5-(N-Boc-amino)-7-(methoxycarbonylmethyl)-5,7-hydro-6H-dibenz[b,d]azepin-6one 5-amino-7-(methoxycarbonylmethyl)-5,7-dihydro-6H-dibenz[b,d]azepin-6-one 5-(N-Boc-amino)-7-(3,3-dimethyl-butanonyl)-5,7-dihydro-6H-dibenz[b,d]azepin-6-one 5-amino-7-(3,3-dimethyl-2-butanonyl)-5,7-dihydro-6H-dibenz[b,d]azepin-6-one 5-amino-7-phenbutyl-5,7-dihydro-6H-dibenz[b,d]azepin-6-one 5-amino-7-cyclopropymethyl-5,7-dihydro-6H-dibenz[b,d]azepin-6-one 5-amino-7-(2',2',2'-trifluoroethyl)-5,7-dihydro-6H-dibenz[b,d]azepin-6-one 5-amino-7-cyclohexyl-5,7-dihydro-6H-dibenz[b,d]-azepin-6-one 5-amino-7-hexyl-5,7-dihydro-6H-dibenz[b,d]azepin-6-one 5-amino-9-fluoro-7-methyl-5,7-dihydro-6H-dibenz[b,d)azepin-6-one 5-amino-10-fluoro-7-methyl-5,7-dihydro-6H-dibenz[b,d]azepin-6-one 5-amino-13-fluoro-7-methyl-5,7-dihydro-6H-dibenz[b,d]azepin-6-one 5-amino-7-methyl-1,2,3,4,5,7-hexahydro-6H-dicyclohexyl[b,d]azepin-6-one 5-(N-Boc-L-alaninyl)amino-7-methyl-5,7-dihydro H-dibenz[b,d]azepin-6-one 5-(L-alaninyl)amino-7-methyl-5,7-dihydro-6H-dibenz[b,d]azepin-6-one 5-(N-Boc-L-valinyl)amino-7-methyl-5,7-dihydro-6H-dibenz[b,d]azepin-6-one 5-(L-valinyl)amino-7-methyl-5,7-dihydro-6H-dibenz[b,d]azepin-6-one 5-(N-Boc-L-tert-leucinyl)amino-7-methyl-5,7-dihydro-6H-dibenz[b,d]azepin-6-one 5-(L-tert-leucinyl)amino-7-methyl-5,7-dihydro-6H-dibenz[b,d]azepin-6-one 5-(N-Boc-L-alaninyl)amino-9-fluoro-7-methyl-5,7-dihydro-6H-dibenz[b,d]azepin-6-one 5-(L-alaninyl)amino-9-fluoro-7-methyl-5,7-dihydro-6H-dibenz[b,d]azepin-6-one 5-(N-Boc-L-alaninyl)amino-10-fluoro-7-methyl-5,7-dihydro-6H-dibenz[b,d]azepin-6-one 5-(L-alaninyl)amino-10-fluoro-7-methyl-5,7-dihydro-6H-dibenz[b,d]azepin-6-one 5-(N-Boc-L-alaninyl)amino-13-fluoro-7-methyl-5,7-dihydro-6H-dibenz[b,d]azepin-6-one 5-(L-alaninyl)amino-13-fluoro-7-methyl-5,7-dihydro-6H-dibenz[b,d]azepin-6-one 5-(N-Boc-L-alaninyl)amino-7-cyclopropylmethyl-5,7-dihydro-6H-dibenz[b,d]azepin-6-one 5-(L-alaninyl)amino-7-cyclopropylmethyl-5,7-dihydro-6H-dibenz[b,d]azepin-6-one 5-(N-Boc-L-alaninyl)amino-7-phenbutyl-5,7-dihydro-6H-dibenz[b,d]azepin-6-one 5-(L-alaninyl)amino-7-phenbutyl-5,7-dihydro-6H-dibenz[b,d]azepin-6-one 5-(N-Boc-L-valinyl)amino-7-cyclopropylmethyl-5,7-dihydro-6H-dibenz[b,d]azepin-6-one 5-(L-valinyl)amino-7-cyclopropylmethyl-5,7-dihydro-6H-dibenz[b,d]azepin-6-one 5-(N-Boc-L-valinyl)amino-7-phenbutyl-5,7-dihydro-6H-dibenz[b,d]azepin-6-one 5-(L-valinyl)amino-7-phenbutyl-5,7-dihydro-6H-dibenz[b,d]azepin-6-one 5-(N-Boc-L-valinyl)amino-7-hexyl-5,7-dihydro-6H-dibenz[b,d]azepin-6-one 5-(L-valinyl)amino-7-hexyl-5,7-dihydro-6H-dibenz[b,d]azepin-6-one 5-(N-Boc-L-valinyl)amino-9-fluoro-7-methyl-5,7-dihydro-6H-dibenz[b,d]azepin-6-one 5-(L-valinyl)amino-9-fluoro-7-methyl-5,7-dihydro-6H-dibenz[b,d]azepin-6-one 5-(N-Boc-L-valinyl)amino-10-fluoro-7-methyl-5,7-dihydro-6H-dibenz[b,d]azepin-6-one 5-(L-valinyl)amino-10-fluoro-7-methyl-5,7-dihydro-6H-dibenz[b,d]azepin-6-one 5-(N-Boc-L-valinyl)amino-13-fluoro-7-methyl-5,7-dihydro-6H-dibenz[b,d]azepin-6-one 5-(L-valinyl)amino-13-fluoro-7-methyl-5,7-dihydro-6H-dibenz[b,d]azepin-6-one 5-amino-9,13-difluoro-7-methyl-5,7-dihydro-6H-dibenz[b,d]azepin-6-one 5-amino-10,13-difluoro-7-methyl-5,7-dihydro-6H-dibenz[b,d]azepin-6-one 5-aminohexahydropyrido[a]benz[d]azepin-6-one 9-amino-5,6-Dihydro-4H-quino[8,1-ab][3]benzazepin-8(9H)-one 9-(N'-Boc-L-alaninyl)amino-5,6-Dihydro-4H-quino[8,1-ab][3]benzazepin-8(9H)-one 9-(N'-L-alaninyl)amino-5,6-dihydro-4H-quino[8,1-ab][3]benzazepin-8(9H)-one 7-amino-1,3,4,7,12,12a-hexahydropyrido[2,1-b][3]benzazepin-6(2H)-one 1-amino-4,5,6,7-tetrahydro-3,7-methano-3H-3-benzazonin-2(1H)-one 1-(N'-Boc-L-alaninyl)amino-4,5,6,7-tetrahydro-3,7-methano-3H-3-benzazonin-2(1H)-one 1-(N'-L-alaninyl)amino-4,5,6,7-tetrahydro-3,7-methano-3H-3-benzazonin-2(1H)-one and salts thereof.

Additional compounds of this invention include, by way of example, the following:

1,3-dihydro-3-amino-1-methyl-4-phenyl-(2H)-1,5-benzodiazepin-2-one 1,3-dihydro-3-(N-Boc-L-alaninyl)amino-1-methyl-4-phenyl-(2H)-1,5-benzodiazepin-2-one 1,3-dihydro-3-(L-alaninyl)amino-1-methyl-4-phenyl-(2H)-1,5-benzodiazepin-2-one 1,3,4,5-tetrahydro-3-amino-1-methyl-4-phenyl-(2H)-1,5-benzodiazepin-2-one 1,3,4,5-tetrahydro-3-(N-Boc-L-alaninyl)amino-1-methyl-4-phenyl-(2H)-1,5-benzodiazepin-2-one 1,3,4,5-tetrahydro-3-(L-alaninyl)amino-1-methyl-4-phenyl-(2H)-1,5-benzodiazepin-2-one 1,3-dihydro-3-amino-1-methyl-4-isopropyl-(2H)-1,5-benzodiazepin-2-one 1,3-dihydro-3-(N-Boc-L-alaninyl)amino-1-methyl-4-isopropyl-(2H)-1,5-benzodiazepin-2-one 1,3-dihydro-3-L-alaninyl)amino-1-methyl-4-isopropyl-(2H)-1,5-benzodiazepin-2-one 1,3,4,5-tetrahydro-3-amino-1-methyl-4-isopropyl-(2H)-1,5-benzodiazepin-2-one 1,3,4,5-tetrahydro-3-(N-Boc-L-alaninyl)amino-1-methyl-4-isopropyl-(2H)-1,5-benzodiazepin-2-one 1,3,4,5-tetrahydro-3-(L-alaninyl)amino-1-methyl-4-isopropyl-(2H)-1,5-benzodiazepin-2-one 1,3-dihydro-3-(N-Boc-L-norleucinyl)amino-1-methyl-4-isopropyl-2H)-1,5-benzodiazepin-2-one 1,3-dihydro-3-(L-norleucinyl)amino-1-methyl-4-isopropyl-(2H)-1,5-benzodiazepin-2-one 1,3,4,5-tetrahydro-3-(N-Boc-L-norleucinyl)amino-1-methyl-4-isopropyl-(2H)-1,5-benzodiazepin-2-one 1,3,4,5-tetrahydro-3-(L-norleucinyl)amino-1-methyl-4-isopropyl-(2H)-1,5-benzodiazepin-2-one 1,3-dihydro-3-(N-Boc-L-norleucinyl)amino-1-methyl-4-phenyl-(2H)-1,5-benzodiazepin-2-one 1,3-dihydro-3-(L-norleucinyl)amino-1-methyl-4-phenyl-(2H)-1,5-benzodiazepin-2-one 3-amino-1-methyl-5-phenyl-1,3,4,5-tetrahydro-(2H)-1,5-benzodiazepin-2-one 3-(N-Boc-L-alaninyl)amino-1-methyl-5-phenyl-1,3,4,5-tetrahydro-(2H)-1,5-benzodiazepine-2-one 3-(L-alaninyl)amino-1-methyl-5-phenyl-1,3,4,5-etrahydro-(2H)-1,5-benzodiazepine-2-one 3-(N-Boc-L-valinyl)amino-1-methyl-5-phenyl-1,3,4,5-tetrahydro-(2H)-1,5-benzodiazepin-2-one 3-(L-valinyl)amino-1-methyl-5-phenyl-1,3,4,5-tetrahydro-(2H)-1,5-benzodiazepin-2-one 3-[N-Boc-L-(O-benzyl)-threoninyl]amino-1-methyl-5-phenyl-1,3,4,5-tetrahydro-(2H)-1,5-benzodiazepin-2-one 3-[L-(O-benzyl)-threoninyl]amino-1-methyl-5-phenyl-1,3,4,5-tetrahydro-(2H)-1,5-benzodiazepin-2-one 3-[N-Boc-(S)-phenylglycinyl]amino-1-methyl-5-phenyl-1,3,4,5-tetrahydro-(2H)1,5-benzodiazepine 2-one 3-[(S)-phenylglycinyl]amino-1-methyl-5-phenyl-1,3,4,5-tetrahydro-(2H)-1,5-benzodiazepine 2-one 3-amino-1,5-bis-methyl-1,3,4,5-tetrahydro-(2H)-1,5-benzodiazepine-2-one 3-(N-Boc-L-alaninyl)amino-1,5-bis-methyl-1,3,4,5-tetrahydro-(2H)-1,5-benzadiazepine-2-one 3-(L-alaninyl)amino-1,5-bis-methyl-1,3,4,5-tetrahydro-(2H)-1,5-benzadiazepine-2-one and salts thereof.

In one embodiment, the following compounds are not preferred:

3-amino-1-methyl-5-phenyl-1,3,4,5-tetrahydro-(2H)-1,5-benzodiazepin-2-one 3-(N-Boc-L-alaninyl)amino-1-methyl-5-phenyl-1,3,4,5-tetrahydro-(2H)-1,5-benzodiazepine-2-one, and 3-(L-alaninyl)amino-1-methyl-5-phenyl-1,3,4,5-tetrahydro-(2H)-1,5-benzodiazepine-2-one.

Preferred compounds include those defined by the formulas as set forth in the following Tables and salts thereof.

TABLE I

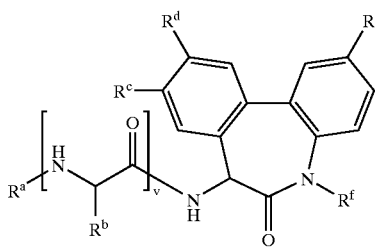

| $R^a$ | $R^b$ | $R^c$ | $R^d$ | $R^e$ | $R^f$ | v |
|---|---|---|---|---|---|---|
| H— | — | H— | H— | H— | CH$_3$— | 0 |
| Boc—[a] | — | H— | H— | H— | H— | 0 |
| Boc— | — | H— | H— | H— | (CH$_3$)$_2$CHCH$_2$— | 0 |
| H— | — | H— | H— | H— | (CH$_3$)$_2$CHCH$_2$— | 0 |
| Boc— | — | H— | H— | H— | CH$_3$OC(O)CH$_2$— | 0 |
| H— | — | H— | H— | H— | CH$_3$OC(O)CH$_2$— | 0 |
| Boc— | — | H— | H— | H— | (CH$_3$)$_3$CC(O)CH$_2$— | 0 |
| H— | — | H— | H— | H— | (CH$_3$)$_3$CC(O)CH$_2$— | 0 |
| H— | — | H— | H— | H— | Ph(CH$_2$)$_4$— | 0 |
| H— | — | H— | H— | H— | cyclopropy-CH$_2$— | 0 |
| H— | — | H— | H— | H— | CF$_3$CH$_2$— | 0 |
| H— | — | H— | H— | H— | cyclohexyl- | 0 |
| H— | — | H— | H— | H— | CH$_3$(CH$_2$)$_5$— | 0 |
| H— | — | F— | H— | H— | CH$_3$— | 0 |
| H— | — | H— | F— | H— | CH$_3$— | 0 |
| H— | — | H— | H— | F— | CH$_3$— | 0 |
| Boc— | CH$_3$— | H— | H— | H— | CH$_3$— | 1 |
| H— | CH$_3$— | H— | H— | H— | CH$_3$— | 1 |
| Boc— | (CH$_3$)$_2$CH— | H— | H— | H— | CH$_3$— | 1 |
| H— | (CH$_3$)$_2$CH— | H— | H— | H— | CH$_3$— | 1 |
| Boc— | (CH$_3$)$_3$C— | H— | H— | H— | CH$_3$— | 1 |
| H— | (CH$_3$)$_3$C— | H— | H— | H— | CH$_3$— | 1 |
| Boc— | CH$_3$— | F— | H— | H— | CH$_3$— | 1 |
| H— | CH$_3$— | F— | H— | H— | CH$_3$— | 1 |
| Boc— | CH$_3$— | H— | F— | H— | CH$_3$— | 1 |
| H— | CH$_3$— | H— | F— | H— | CH$_3$— | 1 |
| Boc— | CH$_3$— | H— | H— | F— | CH$_3$— | 1 |
| H— | CH$_3$— | H— | H— | F— | CH$_3$— | 1 |
| Boc— | CH$_3$— | H— | H— | H— | cyclopropy-CH$_2$— | 1 |
| H— | CH$_3$— | H— | H— | H— | cyclopropy-CH$_2$— | 1 |
| Boc— | CH$_3$— | H— | H— | H— | Ph(CH$_2$)$_4$— | 1 |
| H— | CH$_3$— | H— | H— | H— | Ph(CH$_2$)$_4$— | 1 |
| Boc— | (CH$_3$)$_2$CH— | H— | H— | H— | cyclopropy-CH$_2$— | 1 |
| H— | (CH$_3$)$_2$CH— | H— | H— | H— | cyclopropy-CH$_2$— | 1 |
| Boc— | (CH$_3$)$_2$CH— | H— | H— | H— | Ph(CH$_2$)$_4$— | 1 |
| H— | (CH$_3$)$_2$CH— | H— | H— | H— | Ph(CH$_2$)$_4$— | 1 |
| Boc— | (CH$_3$)$_2$CH— | H— | H— | H— | CH$_3$(CH$_2$)$_5$— | 1 |
| H— | (CH$_3$)$_2$CH— | H— | H— | H— | CH$_3$(CH$_2$)$_5$— | 1 |
| Boc— | (CH$_3$)$_2$CH— | F— | H— | H— | CH$_3$— | 1 |
| H— | (CH$_3$)$_2$CH— | F— | H— | H— | CH$_3$— | 1 |
| Boc— | (CH$_3$)$_2$CH— | H— | F— | H— | CH$_3$— | 1 |
| H— | (CH$_3$)$_2$CH— | H— | F— | H— | CH$_3$— | 1 |
| Boc— | (CH$_3$)$_2$CH— | H— | H— | F— | CH$_3$— | 1 |
| H— | (CH$_3$)$_2$CH— | H | H— | F— | CH$_3$— | 1 |

TABLE I-continued

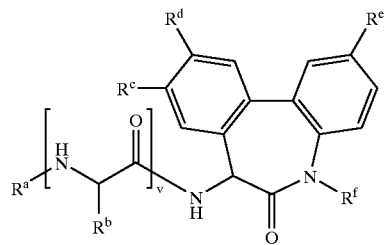

| $R^a$ | $R^b$ | $R^c$ | $R^d$ | $R^e$ | $R^f$ | v |
|---|---|---|---|---|---|---|
| H— | — | F— | H— | F— | CH$_3$— | 0 |
| H— | — | H— | F— | F— | CH$_3$— | 0 |

[a]Boc = tert-butoxycarbonyl = (CH$_3$)$_3$COC(O)—

TABLE II

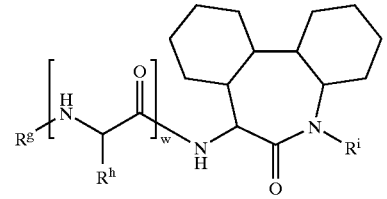

| $R^g$ | $R^h$ | $R^i$ | w |
|---|---|---|---|
| H— | — | CH$_3$— | 0 |

TABLE III

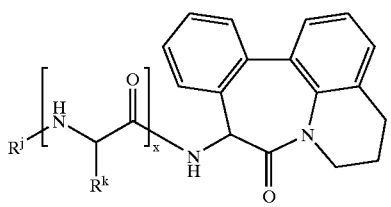

| $R^j$ | $R^k$ | x |
|---|---|---|
| H— | — | 0 |
| H— | CH$_3$— | 1 |

TABLE IV

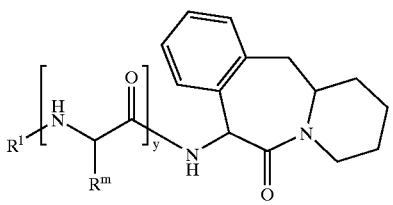

| $R^l$ | $R^m$ | y |
|---|---|---|
| H— | — | 0 |

TABLE V

| $R^n$ | $R^o$ | z |
|---|---|---|
| H— | — | 0 |
| Boc—[a] | CH₃— | 1 |
| H— | CH₃— | 1 |

[a]Boc = tert-butoxycarbonyl = (CH₃)₃COC(O)—

TABLE VI

| $R^p$ | $R^q$ | $R^r$ | $R^s$ | u |
|---|---|---|---|---|
| H— | — | —Ph | —CH₃ | 0 |
| H— | — | —CH(CH₃)₂ | —CH₃ | 0 |
| Boc—[a] | —CH₃ | —Ph | —CH₃ | 1 |
| H— | —CH₃ | —Ph | —CH₃ | 1 |
| Boc— | —CH₃ | —CH(CH₃)₂ | —CH₃ | 1 |
| H— | —CH₃ | —CH(CH₃)₂ | —CH₃ | 1 |
| Boc— | —(CH₂)₃CH₃ | —CH(CH₃)₂ | —CH₃ | 1 |
| H— | —(CH₂)₃CH₃ | —CH(CH₃)₂ | —CH₃ | 1 |
| Boc— | —(CH₂)₃CH₃ | —Ph | —CH₃ | 1 |
| H— | —(CH₂)₃CH₃ | —Ph | —CH₃ | 1 |

[a]Boc = tert-butoxycarbonyl = (CH₃)₃COC(O)—

TABLE VII

| $R^p$ | $R^q$ | $R^r$ | $R^s$ | $R^t$ | u |
|---|---|---|---|---|---|
| H— | — | —Ph | —CH₃ | —H | 0 |
| H— | — | —CH(CH₃)₂ | —CH₃ | —H | 0 |
| Boc—[a] | —CH₃ | —Ph | —CH₃ | —H | 1 |
| H— | —CH₃ | —Ph | —CH₃ | —H | 1 |
| Boc— | —CH₃ | —CH(CH₃)₂ | —CH₃ | —H | 1 |
| H— | —CH₃ | —CH(CH₃)₂ | —CH₃ | —H | 1 |
| Boc— | —(CH₂)₃CH₃ | —CH(CH₃)₂ | —CH₃ | —H | 1 |
| H— | —(CH₂)₃CH₃ | —CH(CH₃)₂ | —CH₃ | —H | 1 |
| H— | — | —H | —CH₃ | —Ph | 0 |
| Boc— | —CH₃ | —H | —CH₃ | —Ph | 1 |
| H— | —CH₃ | —H | —CH₃ | —Ph | 1 |
| Boc— | —CH(CH₃)₂ | —H | —CH₃ | —Ph | 1 |
| H— | —CH(CH₃)₂ | —H | —CH₃ | —Ph | 1 |
| Boc— | —CH(CH₃)OCH₂—Ph | —H | —CH₃ | —Ph | 1 |
| H— | —CH(CH₃)OCH₂—Ph | —H | —CH₃ | —Ph | 1 |
| Boc— | —Ph | —H | —CH₃ | —Ph | 1 |
| H— | —Ph | —H | —CH₃ | —Ph | 1 |
| H— | — | —H | —CH₃ | —CH₃ | |
| Boc— | —CH₃ | —H | —CH₃ | —CH₃ | 1 |
| H— | —CH₃ | —H | —CH₃ | —CH₃ | 1 |

[a]Boc = tert-butoxycarbonyl (CH₃)₃COC(O)—

DETAILED DESCRIPTION OF THE INVENTION

For purposes of describing this invention in all its aspects, the following terms have the followings meanings unless otherwise indicated. All other terms have their conventional art-recognized meanings.

Definitions

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr (SEQ ID NO: 1)

or a sequence which is substantially homologous thereto.

"Alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, decyl and the like.

"Substituted alkyl" refers to an alkyl group, preferably of from 1 to 20 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO2-aryl, and —SO₂-heteroaryl.

"Alkylene" refers to divalent alkylene groups preferably having from 1 to 10 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to an alkylene group, preferably of from 1 to 10 carbon atoms, having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Additionally, such substituted alkylene groups include those where 2 substituents on the alkylene group are fused to form one or more cycloalkyl, aryl, heterocyclic or heteroaryl groups fused to the alkylene group. Preferably such fused cycloalkyl groups contain from 1 to 3 fused ring structures.

"Alkenylene" refers to divalent alkenylene groups preferably having from 2 to 10 carbon atoms and more preferably 2 to 6 carbon atoms. This term is exemplified by groups such as ethenylene (—CH=CH—), the propenylene isomers (e.g., —CH$_2$CH=CH— and —C(CH$_3$)=CH—) and the like.

"Substituted alkenylene" refers to an alkenylene group, preferably of from 2 to 10 carbon atoms, having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Additionally, such substituted alkylene groups include those where 2 substituents on the alkylene group are fused to form one or more cycloalkyl, aryl, heterocyclic or heteroaryl groups fused to the alkylene group.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O—". Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—" where substituted alkyl is as defined above.

"Alkylalkoxy" refers to the group "-alkylene-O-alkyl" which includes by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

"Alkylthioalkoxy" refers to the group "-alkylene-S-alkyl" which includes by way of example, methylenethiomethoxy (—CH$_2$SCH$_3$), ethyjenethiomethoxy (—CH$_2$CH$_2$SCH$_3$), n-propylene-thio-iso-propoxy (—CH$_2$CH$_2$CH$_2$SCH(CH$_3$)$_2$), methylenethio-t-butoxy (—CH$_2$SC(CH$_3$)$_3$) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—H=CH$_2$), n-propenyl (—CH$_2$CH=CH$_2$), iso-propenyl (—C(CH$_3$)=CH$_2$), and the like.

"Substituted alkenyl" refers to an alkenyl group as defined above having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$C≡CH) and the like.

"Substituted alkynyl" refers to an alkynyl group as defined above having from 1 to 3 substituents selected from the group consisting of alkoxy, substituted alkoxy, cycloalkyl, substituted cycloalkyl, cycloalkoxy, substituted cycloalkoxyl, acyl, acylamino, acyloxy, amino, substituted amino, aminoacyl, aminoacyloxy, cyano, halogen, hydroxyl, carboxyl, carboxylalkyl, keto, thioketo, thiol, thioalkoxy, substituted thioalkoxy, aryl, heteroaryl, heterocyclic, heterocyclooxy, nitro —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

"Acylamino" refers to the group —C(O)NRR where each R is independently selected from the group consisting of hydrogen, alkyl, substituted alkyl, aryl, heteroaryl, heterocyclic and where both R groups are joined to form a heterocyclic group, wherein alkyl, substituted alkyl, aryl, heteroaryl and heterocyclic are as defined herein.

"Amino" refers to the group —NH$_2$.

"Substituted amino" refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, heteroaryl, heterocyclic and where both R groups are joined to form a heterocyclic group. When both R groups are hydrogen, —N(R)$_2$ is an amino group. Examples of substituted amino groups include, by way of illustration, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like.

The term "amino-blocking group" or "amino-protecting group" refers to any group which, when bound to an amino group, prevents undesired reactions from occurring at the amino group and which may be removed by conventional chemical and/or enzymatic procedures to reestablish the amino group. Any known amino-blocking group may be used in this invention. Typically, the amino-blocking group is selected so as to render the resulting blocked-amino group unreactive to the particular reagents and reaction conditions employed in a subsequent predetermined chemical reaction or series of reactions. After completion of the reaction(s), the amino-blocking group is selectively removed to regenerate the amino group. Examples of suitable amino-blocking groups include, by way of illustration, tert-butoxycarbonyl (Boc), benzyloxycarbonyl (Cbz), acetyl, 1-(1'-adamantyl)-1-methylethoxycarbonyl (Acm), allyloxycarbonyl (Aloc), benzyloxymethyl (Bom), 2-p-biphenylisopropyloxycarbonyl (Bpoc), tert-butyldimethylsilyl (Bsi), benzoyl (Bz), benzyl (Bn), 9-fluorenyl-methyloxycarbonyl (Fmoc), 4-methylbenzyl, 4-methoxybenzyl, 2-nitrophenylsulfenyl (Nps), 3-nitro-2-pyridinesulfenyl (NPys), trifluoroacetyl (Tfa), 2,4,6-trimethoxybenzyl (Tmob), trityl (Trt), and the like. If desired, amino-blocking groups covalently attached to a solid support may also be employed.

"Aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

"Aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

"Acyloxy" refers to the groups alkyl-C(O)O—, substituted alkyl-C(O)O—, cycloalkyl-C(O)O—, substituted cycloalkyl-C(O)—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

"Aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

"Carboxyalkyl" refers to the groups "—C(O)Oalkyl" and "—C(O)O—substituted alkyl" where alkyl is as defined above.

"Cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

"Substituted cycloalkyl" refers to cycloalkyl groups having from 1 to 5 (preferably 1 to 3) substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Cycloalkenyl" refers to cyclic alkenyl groups of from 4 to 8 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

"Substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Halo" or "halogen" refers to fluoro, chloro, bromo and iodo and preferably is either fluoro or chloro.

"Heteroaryl" refers to an aromatic group of from, 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heterocyclic, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl —SO$_2$-aryl, —SO$_2$-heteroaryl and trihalomethyl. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroaryloxy" refers to the group "—O-heteroaryl".

"Heterocycle" or "heterocyclic" refers to a monovalent saturated or unsaturated group having a single ring or multiple condensed rings, from 1 to 15 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl. Such heterocyclic groups can have a single ring or multiple condensed rings. Preferred heterocyclics include morpholino, piperidinyl, and the like.

Examples of heterocycles and heteroaryls include, but are not limited to, pyrrole, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenarithroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Heterocyclooxy" refers to the group "—O-heterocycle".

"Keto" or "oxo" refers to the group "=O".

"Oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S— wherein the aryl group is as defined above including optionally substituted aryl groups also defined above.

"Thioheteroaryloxy" refers to the group heteroaryl-S— wherein the heteroaryl group is as defined above including optionally substituted aryl groups as also defined above.

"Thioketo" refers to the group "=S".

As to any of the above defined groups which contain 1 or more substituents, it is understood, of course, that such groups do not contain any substitution or substitution patterns which are sterically impractical and/or synthetically non-feasible.

The term "5,7-dihydro-6H-dibenz[b,d]azepin-6-one" refers to a polycyclic ε-caprolactam ring system having the formula:

wherein, for nomenclature purposes, the atoms and bonds are numbered and lettered, respectively, as shown.

The term "5,6-dihydro-4H-quino[8,1-ab][3]benzazepin-8 (9H)-one" refers to a polycyclic ε-caprolactam ring system having the formula:

wherein, for nomenclature purposes, the atoms and bonds are numbered and lettered, respectively, as shown.

The term "1,3,4,7,12,12a-hexahydropyrido[2,1-b][3] benzazepin-6(2H)-one" refers to a polycyclic ε-caprolactam ring system having the formula:

wherein, for nomenclature purposes, the atoms and bonds are numbered and lettered, respectively, as shown.

The term "4,5,6,7-tetrahydro-3,7-methano-3H-3-benzazonin-2(1H)-one" refers to a polycyclic ε-caprolactam ring system having the formula:

wherein, for nomenclature purposes, the atoms and bonds are numbered and lettered, respectively, as shown.

The term "1,3-dihydro-(2H)-1,5-benzodiazepin-2-one" refers to a ring system having the formula:

wherein, for nomenclature purposes, the atoms and bonds are numbered and lettered, respectively, as shown.

The term "1,3,4,5-tetrahydro-2H)-1,5-benzodiazepin-2-one" refers to a ring system having the formula:

wherein, for nomenclature purposes, the atoms and bonds are numbered and lettered, respectively, as shown.

The term "salt(s)" refers to salts of a compound of formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "protecting group" or "blocking group" refers to any group which when bound to one or more hydroxyl, thiol, carboxyl or other protectable functional group of the compound prevents reactions from occurring at these groups and which protecting group can be removed by conventional chemical and/or enzymatic steps to reestablish the unprotected functional group. The particular removable blocking group employed is not critical and preferred removable hydroxyl blocking groups include conventional substituents such as allyl, benzyl, acetyl, chloroacetyl, thiobenzyl, benzylidine, phenacyl, tert-butyldiphenylsilyl and any other group that can be introduced chemically onto a hydroxyl functionality and later selectively removed either by chemical or enzymatic methods in mild conditions compatible with the nature of the product.

Preferred carboxyl protecting groups include esters such as methyl, ethyl, propyl, tert-butyl, etc. which can be removed by mild hydrolysis conditions compatible with the nature of the product.

Compound Preparation

The polycyclic α-amino-ε-caprolactams and related compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991,[8] and references cited therein.

In a preferred method of synthesis, the ε-caprolactams of this invention are prepared by first aminating a polycyclic ε-caprolactam to provide a polycyclic α-amino-ε-caprolactam. If desired, the amino group of the polycyclic α-amino-ε-caprolactam can then be coupled with a mono- or diamino acid derivative to provide compounds of formula I wherein n is 1.

The polycyclic ε-caprolactams employed as starting materials in this invention are either commercially available or can be prepared from commercially available materials using conventional procedures and reagents. For example, 5,7-dihydro-6H-dibenz[b,d]azepin-6-one may be prepared by cyclizing a chloromethyl amide intermediate using the procedures set forth in R. F. C. Brown et al., *Tetrahedron Letters* 1971, 8, 667–670[9] and references cited therein.

Additionally, the synthesis of a representative polycyclic ε-caprolactam, i.e., a 5,7-dihydro-6H-dibenz[b,d]azepin-6-one, is illustrated in Scheme 1. As will be readily apparent to those of ordinary skill in the art, the synthetic procedure illustrated in Scheme 1 and the reaction conditions described below can be modified by selecting the appropriate starting materials and reagents to allow the preparation of other polycyclic ε-caprolactams.

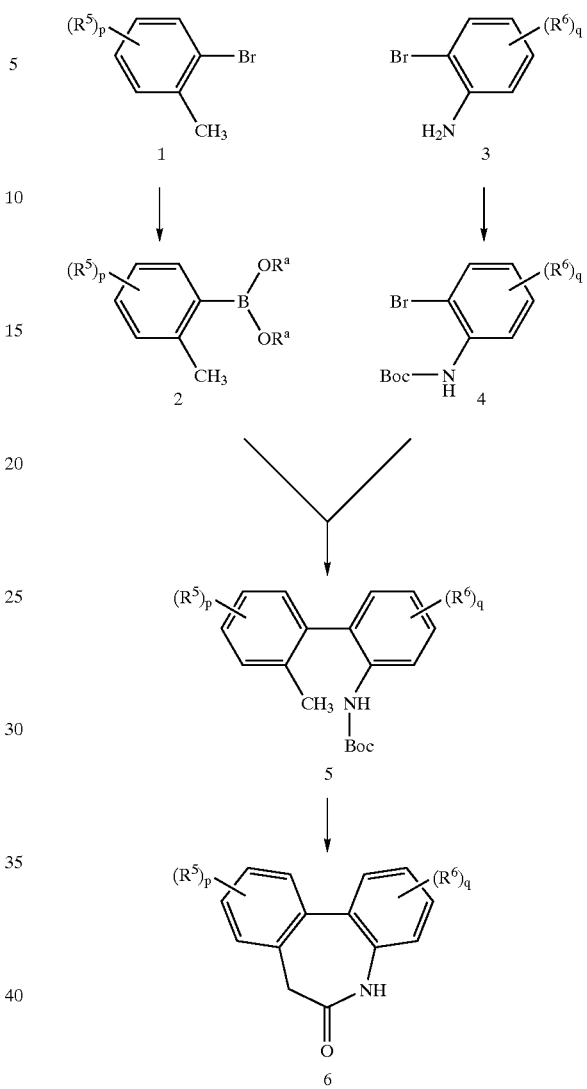

As shown in Scheme 1,5,7-dihydro-6H-dibenz[b,d] azepin-6-one derivatives, 6, wherein $R^5$, $R^6$, p and q are as defined above, can be readily prepared in several steps from a 2-bromotoluene derivative 1 and a 2-bromoaniline derivative 4. In this synthetic procedure, the 2-bromotoluene derivative, 1, is first converted into the corresponding 2-methylphenylboronate ester, 2. This reaction is typically conducted by treating 1 with about 1.0 to about 2.1 equivalents of an alkyl lithium reagent, preferably sec-butyl lithium or tert-butyl lithium, in an inert diluent, such as THF, at a temperature ranging from about −80° C. to about −60° C. for about 0.25 to about 1 hour. The resulting lithium anion is then treated in situ with an excess, preferably 1.5 equivalents, of a trialkylborate, such as trimethylborate. This reaction is initially conducted at −80° C. to about −60° C. and then allowed to warm to about 0° C. to about 30° C. for about 0.5 to about 3 hours. The resulting methyl boronate ester is typically not isolated, but is preferably converted in situ into the pinacol ester by treating the reaction mixture with an excess, preferably about 2.0 equivalents, of pinacol. This reaction is typically conducted at ambient temperature for about 12 to about 24 hours to afford the 2-methylphenylboronate ester, 2, in which both $R^a$ groups are preferably joined together to form —C(CH$_3$)$_2$C(CH$_3$)$_2$—.

In a separate reaction, the amino group of a 2-bromoaniline derivative, 3, is converted into the N-Boc derivative 4 by treating 3 with about 1.0 to about 1.5 equivalents of di-tert-butyl-dicarbonate. Typically, this reaction is conducted at a temperature ranging from 25° C. to about 100° C. for about 12 to 48 hours to afford the N-Boc-2-bromoaniline derivative 4.

As further illustrated in Scheme 1, the 2-methylphenylboronate ester, 2, and the N-Boc-2-bromoaniline derivative 4 can then be coupled to form the biphenyl derivative 5. This reaction is typically conducted by contacting 4 with about 1.0 to about 1.2 equivalents of 2 and about 1.0 to about 1.2 equivalents of potassium carbonate in the presence of a pallidium catalyst, preferably tetrakis (triphenylphosphine)pallidium(0). Generally, this coupling reaction is conducted in a diluent, preferably 20% water/dioxane, under an inert atmosphere at a temperature ranging from about 50° C. to about 100° C. for about 6 to 24 hours.

Biphenyl derivative 5 is then readily converted into the 5,7-dihydro-6H-dibenz[b,d]azepin-6-one 6 by carboxylation of the 2-methyl group, followed by cyclization to form the ε-caprolactam. The carboxylation reaction is typically conducted by contacting 5 with about 2.0 to about 2.5 equivalents of a suitable base, such as sec-butyllithium, tert-butyllithium and the like, in an inert diluent, such as THF, at a temperature ranging from about −100° C. to about −20° C. for about 0.5 to 6 hours. The resulting dianion is then treated with excess anhydrous carbon dioxide to form the carboxylate. Treatment of the carboxylate with excess hydrogen chloride in a suitable diluent, such as methanol, at a temperature ranging from about 25° C. to about 100° C. then affords the: 5,7-dihydro-6H-dibenz[b,d]azepin-6-one 6. Various other polycyclic ε-caprolactam compounds can be prepared by routine modifications of the above described procedures.

Preferred synthetic procedures for aminating a representative polycyclic ε-caprolactam compound are illustrated in Scheme 2. It will be readily apparent to those of ordinary skill in the art that the synthetic procedure illustrated in Scheme 2 and the following reaction conditions can be modified by selecting the appropriate starting materials and reagents to allow the preparation of other polycyclic α-amino-ε-caprolactams of this invention.

Scheme 2

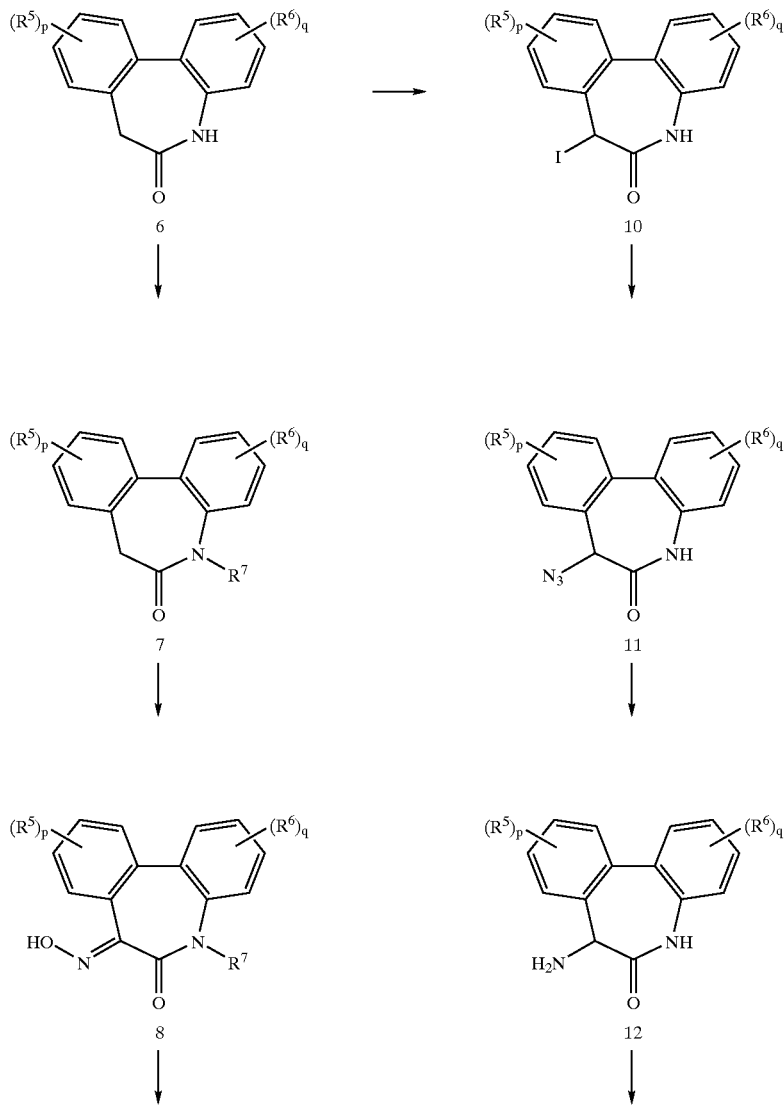

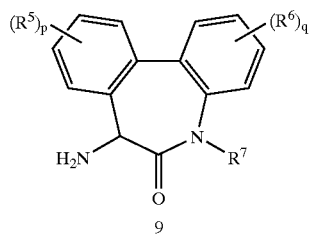 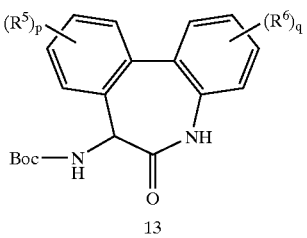

As shown in Scheme 2, 5,7-dihydro-6H-dibenz[b,d] azepin-6-one, 6, is optionally N-alkylated using conventional reagents and conditions to provide a 7-alkyl-5,7-dihydro-6H-dibenz[b,d]azepin-6-one derivative, 7. Typically, this reaction is conducted by first contacting 6 with about 1.0 to 1.5 equivalents of a suitable base, such as sodium hydride, sodium bis(trimethysilyl)amide and the like, in an inert diluent, such as DMF, THF and the like, at a temperature ranging from about −78° C. to about 50° C. for about 0.25 to about 6 hours. The resulting anion is then treated in situ with an excess, preferably about 1.1 to about 2.0 equivalents, of an alkyl, substituted alky, cycloalkyl halide, etc., typically a chloride, bromide or iodide. This reaction is typically conducted at a temperature ranging from about 0° C. to about 60° C. for about 1.0 to about 48 hours to afford the 7-alkyl-5,7-dihydro-6H-dibenz[b,d] azepin-6-one derivative, 7.

The 7-alkyl-5,7-dihydro-6H-dibenz[b,d]azepin-6-one 7 is then oximated by contacting 7 with an excess, preferably with about 1.0 to 1.5 equivalents of a suitable base, such as sodium bis(trimethysilyl)amide and the like, in the presence of about 1.0 to about 2.0 equivalents of an alkyl nitrite. Suitable alkyl nitrites for use in this reaction include, by way of example, butyl nitrite, isoamyl nitrite and the like. This reaction is typically conducted in an inert diluent, such as THF and the like, at a temperature ranging from about −10° C. to about 20° C. for about 0.5 to about 6 hours to afford the 7-alkyl-5-oximo-5,7-dihydro-6H-dibenz[b,d]azepin-6-one derivative 8.

Reduction of 8 using conventional reagents and conditions then affords the 5-amino-7-alkyl-5,7-dihydro-6H-dibenz[b,d]azepin-6-one 9. Preferably, this reduction reaction is conducted by hydrogenating the oxime 8 in the presence of a catalyst, such as Raney nickel. This reaction is typically conducted under about 200 psi to about 600 psi of hydrogen at a temperature of about 70° C. to about 120° C. for about 8 to 48 hours in a diluent, preferably a mixture of ethanol and ammonia (about 20:1). Alternatively, in another preferred procedure, the oxime may be reduced using 10% Pd/C and between about 30 to about 60 psi of hydrogen at a temperature ranging from about 20° C. to about 50° C. for about 4 hours. The resulting 5-amino-7-alkyl-5,7-dihydro-6H-dibenz[b,d]azepin-6-one 9 is generally purified using well known procedures, such as recrystallization and/or chromatography.

Alternatively, 5-amino-7-alkyl-5,7-dihydro-6H-dibenz[b, d]azepin-6-ones, 9, can be prepared by first forming the 5-iodo derivative 10 of 5,7-dihydro-6H-dibenz[b,d]azepin-6-one, 6. This reaction is typically conducted as described in A. O. King et al.[10] by treating 6 with an excess, preferably about 1.2 to about 2.5 equivalents, of trimethylsilyl iodide in the presence of an excess of a trialkyamine, such as triethylamine, diisopropylethylamine, TMEDA and the like, at a temperature ranging from about −20° C. to about 0° C. for about 3 to 30 minutes and then adding about 1.1 to about 2.0 equivalents of iodine ($I_2$). Typically, after addition of the iodide, the reaction is stirred at a temperature ranging from about 0° C. to about 20° C. for about 2 to about 4 hours to afford 5-iodo-5,7-dihydro-6H-dibenz[b,d]azepin-6-one, 10.

Displacement of iodide from 10 using an alkali metal azide then affords 5-azido-5,7-dihydro-6H-dibenz[b,d] azepin-6-one, 11. Typically, this reaction is conducted by contacting 10 with about 1.1 to about 1.5 equivalents of sodium azide in an inert diluent, such as DMF, at a temperature ranging from about 0° C. to about 50° C. for about 12 to about 48 hours.

The azido derivative 11 is then reduced to the corresponding amino derivative 12 using conventional procedures and reagents. For example, the azido group is preferably reduced by contacting 11 with an excess, preferably with about 3 eqvalents, of triphenylphosphine in a diluent, preferably a mixture of THF and water. This reduction reaction is typically conducted at a temperature ranging from about 0° C. to about 50° C. for about 12 to 48 hours to afford 5-amino-5,7-dihydro-6H-dibenz[b,d]azepin-6-one, 12.

The amino group of 12 is then protected or blocked using a conventional amino blocking group. Preferably, compound 12 is treated with about 1.0 to about 1.1 equivalents of di-ter-butyl dicarbonate in the presence of an excess, preferably about 2 to about 3 equivalents, of a trialkylamine, such as triethylamine. This reaction is typically conducted in an inert diluent, such as THF, at a temperature ranging from about 0° C. to about 50° C. for 3 to about 24 hours to provide 5-(N-Boc-amino)-5,7-dihydro-6H-dibenz[b,d]azepin-6-one, 13.

Compound 13 is then optionally N-alkylated to afford, after de-blocking of the amino group, a 5-amino-7-alkyl-5, 7-dihydro-6H-dibenz[b,d]azepin-6-one, 9.

Representative alkyl, substituted alkyl and cycloalkyl halides suitable for use in this N-alkylation reaction include, by way of illustration, 1-iodo-2-methylpropane, methyl bromoacetate, 1-chloro-3,3-dimethyl-2-butanone, 1-chloro-4-phenylbutane, bromomethylcyclopropane, 1-bromo-2,2, 2-trifluoroethane, bromocyclohexane, 1-bromohexane and the like.

The N-Boc protecting group is then removed using conventional procedures and reagents to afford the 5-amino-7-alkyl-5,$7_1$-dihydro-6H-dibenz[b,d]azepin-6-one, 9. This deblocking reaction is typically conducted by treating the N-Boc compound 13 with anhydrous hydrogen chloride in an inert diluent, such as 1,4-dioxane, at a temperature ranging from about 0° C. to about 50° C. for about 2 to about 8 hours. The resulting 5-amino-7-alkyl-5,7-dihydro-6H-dibenz[b,d]azepin-6-one 9 is generally purified using well known procedures, such as recrystallization and/or chromatography.

The 5-amino-7-alkyl-5,7-dihydro-6H-dibenz[b,d]azepin-6-ones, 9, can also be prepared via an azide transfer reaction as illustrated in Scheme 3.

Scheme 3

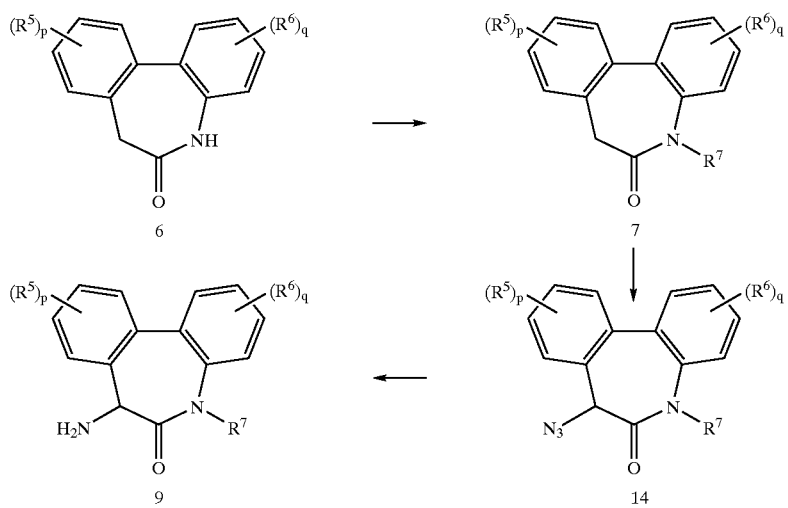

As shown in Scheme 3, 5,7-dihydro-6H-dibenz[b,d]azepin-6-one, 6, is first N-alkylated as described above using conventional reagents and conditions to provide a 7-alkyl-5,7-dihydro-6H-dibenz[b,d]azepin-6-one derivative, 7.

The 7-alkyl-5,7-dihydro-6H-dibenz[b,d]azepin-6-one 7 is then reacted with an azide transfer reagent to afford 5-azido-7-alkyl-5,7-dihydro-6H-dibenz[b,d]azepin-6-one 14. Typically, this reaction is conducted by first contacting 7 with an excess, preferably with about 1.0 to 1.5 equivalents of a suitable base, such as lithium diisopropylamine and the like, in an inert diluent such as THF, at a temperature ranging from about −90° C. to about −60° C. for about 0.25 to about 2.0 hours. The resulting anion is then treated with an excess, preferably with about 1.1 to about 1.2 equivalents, of an azide transfer reagent, such as 2,4,6-triisopropylbenzenesulfonyl azide (trisyl azide). This reaction is typically conducted at a temperature ranging from about −90° C. to about −60° C. for about 0.25 to about 2.0 hours. The reaction mixture is then typically treated with an excess of glacial acetic acid and the mixture is allowed to warm to ambient temperature and then heated at about 35° C. to about 50° C. for about 2 to 4 hours to afford the 5-azido-7-alkyl-5,7-dihydro-6H-dibenz[b,d]azepin-6-one derivative 14. Reduction of 14 as described above using conventional reagents and conditions then affords the 5-amino-7-alkyl-5,7-dihydro-6H-dibenz[b,d]azepin-6-one 9.

If desired, the aryl rings of 5-amino-7-alkyl-5,7-dihydro-6H-dibenz[b,d]azepin-6-ones, 9, and related compounds may be partially or fully saturated by treatment with hydrogen in the presence of a hydrogention catalyst. Typically, this reaction is conducted by treating 9 with hydrogen at a pressure of about 10 to about 100 psi in the presence of a catalyst, such as rhodium on carbon. This reaction is typically conducted at a temperature ranging from about 20° C. to about 100° C. for about 12 to 96 hours in a suitable diluent, such as ethyl acetate/acetic acid (1:1) and the like.

After preparing the polycyclic α-amino-ε-caprolactam, the a-amino group may be coupled with a monopeptide derivative (i.e., an amino acid derivative) to prepared compounds of formula I, wherein n is 1. Scheme 4 illustrates the coupling of a representative polycyclic α-amino-ε-caprolactam, i.e., 9, with a monopeptide derivative 15, wherein $R^2$ and n are as defined above and $R^{1'}$ is an amino-blocking group.

Scheme 4

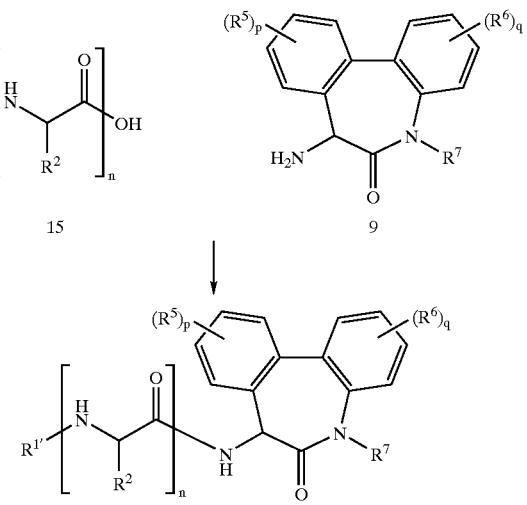

As illustrated in Scheme 4, the coupling of 5-amino-7-alkyl-5,7-dihydro-6H-dibenz[b,d]azepin-6-ones, 9, with a monopeptide 15 affords the amide 16. This reaction is typically conducted by reacting at least a stoichiometric amount of the amino compound 9 and the monopeptide 15 with a standard coupling reagent, typically in the presence of a trialkylamine, such as ethyldiisopropylamine, under conventional coupling reaction conditions. Optionally, well-known coupling promoters, such N-hydrixysuccinimide, 1-hydroxybenzotriazole and the like, may be employed in this reaction. Typically, this coupling reaction is conducted at a temperature ranging from about 0° C. to about 60° C. for about 1 to about 72 hours in an inert diluent, such as THF, to afford the amide 16.

Suitable coupling reagents include, by way of example, carbodiimides, such as ethyl-3-(3-dimethylamino)propylcarboiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP) and the like. The coupling reagent may also be bound to a solid support. For example, a polymer supported form of EDC is described in *Tetrahedron Letters* 1993, 34(48), 7685.[11] Additionally, 1-(3-(1-pyrrolidinyl)propyl-3-ethylcarbodiimide (PEPC) and its corresponding polymer supported forms may be used as a coupling reagent. Briefly, PEPC can be prepared by first reacting ethyl isocyanate with 1-(3-aminopropyl)pyrrolidine. The resulting urea is treated with 4-toluenesulfonyl chloride to provide PEPC. The polymer supported form is prepared by reacting PEPC with an appropriate resin, such as chloromethylated styrene/divinylbenzene resins (Merrifield's resins) under standard conditions to give the desired reagent. Such methods are described more fully in U.S. Provisional Application Ser. No. 60/019,790, filed Jun. 14, 1996,[12] which application is incorporated herein by reference in its entirety.

The monopeptide derivatives employed in the coupling reaction are commercially available or can be prepared using conventional procedures and reagents from commercially available starting materials. The monopeptide derivatives may be derived from naturally-occurring and non-natural amino acids. For example, suitable monopeptide derivatives (i.e., amino acid derivatives) include, by way of illustration, N-Boc-glycine, N-Boc-L-alanine, N-Boc-L-valine, N-Boc-L-leucine, N-Boc-L-isoleucine, N-Boc-tert-L-leucine, N-Boc-L-methionine, N-Boc-L-phenylalanine, N-Boc-L-phenylglycine, N-Boc-L-aspartic acid β-tert-butyl ester, N-Boc-L-glutamic acid β-tert-butyl ester, N-Boc-Nε-Cbz-L-lysine, N-Boc-norleucine and the like.

After forming amide 16, the amino-blocking group $R^{1'}$, is typically removed to reestablish the amino group. For example, when $R^{1'}$ is a tert-butoxycarbonyl group, the N-Boc group can be removed by treating 16 with anhydrous hydrogen chloride in an inert diluent, such as 1,4-dioxane. This reaction is typically conducted at a temperature ranging from about −10° C. to about 15° C. while hydrogen chloride gas is introduced into the reaction mixture, and then at a temperature ranging from about 10° C. to about 60° C. for about 1 to about 24 hours. Other amino-blocking groups can be removed using well-known art recognized procedures.

The substituted 1,5-diazepine compounds of this invention can be prepared as shown, for example, in Scheme 5. As illustrated in Scheme 5, a β-keto ester, 17,where $R^8$ is as defined herein and R is typically alkyl, such as methyl, ethyl and the like, is condensed with a 1,2-phenylenediamine, 18, where $R^5$ and p are as defined herein, to afford 1,3-dihydro-1,5-benzodiazepin-2-one 19. This reaction is typically conducted by contacting 18 with an excess of 17 in an inert solvent, such as toluene, at a temperature ranging from about 50° C. to about 100° C. for about 2 to about 24 hours. Preferably, the water generated during the reaction is removed, for example, by using a Dean-Stark trap.

The 1,3-dihydro-1,5-benzodiazepin-2-one, 19, is then readily alkylated using conventional reagents and reaction conditions. The N-alkylation reaction is typically conducted by treating 19 with about 1.0 to 1.5 equivalents of an alkyl halide, a substituted alkyl halide or a cycloalkyl halide in the presence of about 1.0 to about 1.5 equivalents of a suitable base, such as cesium carbonate and the like. This reaction is generally conducted in an inert diluent, such as DMF and the like, at a temperature ranging from about 25° C. to about 100° C. for about 12 to about 48 hours to afford 20.

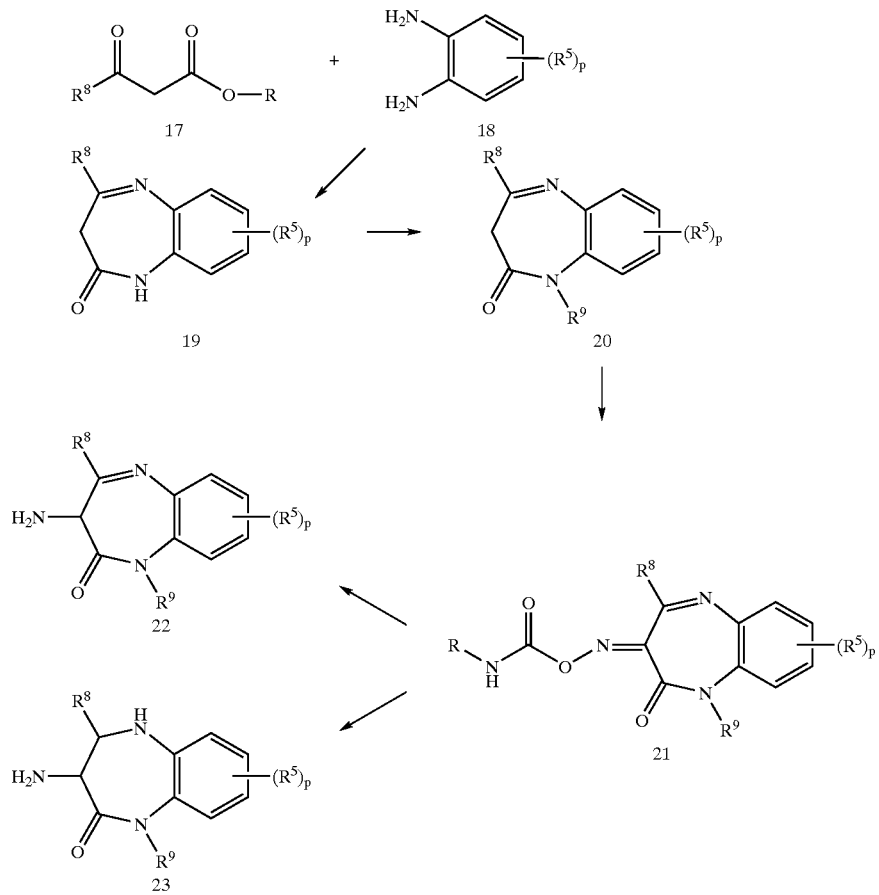

The intermediate 20 is then oximated by contacting 20 with an excess, preferable with about 1.0 to 1.5 equivalents of a suitable base, such as potassium tert-butoxide and the like, in the presence of about 1.0 to about 2.0 equivalents of an alkyl nitrile. Suitable alkyl nitrites for use in this reaction include, by way of example, butyl nitrite, isoamyl nitrite and the like. This reaction is typically conducted in an inert diluent, such as toluene and the like, at a temperature ranging from about −20° C. to about 20° C. for about 0.5 to about 6 hours to afford the corresponding 3-oximo derivative. The oxime group is then reacted with an isocyanate to afford intermediate 21. This reaction is typically conducted by contacting the oxime derivative with about 1.0 to about 2.0 equivalents of an alkyl isocyanate, such as ethyl isocyanate, in the presence of an amine, such as triethylamine. This reaction is typically conducted in an inert diluent, such as dichloromethane and the like, at ambient temperature for about 6 to about 24 hours to afford intermediate 21.

Reduction of intermediate 21 using, for example, zinc dust in glacial acetic acid then provides 3-amino-1,3-dihydro-1,5-benzodiazepin-2-one 22. This reaction is typically conducted at ambient temperature for about 0.5 to about 6 hours. Alternatively, intermediate 21 can be reduced with hydrogen using a catalyst, such as palladium on carbon, to afford 3-amino-1,3,4,5-tetrahydro-1,5-benzodiazepin-2-one 23. Typically, this reaction is conducted at ambient temperature for about 12 to about 48 hours. If desired, compounds 22 and 23 can then be coupled with an amino acid derivative using the procedures described herein.

Other methods for preparing the substituted 1,5-diazepines of this inventions are described in the Examples below.

As will be apparent to those skilled in the art, the polycyclic α-amino-ε-caprolactams and related compounds of this invention may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the polycyclic α-amino-ε-caprolactams of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Utility

The compounds of the invention are useful as synthetic intermediates in the preparation of inhibitors of β-amyloid peptide release and/or its synthesis. Accordingly, the intermediates of this inventions have utility in the preparation of compounds which are useful, for example, for diagnosing and treating Alzheimer's disease in mammals, including humans.

For example, the use of various compounds of this invention in the preparation of inhibitors of β-amyloid peptide release and/or its synthesis is described in U.S. patent application Ser. No. 08/996,422, filed Dec. 19, 1997, [13] the disclosure of which is incorporated herein by reference in its entirety.

The following synthetic and biological examples are offered to illustrate this invention and are not to be construed in any way as limiting the scope of this invention.

EXAMPLES

In the examples below, the following abbreviations have the following meanings, unless otherwise indicated. All other abbreviations have their generally accepted meaning.

| | |
|---|---|
| BEMP = | 2-tert-butylimino-2-diethylamino-1,3-dimethylperhydro-1,3,2-diazaphosphorine |
| Boc = | tert-butoxycarbonyl |
| BOP = | benzotriazol-1-yloxy-tris-(dimethylamino)phosphonium hexafluorophosphate |
| bd = | broad doublet (spectral) |
| bs = | broad singlet (spectral) |
| ° C. = | degrees Celsius |
| calcd = | calculated |
| δ = | chemical shift in parts per million downfield from tetramethylsilane |
| d = | doublet (spectral) |
| dd = | doublet of doublets (spectral) |
| DIC = | diisopropylcarbodiimide |
| DIPEA = | diisopropylethylamine |
| DMF = | dimethylformamide |
| DMAP = | dimethylaminopyridine |
| DMSO = | dimethyl sulfoxide |
| EDC = | ethyl-1-(3-dimethyaminopropyl)carbodiimide |
| ee = | enantiomeric excess |
| eq. = | equivalents |
| Et = | ethyl |
| EtOAc = | ethyl acetate |
| g = | gram(s) |
| h = | hour(s) |
| HMDS = | 1,1,1,3,3,3-hexamethyldisilazane or bis(trimethylsilyl)amine |
| HOAc = | acetic acid |
| HOBt = | 1-hydroxybenzotriazole hydrate |
| HPLC = | high-performance liquid chromatography |
| Hunig's base = | diisopropylethylamine |
| IPA = | isopropyl alcohol |
| L = | liter |
| m = | multiplet (spectral) |
| M = | moles per liter |
| max = | maximum |
| Me = | methyl |
| meq = | milliequivalent |
| mg = | milligram |
| mL = | milliliter |
| mm = | millimeter |
| mmol = | millimole |
| MW = | molecular weight |
| N = | normal |
| ng = | nanogram |
| nm = | nanometers |
| NMR = | nuclear magnetic resonance |
| OD = | optical density |
| PEPC = | 1-(3-(1-pyrrolidinyl)propyl)-3-ethylcarbodiimide |
| PP-HOBT = | piperidine-piperidine-1-hydroxybenzotrizole |
| psi = | pounds per square inch |
| φ = | phenyl |
| q = | quartet (spectral) |
| quint. = | quintet (spectral) |
| rpm = | rotations per minute |
| s = | singlet (spectral) |
| t = | triplet (spectral) |
| TFA = | trifluoroacetic acid |
| THF = | tetrahydrofuran |
| tlc or TLC = | thin layer chromatography |
| μL = | microliter |
| UV = | ultraviolet |

Additionally, the following abbreviations are used to indicate the commercial source for certain compounds and reagents:

| | |
|---|---|
| Aldrich = | Aldrich Chemical Company, Inc., 1001 West Saint Paul Avenue, Milwaukee, WI 53233 USA |
| Fluka = | Fluka Chemical Corp., 980 South 2nd Street, Ronkonkoma NY 11779 USA |
| Lancaster = | Lancaster Synthesis, Inc., P.O. Box 100 Windham, NH 03087 USA |
| Sigma = | Sigma, P.O. Box 14508, St. Louis MO 63178 USA |
| Bachem = | Bachem Biosciences Inc., 3700 Horizon Drive, Renaissance at Gulph Mills, King of Prussia, PA 19406 USA |
| Novabiochem = | Calbiochem-Novabiochem Corp. 10933 North Torrey Pines Road, P.O. Box 12087, La Jolla CA 92039-2087 |

In the examples below, all temperatures are in degrees Celsius (unless otherwise indicated). The following General Procedures were used as indicated to prepare the compounds set forth in the examples below.

GENERAL PROCEDURE A

Preparation of 5-Amino-7-alkyl-5,7-dihydro-6H-dibenz[b,d]azepin-6-one Derivative Step A: To a stirred solution of 5,7-dihydro-6H-dibenz[b,d]azepin-6-one (30 mmol) in DMF (150 mL) was added in portions 97% NaH (1.08 g, 45 mmol) Bubbling occurred immediately and was followed by heavy precipitation. After 10 min., an alkyl halide (33 mmol) was added. The precipitate dissolved quickly and in about 10 min. a clear solution was obtained. The reaction mixture was stirred overnight and then evaporated as completely as possible on a rotovap at 30° C. Ethyl acetate (100 mL) was added to the residue and this mixture was washed with water, brine, and dried over magnesium sulfate. After filtration and concentration, the residue was typically chromatographed to provide the 7-alkyl-5,7-dihydro-6H-dibenz[b,d]azepin-6-one.

Step B: The 7-alkyl-5,7-dihydro-6H-dibenz[b,d]azepin-6-one (1 eq.) from Step A was dissolved in THF and isoamylnitrite (1.2 eq.) was added. The mixture was cooled to 0° C. in an ice bath. NAHMDS (1.1 eq., 1M in THF) was added dropwise. After stirring for 1 hour or until the reaction was complete, the mixture was concentrated then acidified with 1N HCl and extracted with EtOAc. The organic portion was dried and concentrated to yield a crude product which was purified by silica gel chromatography.

Step C: The resulting oxime from Step B was dissolved in EtOH/NH$_3$ (20:1) and hydrogenated in a bomb using Raney nickel and hydrogen (500 psi) at 100° C. for 10 hours. The resulting mixture was filtered and concentrated to provide a crude product which was purified by silica gel chromatography to yield the title compound.

GENERAL PROCEDURE B

Preparation of Fluoro-Substituted 5,7-Dihydro-6H-dibenz[d,b]azepin-6-Derivatives A modification of the procedure of Robin D. Clark and Jahangir, Tetrahedron 1993, 49(7), 1351–1356[14] was used. Specifically, an appropriately substituted N-Boc-2-amino-2'-methylbiphenyl was dissolved in THF and cooled to −78° C. sec-Butyllithium (1.3M in cyclohexane, 2.2 eq.) was added slowly so that the temperature remained below −65° C. The resulting mixture was allowed to warm to −25° C. and was stirred at that temperature for 1 hour. The mixture was cooled to −78° C. Dry $CO_2$ was bubbled through the mixture for 30 seconds. The mixture was allowed to warm to ambient temperature then was carefully quenched with water. The mixture was concentrated under reduced pressure then was adjusted to pH 3 with 1N HCl. The mixture was extracted with EtOAc and the organic portion was dried and concentrated to yield a crude material. The crude material was dissolved in methanol and the solution was saturated with HCl. The mixture was heated at reflux for 12 hours then was allowed to cool. The mixture was concentrated to provide crude lactam which was purified by chromatography or crystallization.

GENERAL PROCEDURE C

Resolution of 5-Amino-7-methyl-5,7-dihydro-6H-dibenz-[b,d]azepin-6-one

In a round bottom flask was added the racemic freebase amine (1.0 eq.) in methanol followed by di-p-toluoyl-D-tartaric acid monohydrate (1.0 eq.). The mixture was concentrated in vacuo to a residue and redissolved in a moderate volume of methanol and allowed to stir at room temperature open to the atmosphere (8–72 hours). The solid was removed by filtration. The enantiomeric excess was determined by chiral HPLC (Chiracel ODR) using 15% acetonitrile and 85% $H_2O$ with 0.1% trifluoroacetic acid and a flow rate of 1.0 mL/min at 35° C. The resolved di-p-toluoyl-D-tartaric salt was then dissolved in EtOAc and saturated $NaHCO_3$ until pH 9–10 was reached. The layers were separated and the organic layer was washed again with saturated $NaHCO_3$, $H_2O$, and brine. The organic layer was dried over $MgSO_4$ and the drying agent was removed by filtration. The filtrate was concentrated in vacuo. The free amine was dissolved in MeOH and HCl (12M, 1.0 eq.) was added. The salt was concentrated in vacuo and the resulting film was triturated with EtOAc. The HCl salt was filtered and rinsed with EtOAc. The ee was determined by chiral HPLC. This General Procedure can also be used to resolve other 5-amino-7-alkyl-5,7-dihydro-6H-dibenz[b,d]azepin-6-ones.

GENERAL PROCEDURE D

EDC Coupling Procedure

A round bottom flask was charged with a carboxylic acid (1.0 eq.), hydroxybenzotriazole hydrate (1.1 eq.) and an amine (1.0 eq.) in THF under nitrogen atmosphere. An appropriate amount (1.1 eq for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in ethyl acetate (or similar solvent) and water, washed with saturated aqueous sodium bicarbonate solution, 1N HCl, brine, dried over anhydrous sodium sulfate and the solvent removed at reduced pressure to provide the product.

GENERAL PROCEDURE E

N-Boc Removal Procedure

A stream of anhydrous HCl gas was passed through a stirred solution of the N-Boc compound in 1,4-dioxane (0.03–0.09 M), chilled in a ice bath to ~10° C. under $N_2$, for 10–15 minutes. The cooling bath removed and the solution was allowed to warm to room temperature with stirring for 2–24 hours, monitoring by TLC for the consumption of starting material. The solution was concentrated (and in some instances dissolved in $CH_2Cl_2$ then re-concentrated and placed in vacuum oven at 60–70° C. to remove most of the residual dioxane). The residue was typically used without further purification.

GENERAL PROCEDURE F

Reduction of Pyridines and Subsequent Acylation

Step A—Reduction of Pyridines

A substituted pyridine hydrochloride was dissolved in ethanol. Rhodium on alumina was added and the mixture was shaken under 60 psi atmosphere of hydrogen at 40° C. for 6 to 18 hours. The mixture was filtered and concentrated to provide a crude product used in Step B.

Step B—Acylation of Piperidines

The crude product from Step A was vigorously stirred in a mixture of chloroform and saturated aqueous sodium bicarbonate. Chloroacetyl chloride (about 1.1 equivalents) was added dropwise. The resulting mixture was stirred for one hour. The organic portion was separated, dried and concentrated to provide a crude product which was purified by silica gel chromatography.

GENERAL PROCEDURE G

Fridel-Crafts Alkylation

An appropriately substituted chloroacetamide (1 equivalent) and aluminum trichloride (2.4 equivalents) were stirred in o-dichlorobenzene. The mixture was heated to between 150° C. and the refluxing temperature for between one and four hours. The mixture was allowed to cool and then was poured onto ice. The mixture was extracted with methylene chloride and the organic portion was dried and concentrated to yield a crude product which was purified either by crystallization or by chromatography.

GENERAL PROCEDURE H

Azide Transfer

The lactam starting material was dissolved in THF and the stirred solution was cooled to −78° C. An appropriate base, such as lithium diisopropylamine (1.1 eq.), was slowly added. The mixture was stirred for 30 minutes. A solution of trisyl azide (1.1 eq.) in THF was added dropwise. The resulting mixture was stirred at −78° C. for 30 minutes. Glacial acetic acid (4.2 eq.) was added and the mixture was allowed to warm to room temperature. The mixture was heated to 40° C. and stirred at that temperature for between 2 and 4 hours. Water was added and the mixture was extracted with ethyl acetate. The organic portion was dried and concentrated to provide a crude product which was purified by silica gel chromatography.

GENERAL PROCEDURE I

Azide Reduction

The azide starting material (1 eq.) was dissolved in 4% water/THF. Triphenylphosphine (2.8 eq.) was added and the mixture was stirred at ambient temperature for 16 hours. The mixture was extracted with dilute aqueous hydrochloric acid. The aqueous portion was washed with ether and then adjusted to pH 9–10 with aqueous sodium hydroxide. The mixture was extracted with methylene chloride. The organic portion was dried and concentrated to provide the crude amine which was purified by silica gel chromatography.

GENERAL PROCEDURE J

N-Alkylation Using Cesium Carbonate

To a solution of the lactam in DMF was added cesium carbonate (1.05 eq) and an alkyl iodide (1.1 eq). The mixture was allowed to stir overnight at room temperature and then the reaction mixture was diluted with ethyl acetate and washed with water, followed by brine. The organic layer was dried over sodium sulfate, filtered and concentrated under reduced pressure. The residue was purified by HPLC (LC 2000), eluting with an ethyl acetate/hexane system.

GENERAL PROCEDURE K

EDC Coupling Procedure

To a solution or suspension of the amine or amine hydrochloride (1.0 eq.) in THF (0.05–0.1 M) under $N_2$ at 0° C. was added the carboxylic acid (1.0–1.1 eq.), hydroxybenzotriazole monohydrate (1.1–1.15 eq.), Hunig's base (1.1 eq. for free amines and 1.1–2.3 eq. for hydrochloride amine salts), followed by 1-(3-dimethylaminopropyl)-3-ethylcarbodiimide hydrochloride (1.1–1.15 eq.). The cooling bath was removed and the mixture allowed to warm to room temperature for 10–24 hours. The solution or mixture was diluted with EtOAc, in a 3–5 volume multiple of the initial THF volume, and washed with 0.1–1.0 M aq. HCl (1 or 2x), dilute $NaHCO_3$ (1 or 2x), and brine (1x). Then, the organic phase was dried over either $MgSO_4$ or $Na_2SO_4$, filtered, concentrated to provide the crude product, which was either further purified or utilized without further purification.

GENERAL PROCEDURE L

EEDQ Coupling Procedure

To a solution of the amine in THF (1.0 eq., 0.05–0.08 M, final molarity) under $N_2$ at room temperature was added the N-t-Boc protected amino acid (1.1 eq., either as a solid or in THF via cannula), followed by EEDQ (Aldrich, 1.1 eq.). The pale yellow solution was stirred at room temperature for 16–16.5 hours, then diluted with EtOAc (in a 3–5 volume multiple of the initial THF volume), and washed with 1M aq. HCl (2x), dilute aq. $NaHCO_3$ (2x), and brine (1x). The organic phase was dried over either $Na2SO_4$ or $MgSO_4$, filtered, and concentrated.

Example 1

Synthesis of 5-Amino-7-methyl-5,7-dihydro-6H-dibenz[b,d]azepin-6-one Hydrochloride Step A—Synthesis of 7-Methyl-5,7-dihydro-6H-dibenz[b,d]azepin-6-one A round bottom flask was charged with sodium hydride (0.295 g, 7.46 mmol) in 9.0 mL of DMF and treated with 5,7-dihydro-6H-dibenz[b,d]azepin-6-one (1.3 g, 6.22 mmol) (CAS # 20011-90-9, prepared as described in R. F. C. Brown, et. al., *Tetrahedron Letters* 1971, 8, 667–670[9] and references cited therein). After stirring at 60° C. for 1 h, the solution was treated with methyl iodide (1.16 mL, 18.6 mmol) and stirring continued for 17 h with the exclusion of light. After cooling, the reaction was diluted with $CH_2Cl_2$/$H_2O$, washed with $NaHSO_4$ solution, $H_2O$, and dried over $Na_2SO_4$. Evaporation and flash chromatography ($SiO_2$, $CHCl_3$) gave 0.885 g (63%) of the title compound as a colorless solid.

Physical data were as follows:
$^1$H-NMR (CDCl$_3$): δ=7.62 (d, 2H), 7.26–7.47 (m, 6H), 3.51 (m, 2H), 3.32 (s, 3H).
C$_{15}$H$_{13}$NO (MW=223.27); mass spectroscopy (MH+) 223.
Anal. Calcd for C$_{15}$H$_{13}$NO; C, 80.69 H, 5.87 N, 6.27. Found: C, 80.11 H, 5.95 N, 6.23.

Step B—Synthesis of 7-Methyl-5-oximo-5,7-dihydro-6H-dibenz[b,d]azepin-6-one

The product from Step A (0.700 g, 3.14 mmol) was dissolved in 20 mL of toluene and treated with butyl nitrite (0.733 mL, 6.28 mmol). The reaction temperature was lowered to 0° C. and the solution was treated with KHMDS (9.42 mL, 0.5 M) under N$_2$ atmosphere. After stirring for 1 h the reaction was quenched with a saturated solution of NaHSO$_4$, diluted with CH$_2$Cl$_2$ and separated. The organic layer was dried over Na$_2$SO$_4$ and the title compound purified by chromatography (SiO$_2$, 98:2 CHCl$_3$/MeOH) giving 0.59 g (80%) as a colorless solid.

Physical data were as follows:
C$_{15}$H$_{12}$N$_2$O$_2$ (MW=252.275); mass spectroscopy (MH+) 252.
Anal. Calcd for C$_{15}$H$_{12}$N$_2$O$_2$; C, 71.42 H, 4.79 N, 11.10. Found: C, 71.24 H, 4.69 N, 10.87.

Step C—Synthesis of 5-Amino-7-Methyl-5,7-dihydro-6H-dibenz[b,d]azepin-6-one Hydrochloride The product from Step B (0.99 g, 3.92 mmol) was hydrogenated in a Parr apparatus at 35 psi over 10% Pd/C (0.46 g) in 3A ethanol. After 32 h the reaction mixture was filtered through a plug of Celite, the filtrate evaporated to a foam and treated with a saturated solution of HCl(g) in Et$_2$O. The resulting colorless solid was filtered, rinsed with cold Et$_2$O and vacuum dried to give 0.66 g (61%) of the title compound.

Physical data were as follows:
$_1$H-NMR (DMSO-d$_6$): δ=9.11 (bs, 3H), 7.78–7.41 (m, 8H), 4.83 (s, 1H), 3.25 (s, 3H).
C$_{15}$H$_{14}$N$_2$O.HCl (MW=274.753); mass spectroscopy (MH+free base) 238.
Anal. Calcd for C$_{15}$H$_{14}$N$_2$O.HCl; C, 65.57 H, 5.50 N, 10.19 Found: C, 65.27 H, 5.67 N, 10.13.

Example 2

Synthesis of 5-(S)-Amino-7-methyl-5,7-dihydro-6H-dibenz[b,d]azepin-6-one Hydrochloride Following General Procedure C using racemic 5-amino-7-methyl-5,7-dihydro-6H-dibenz[b,d]azepin-6-one (1.0 eq.) and di-p-toluoyl-D-tartaric acid monohydrate (1.0 eq.) in methanol, the title compound was prepared as a solid. The product was collected by filtration. Enantiomeric excess was determined by chiral HPLC.]

Physical data were as follows:
Enantiomer 1: Retention time=9.97 minutes.
Enantiomer 2: Retention time=8.62 minutes.
NMR data was as follows:
$^1$H-NMR (CDCl$_3$): δ=9.39 (s, 2H), 7.75–7.42 (m, 8H), 4.80 (s, 1H), 3.30 (s, 3H).
C$_{15}$H$_{15}$ClN$_2$O (MW=274.75); mass spectroscopy (MH$^+$) 239.1.
Anal Calcd for C$_{15}$H$_{15}$ClN$_2$O$_3$; C, 65.57; H, 5.50; N, 10.20; Found: C, 65.51, H, 5.61; N, 10.01.

Example 3

Synthesis of 5-(N-Boc-Amino)-5,7-dihydro-6H,7H-dibenz[b,d]azepin-6-one

Step A—Synthesis of 5-Iodo-5,7-dihydro-6H-dibenz[b,d]azepin-6-one

A solution of 5,7-dihydro-6H-dibenz[b,d]azepin-6-one (1.0 g, 4.77 mmol) (prepared as described in R. F. C. Brown, et. al., *Tetrahedron Letters* 1971, 8, 667–670[9] and references cited therein) and Et$_3$N (2.66 mL, 19.12 mmol) were stirred for 5.0 minutes at −15° C. in CH$_2$Cl$_2$ and treated with TMSI (1.36 mL, 9.54 mmol). After stirring for 15 minutes, I$_2$ (1.81 g, 7.16 mmol) was added in a single portion and the reaction allowed to warm to 5–10° C. over 3 h. The reaction was quenched with sat. Na$_2$SO$_3$, diluted with CH$_2$Cl$_2$ and separated. The organics were washed with Na$_2$SO$_3$ and NaHSO$_3$ and dried over MgSO$_4$. After filtration, the organics were concentrated to approximately 20 mL and diluted with an additional 20 mL of hexanes. The title compound was isolated as a tan precipitate by filtration or could be chromatographed (SiO$_2$, CHCl$_3$/MeOH, 99:1) to provide a yellow solid.

Physical data were as follows:
$^1$H-nmr (CDCl$_3$): δ=8.05 (bs, 1H), 7.64–7.58 (m, 2H), 7.52–7.45 (m, 2H), 7.38–7.32 (m, 3H), 7.11 (d, 1H), 5.79 (s, 1H).
C$_{14}$H$_{10}$INO (MW=335.139); mass spectroscopy (MH+) 336.
Anal. Calcd for C$_{14}$H$_{10}$INO; C, 50.17 H, 3.01 N, 4.18. Found: C, 49.97 H, 3.01 N, 4.06.

Step B—Synthesis of 5-Azido-5,7-dihydro-6H-dibenz[b,d]azepin-6-one

The product from Step A was dissolved in DMF and treated with 1.2 equivalents of NaN$_3$. After stirring 17 h at 23° C., the mixture was diluted with EtOAc/H$_2$O, separated, washed with brine and dried over MgSO$_4$. Trituration from hot EtOAc provided the title compound as a tan powder.

Physical data were as follows:
$^1$H-nmr (DMSO-d$_6$): δ=10.51 (s, 1H), 7.72 (m, 1H), 7.63 (m, 1H), 7.48 (m, 4H), 7.30 (m, 1H), 7.24 (m, 1H) 5.27 (s, 1H).
C$_{14}$H$_{10}$N$_4$O(MW=250.13); mass spectroscopy (MH+) 251.

Step C—Synthesis of 5-(N-Boc-Amino)-5,7-dihydro-6H,7H-dibenz[b,d]azepin-6-one

The product from Step B was dissolved in THF/H$_2$O and stirred at 23° C. for 17 h in the presence of 3.0 equivalents of Ph$_3$P. The reaction was diluted with 50% HOAc/toluene, separated, the aqueous layer extracted with toluene and evaporated to an oily residue. The pH of the residue was adjusted to pH 7.0 by the addition of 1N NaOH and the resulting HOAc salt was collected and vacuum dried. This salt was treated with di-tert-butyl dicarbonate (1.05 equivalents) (Aldrich) and Et$_3$N (2.1 equivalents) in THF. After stirring for 5 h at 23° C., the reaction was filtered and the title compound was isolated as a colorless powder.

Physical data were as follows:
$^1$H-nmr (CDCl$_3$): δ=7.69–7.31 (m, 8H), 7.11 (m, 1H), 6.22 (m, 1H), 5.12 (m, 1H), 1.47 (s, 9H).
C$_{19}$H$_{20}$N$_2$O$_3$ (MW=324.16); mass spectroscopy (MH+) 325.

Example 4

Synthesis of 5-Amino-7-(2-methylpropyl)-5,7-dihydro-6H-dibenz[b,d]azepin-6-one Hydrochloride Step A—Synthesis of 5-(N-Boc-Amino)-7-(2-methylpropyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 3) in DMF was treated with $Cs_2CO_3$ (0.22 g, 0.678 mmol) and warmed to 60° C. To the reaction mixture was added 1-iodo-2-methylpropane (0.078 mL, 0.678 mmol) and stirring continued for 17 h. After cooling to 23° C., the mixture was diluted with $CH_2Cl_2$, washed with several portions of brine and dried over $Na_2SO_4$. The title compound was purified by chromatography ($SiO_2$, $CHCl_3$/MeOH 9:1).

Physical data were as follows:

$C_{23}H_{28}N_2O_3$ (MW=380.41); mass spectroscopy (MH+) 381.

Anal. Calcd for $C_{23}H_{28}N_2O_3$; C, 72.61 H, 7.42 N, 7.36. Found: C, 72.31 H, 7.64 N, 7.17.

Step B—Synthesis of 5-Amino-7-(2-methylpropyl)-5,7-dihydro-6H-dibenz[b,d]azepin-6-one Hydrochloride The product from Step A was deprotected using General Procedure E to provide the title compound as a slightly colored solid after neutralization and extraction with ethyl acetate, drying over $Na_2SO_4$ and vacuum drying.

Physical data were as follows:

$^1$H-nmr ($CDCl_3$): δ=7.63–7.31 (m, 8H), 4.35 (bs, 1H), 4.27 (m, 1H), 3.30 (m, 1H), 2.02 (bs, 2H), 0.55 (d, 3H), 0.29 (d, 3H).

$C_{18}H_{20}N_2O$ (MW=280.17); mass spectroscopy (MH+) 281.

Example 5

Synthesis of 5-Amino-7-(methoxycarbonylmethyl)-5,7-dihydro-6H-dibenz[b,d]azepin-6-one Hydrochloride Step A—Synthesis of 5-(N-Boc-Amino)-7-(methoxycarbonylmethyl)-5,7-dihydro-6H-dibenz[b,d]azepin-6-one A solution of 5-(N-Boc-amino)-5,7-dihydro-6H-dibenz[b,d]azepin-6-one (1.03, 3.08 mmol) (Example 3) in DMF was treated with $Cs_2CO_3$ (1.10 g, 3.39 mmol) and warmed to 60° C. To this reaction mixture was added methyl bromoacetate (0.321 mL, 3.39 mmol) (Aldrich) and stirring was continued for 17 h. After cooling to 23° C., the mixture was diluted with $CH_2Cl_2$, washed with several portions of brine and dried over $Na_2SO_4$. The title compound was purified by chromatography ($SiO_2$, $CHCl_3$).

Physical data were as follows:

$C_{22}H_{24}N_2O_5$ (MW=396.44); mass spectroscopy (MH+) 397

Anal. Calcd for $C_{22}H_{24}N_2O_5$; C, 66.65 H, 6.10 N, 7.07. Found: C, 66.28 H, 5.72 N, 6.50.

Step B—Synthesis of 5-Amino-7-(methoxycarbonylmethyl)-5,7-dihydro-6H-dibenz[b,d]azepin-6-one Hydrochloride The product from Step A was deprotected using General Procedure E to provide the title compound as a colorless solid after evaporation and vacuum drying.

Physical data were as follows:

$^1$H-nmr (DMSO-$d_6$): δ=7.72–7.42 (m, 8H), 4.92 (s, 1H), 4.53 (m, 2H), 3.52 (s, 3H).

$C_{17}H_{16}N_2O_3$·HCl (MW=332.78); mass spectroscopy (MH+free base) 297.

Example 6

Synthesis of 5-Amino-7-(3,3-dimethyl-2-butanonyl)-5,7-dihydro-6H-dibenz[b,d]azepin-6-one Hydrochloride Step A—Synthesis of 5-(N-Boc-Amino)-7-(3,3-dimethyl-butanonyl)-5,7-dihydro-6H-dibenz[b,d]azepin-6-one A solution of 5-(N-Boc-amino)-5,7-dihydro-6H-dibenz[b,d]azepin-6-one (0.2 g, 0.617 mmol) (Example 3) in DMF was treated with $Cs_2CO_3$ (0.3 g, 0.925 mmol) and warmed to 60° C. To this reaction mixture was added 1-chloro-3,3-dimethyl-2-butanone (0.096 mL, 0.74 mmol) (Aldrich) and stirring was continued for 17 h. After cooling to 23° C., the mixture was diluted with $CH_2Cl_2$, washed with several portions of brine and dried over $Na_2SO_4$. The title compound was isolated as a colorless solid.

Physical data were as follows:

$C_{25}H_{30}N_2O_4$ (MW=422.522); mass spectroscopy (MH+) 423.

Anal. Calcd for $C_{25}H_{30}N_2O_4$. 0.6825 mol $H_2O$; C, 69.05 H, 7.27 N, 6.44. Found: C, 69.03 H, 7.27 N, 6.60.

Step B—Synthesis of 5-Amino-7-(3,3-dimethyl-2-butanonyl)-5,7-dihydro-6H-dibenz[b,d]azepin-6-one Hydrochloride The product from Step A was deprotected using General Procedure E to provide the title compound as a colorless solid after evaporation and vacuum drying.

Physical data were as follows:

$^1$H-nmr (DMSO-$d_6$): δ=9.14 (bs, 3H), 7.76–7.32 (m, 8H), 4.99 (d, 1H), 4.98 (s, 1H), 4.69 (d, 1H), 1.15 (s, 9H).

$C_{20}H_{22}N_2O_2$ HCl (MW=358); mass spectroscopy (MH+ free base) 323.

Example 7

Synthesis of 5-Amino-7-phenbutyl-5,7-dihydro-6H-dibenz[b,d]azepin-6-one

Following General Procedure A and using 5,7-dihydro-6H-dibenz[b,d]azepin-6-one (prepared as described in Brown, et. al., *Tetrahedron Letters*, No. 8, 667–670, (1971) and references cited therein) and 1-chloro-4-phenylbutane (Aldrich), the title compound was prepared.

Physical data were as follows:

Step B: Synthesis of 5-Hydroxyimino-7-phenbutyl-5,7-dihydro-6H-dibenz[b,d]azepin-6-one $^1$H-nmr ($CDCl_3$): δ=2.37 (m, 2H), 3.65 (m, 1H), 4.50 (m, 1H).

$C_{15}H_{13}NO$ (MW=370.45); mass spectroscopy (MH+) 371.2.

Step C: Synthesis of 5-Amino-7-phenbutyl-5,7-dihydro-6H-dibenz[b,d]azepin-6-one $^1$H-nmr ($CDCl_3$): δ=2.27 (m, 2H), 3.55 (m, 1H), 4.33 (m, 1H).

(MW=356.47); mass spectroscopy (MH+) 357.3.

Example 8

Synthesis of 5-Amino-7-cyclopropymethyl-5,7-dihydro-6H-dibenz[b,d]azepin-6-one

Following General Procedure A and using 5,7-dihydro-6H-dibenz[b,d]azepin-6-one (prepared as described in R. F. C. Brown, et. al., *Tetrahedron Letters* 1971, 8, 667–670[9] and references cited therein) and (bromomethyl)cyclopropane (Aldrich), the title compound was prepared.

Physical data were as follows:

Step B: Synthesis of 5-Hydroxyimino-7-cyclopropylmethyl-5,7-dihydro-6H-dibenz[b,d]azepin-6-one $^1$H-nmr ($CDCl_3$): δ=3.6 (m, 1H), 4.15 (m, 1H).

(MW=292.34); mass spectroscopy (MH+) 293.2.

Example 9

Synthesis of 5-Amino-7-(2',2',2'-trifluoroethyl)-5,7-dihydro-6H-dibenz[b,d]azepin-6-one Following General Procedure A and using 5,7-dihydro-6H-dibenz[b,d]azepin-6-one (prepared as described in R. F. C. Brown, et. al., *Tetrahedron Letters* 1971, 8, 667–670[9] and references cited therein) and 1-bromo-2,2,2-trifluoroethane (Aldrich), the tide compound was prepared.

Physical data were as follows:

Step A: Synthesis of 7-(2',2',2'-Trifluoroethyl)-5,7-dihydro-6H-dibenz[b,d]azepin-6-one $^1$H-nmr (CDCl$_3$): δ=3.46 (d, 1H), 3.63 (d, 1H), 4.07 (m, 1H), 5.06(m, 1H).

Step B: Synthesis of 5-Hydroxyimino-7-(2',2',2'-trifluoroethyl)-5,7-dihydro-6H-dibenz[b,d]azepin-6-one $^1$H-nmr (CDCl$_3$): δ=4.13 (m, 1H), 5.27 (m, 1H).

(MW=320.27); mass spectroscopy (MH+) 321.2.

Example 10

Synthesis of 5-Amino-7-cyclohexyl-5,7-dihydro-6H-dibenz[b,d]azepin-6-one

Following General Procedure A and using 5,7-dihydro-6H-dibenz[b,d]azepin-6-one (prepared as described in R. F. C. Brown, et. al., *Tetrahedron Letters* 1971, 8, 667–670[9] and references cited therein) and bromocyclohexane (Aldrich), the title compound was prepared.

Physical data were as follows:

Step A: Synthesis of 7-Cyclohexyl-5,7-dihydro-6H-dibenz[b,d]-azepin-6-one $^1$H-nmr (CDCl$_3$): δ=3.35 (d, 1H), 3.47 (d, 1H), 4.03 (m, 1H).

Example 11

Synthesis of 5-Amino-7-hexyl-5,7-dihydro-6H-dibenz[b,d]azepin-6-one Hydrochloride Following General Procedure A and using 5,7-dihydro-6H-dibenz[b,d]azepin-6-one (prepared as described in R. F. C. Brown, et. al., *Tetrahedron Letters* 1971, 8, 667–670[9] and references cited therein) and 1-bromohexane (Aldrich), the title compound was prepared.

Example 12

Synthesis of 5-Amino-9-fluoro-7-methyl-5,7-dihydro-6H-dibenz[b,d]azepin-6-one Hydrochloride Step A—Synthesis of 4-Fluoro-2-methylphenylboronate Pinacol Ester 2-Bromo-5-fluorotoluene (1.0 eq.) (Aldrich) was stirred in THF at −78° C. sec-Butyllithium (1.05 eq., 1.3 M in cyclohexane) was slowly added and the mixture was stirred for 45 minutes. Trimethylborate (1.5 eq) (Aldrich) was then added and the mixture was allowed to warm to ambient temperature. After stirring for 1 hour, pinacol (2 eq.) (Aldrich) was added. The mixture was stirred for 16 hours then was concentrated under reduced pressure. The resulting residue was slurried in CH$_2$Cl$_2$ and filtered through Celite. The filtrate was concentrated to yield an oil which was purified by chromatography on deactivated silica gel (Et$_3$N) to yield the title compound.

Step B—Synthesis of N-Boc-2-bromoaniline

2-Bromoaniline (1 eq.) (Aldrich) and di-tert-butyl-dicarbonate (1.1 eq.) (Aldrich) were stirred at 80° C. for 20 hours. The resulting mixture was allowed to cool and was directly distilled using house vacuum to provide the title compound.

Step C—Synthesis of N-Boc-2-amino-4'-fluoro-2'-methylbiphenyl

N-Boc-2-bromoaniline (1 eq.) (Step B), the arylboronate ester (1.1 eq.) (Step A), K$_2$CO$_3$ (1.1 eq.) and tetrakis (triphenylphosphine)palladium(0) (0.02 eq.) were stirred in 20% water/dioxane under nitrogen. The solution was heated at reflux for 10 hours. The mixture was allowed to cool then was concentrated. The resulting residue was partitioned between water and chloroform. The organic portion was dried and concentrated to yield an oil which was purified by silica gel chromatography using 1:1 CH$_2$Cl$_2$/hexanes.

Step D—Synthesis of 9-Fluoro-5,7-dihydro-6H-dibenz[b,d]azepin-6-one

Following General Procedure B and using the product from Step C, the title compound was prepared.

Physical data were as follows:

(MW=227.24); mass spectroscopy (MH+) 228.0.

Step E—Synthesis of 9-Fluoro-7-methyl-5,7-dihydro-6H-dibenz[b,d]azepin-6-one

9-Fluoro-5,7-dihydro-6H-dibenz[b,d]azepin-6-one (1 eq.) (Step D), cesium carbonate (1.1 eq.) (Aldrich) and methyl iodide (1.1 eq.) (Aldrich) were stirred in dry DMF at ambient temperature for 16 hours. The mixture was concentrated under reduced pressure to provide a residue which was partitioned between EtOAc and water. The organic portion was dried and concentrated to yield an oil which was purified by silica gel chromatography to provide the title compound.

Physical data were as follows:

$^1$H-nmr (CDCl$_3$): δ=3.33 (s, 3H), 3.42 (d, 1H), 3.54 (d, 1H).

(MW=241.27); mass spectroscopy (MH+) 242.0.

Step F—Synthesis of 5-Amino-9-fluoro-7-methyl-5,7-dihydro-6H-dibenz[b,d]azepin-6-one Following General Procedure A, Steps B and C, and using the product from Step E, the title compound was prepared.

Physical data were as follows:

Gen. Proc. A/Step B: Synthesis of 5-Hydroxyimino-9-fluoro-7-methyl-5,7-dihydro-6H-dibenz[b,d]azepin-6-one $^1$H-nmr (CDCl$_3$): δ=3.44, 3.47 (singlets, 3H).

(MW=270.26); mass spectroscopy (MH+) 271.4.

Gen. Proc. A/Step C: Synthesis of 5-Amino-9-fluoro-7-methyl-5,7-dihydro-6H-dibenz[b,d]azepin-6-one $^1$H-nmr (CDCl$_3$): δ=2.08 (s, 2H); 3.34 (s, 3H); 4.30 (s, 1H).

(MW=256.3); mass spectroscopy (MH+) 257.0.

Example 13

Synthesis of 5-Amino-10-fluoro-7-methyl-5,7-dihydro-6H-dibenz[b,d]azepin-6-one Hydrochloride Following the procedure of Example 12 and using 2-bromo-4-fluorotoluene (Lancaster) in Step A, the title compound was prepared.

Physical data were as follows:

Step D: Synthesis of 10-Fluoro-5,7-dihydro-6H-benz[b,d]azepin-6-one $^1$H-nmr (CDCl$_3$/DMSO-d$_6$): δ=3.34 (q, 2 h); 9.91 (s, 1H).

(MW=227.24); mass spectroscopy (MH+) 228.0.

Step E: Synthesis of 10-Fluoro-7-methyl-5,7-dihydro-6H-dibenz[b,d]azepin-6-one $^1$H-nmr (CDCl$_3$): δ=3.33 (s, 3H), 3.42 (d, 1H), 3.57 (d, 1H).

(MW=241.27); mass spectroscopy (MH+) 242.0.

Step F: Synthesis of 5-Amino-10-fluoro-7-methyl-5,7-dihydro-6H-dibenz[b,d]azepin-6-one Gen. Proc. A/Step B: Synthesis of 5-Hydroxyimino-10-fluoro-7-methyl-5,7-dihydro-6H-dibenz[b,d]azepin-6-one $^1$H-nmr (CDCl$_3$): δ=3.43, 3.47 (singlets, 3H).

(MW=270.26); mass spectroscopy (MH+) 271.4.

Gen. Proc. A/Step C: Synthesis of 5-Amino-10-fluoro-7-methyl-5,7-dihydro-6H-dibenz[b,d]azepin-6-one $^1$H-nmr (CDCl$_3$): δ=2.06 (s, 2H); 3.34 (s, 3H); 4.28 (s, 1H).

(MW=256.3); mass spectroscopy (MH+) 257.0.

Example 14

Synthesis of 5-Amino-13-fluoro-7-methyl-5,7-dihydro-6H-dibenz[b,d]azepin-6-one Hydrochloride Following the procedure of Example 12 and using 2-bromo-4-fluoroaniline (Lancaster) in Step B, and o-tolylboronic acid (Aldrich) in Step C, the title compound was prepared.

Physical data were as follows:

Step D: Synthesis of 13-Fluoro-5,7-dihydro-6H-dibenz[b,d]azepin-6-one $^1$H-nmr (CDCl$_3$): δ=3.5 (bm, 2H).

(MW=227.24); mass spectroscopy (MH+) 227.8.

Step E: Synthesis of 13-Fluoro-7-methyl-5,7-dihydro-6H-dibenz[b,d]azepin-6-one $^1$H-nmr (DMSO-d$_6$): δ=3.33 (s, 3H), 3.35 (d, 1H), 3.52 (d, 1H).

(MW=241.27); mass spectroscopy (MH+) 241.8.

Step F: Synthesis of 5-Amino-13-fluro-7-methyl-5,7-dihydro-6H-dibenz[b,d]azepin-6-one Gen. Proc. A/Step B: Synthesis of 5-Hydroxyimino-13-fluoro-7-methyl-5,7-dihydro-6H-dibenz[b,d]azepin-6-one $^1$H-nmr (CDCl$_3$): d=3.39, 3.44 (singlets, 3H).

(MW=270.26); mass spectroscopy (M+) 270.1.

Gen. Proc. A/Step C: Synthesis of 5-Amino-13-fluoro-7-methyl-5,7-dihydro-6H-dibenz[b,d]azepin-6-one $^1$H-nmr (CDCl$_3$): δ=2.06 (bs, 2H); 3.33 (s, 3H); 4.35(s, 1H).

R$_f$ (5% methanol/chloroform)=0.3.

Example 15

Synthesis of 5-Amino-7-methyl-1,2,3,4,5,7-hexahydro-6H-dicyclohexyl[b,d]azepin-6one 5-Amino-7-methyl-5,7-dihydro-6H-dibenz[b,d]azepin-6-one hydrochloride (Example 1) was dissolved in a 1:1 mixture of EtOAc/HOAc. Rhodium on carbon (5%) was added and the mixture was stirred at 60° C. under 60 psi of hydrogen for 3 days. The reaction mixture was then filtered and the filtrate was concentrated to provide an oil which was purified by SCX-cation exchange chromatography to yield the title compound.

Physical data were as follows:

(MW=250.38); mass spectroscopy (MH+) 251.3.

Example 16

Synthesis of (S)- and (R)-5-(L-Alaninyl)amino-7-methyl-5,7-dihydro-6H-dibenz[b,d]azepin-6-one Step A—Synthesis of S)- and (R)-5-(N-Boc-L-Alaninyl)amino-7-methyl-5,7-dihydro-6H-dibenz[b,d]azepin-6-one N-Boc-L-Alanine (0.429 g, 2.26 mmol) (Aldrich) was dissolved in THF and treated with HOBt hydrate (0.305 g, 2.26 mmol), and 5-amino-7-methyl-5,7-dihydro-6H-dibenz[b,d]azepin-6-one (0.45 g, 1.89 mmol) (Example 1). The temperature was lowered to 0° C. and the reaction mixture was treated with EDC (0.449 g, 2.26 mmol) (Alrich) and stirred for 17 hours un der N$_2$. The reaction mixture was then evaporated and the residue diluted with EtOAc/H$_2$O, washed 1.0 N HCl, sat. NaHCO$_3$, brine and dried over Na$_2$SO$_4$. The resulting diastereomers were separated on a Chiralcel OD column using 10% IPA/heptane at 1.5 mL/minute.

Isomer 1: Retention time 3.37 minutes.

NMR data was as follows:

$^1$H-NMR (CDCl$_3$): δ=7.62–7.33 (m, 9H), 5.26 (d, 1H), 5.08 (m, 1H), 4.34 (m, 1H), 3.35 (s, 3H), 1.49 (s, 9H), 1.40 (d, 3H).

Optical Rotation: [α]$_{20}$=−96@589 nm (c=1, MeOH).

C$_{23}$H$_{27}$N$_3$O$_4$ (MW=409.489); mass spectroscopy (MH+) 409.

Anal. Calcd for C$_{23}$H$_{27}$N$_3$O$_4$; C, 67.46 H, 6.64 N, 10.26. Found: C, 68.42 H, 7.02 N, 9.81.

Isomer 2: Retention time 6.08 minutes.

NMR data was as follows:

$^1$H-NMR (CDCl$_3$): δ=7.74 (bd, 1H), 7.62–7.32 (m, 8H), 5.28 (d, 1H), 4.99 (m, 1H), 4.36 (m, 1H), 3.35 (s, 3H), 1.49 (s, 9H), 1.46 (d, 3H).

Optical Rotation: [α]$_{20}$=69@589 nm (c=1, MeOH).

C$_{23}$H$_{27}$N$_3$O$_4$ (MW=409.489); mass spectroscopy (MH+) 409.

Anal. Calcd for C$_{23}$H$_{27}$N$_3$O$_4$; C, 67.46 H, 6.64 N, 10.26. Found: C, 67.40 H, 6.62 N, 10.02.

Step B—Synthesis of (S)- and (R)-5-(L-Alaninyl)amino-7-methyl-5,7-dihydro-6H-dibenz[b,d]azepin-6-one Hydrochloride In separate reaction flasks, each isomer from Step A was dissolved in dioxane and treated with excess HCl(g). After stirring for 17 hours, the title compounds were isolated as colorless solids after evaporation and vacuum drying.

Isomer 1:

C$_{18}$H$_{19}$N$_3$O$_2$.HCl (MW=345.832); mass spectroscopy (MH+free base) 309.

Optical Rotation: [α]$_{20}$=−55@589 nm (c=1, MeOH).

Isomer 2:

C$_{18}$H$_{19}$N$_3$O$_2$.HCl (MW=345.832); mass spectroscopy (MH+free base) 309.

Optical Rotation: [α]$_{20}$=+80@589 nm (c=1, MeOH).

Example 17

Synthesis of (S)- and (R)-5-(L-Valinyl)amino-7-methyl-5,7-dihydro-6H-dibenz[b,d]azepin-6-one Step A—Synthesis of (S)- and (R)-5-(N-Boc-L-Valinyl)amino-7-methyl-5,7-dihydro-6H-dibenz[b,d]azepin-6-one N-Boc-L-Valine (0.656 g, 3.02 mmol) (Aldrich) was dissolved in THF and treated with HOBt hydrate (0.408, 3.02 mmol), DIPEA (1.05 mL, 6.05 mmol) and 5-amino-7-methyl-5,7-dihydro-6H-dibenz[b,d]azepin-6-one hydrochloride (0.75 g, 2.75 mmol) (Example 1). The temperature was lowered to 0° C. and the reaction mixture was treated with EDC (0.601 g, 3.02 mmol) (Alrich) and stirred for 17 hours under N$_2$. The reaction mixture was then evaporated and the residue diluted with EtOAc/H$_2$O, washed 1.0 N HCl, sat. NaHCO$_3$, brine and dried over Na$_2$SO$_4$. The resulting diastereomers were separated on a Chiralcel OD column using 10% IPA/heptane at 1.5 mL/minute.

Isomer 1: Retention time 3.23 minutes.

Optical Rotation: $[\alpha]_{20}=-120@589$ nm (c=1, MeOH).

C$_{25}$H$_{31}$N$_3$O$_4$ (MW=437.544); mass spectroscopy (MH+) 438

Isomer 2: Retention time 6.64 minutes.

Optical Rotation: $[\alpha]_{20}=+50@589$ nm (c=1, MEOH).

C$_{25}$H$_{31}$N$_3$O$_4$ (MW=437.544); mass spectroscopy (MH+) 438

Step B—Synthesis of (S)- and (R)-5-(L-Valinyl)-amino-7-mehyl-5,7-dihydro-6H-dibenz[b,d]azepin-6-one Hydrochloride In separate reaction flasks, each of the isomers from Step A was dissolved in dioxane and treated with excess HCl(g). After stirring for 17 hours, the title compounds were isolated as colorless solids after evaporation and vacuum drying.

Isomer 1:

C$_{20}$H$_{23}$N$_3$O$_2$.HCl (MW=373.88); mass spectroscopy (MH+free base) 338.

Optical Rotation: $[\alpha]_{20}=-38@589$ nm (c=1, MeOH).

Isomer 2:

C$_{20}$H$_{23}$N$_3$O$_2$.HCl (MW=373.88); mass spectroscopy (MH+free base) 338.

Optical Rotation: $[\alpha]_{20}=+97@589$ nm (c=1, MeOH).

Example 18

Synthesis of (S)- and (R)-5-(L-tert-Leucinyl)amino-7-methyl-5,7-dihydro-6H-dibenz[b,d]azepin-6-one Step A—Synthesis of (S)- and (R)-5-(N-Boc-L-tert-Leucinyl)-amino-7-methyl-5,7-dihydro-6H-dibenz[b,d]azepin-6-one N-Boc-L-tert-Leucine (0.698 g, 3.02 mmol) (Fluka) was dissolved in THF and treated with HOBt hydrate (0.408, 3.02 mmol), DIPEA (1.05 mL, 6.05 mmol) and 5-amino-7-methyl-5,7-dihydro-6H-dibenz[b,d]azepin-6-one hydrochloride (0.75 g, 2.75 mmol) (Example 1). The temperature was lowered to 0° C. and the reaction mixture was treated with EDC (0.601 g, 3.02 mmol) (Alrich) and stirred for 17 hours under N$_2$. The reaction mixture was then evaporated and the residue diluted with EtOAc/H$_2$O, washed 1.0 N HCl, sat. NaHCO$_3$, brine and dried over Na$_2$SO$_4$. The diastereomers were separated on a Chiralcel OD column using 10% IPA/heptane at 1.5 mL/minute.

Isomer 1: Retention time 3.28 minutes.

Optical Rotation: $[\alpha]_{20}=-128@589$ nm (c=1, MeOH).

C$_{26}$H$_{33}$N$_3$O$_4$ (MW=451.571); mass spectroscopy (MH+) 452

Isomer 2: Retention time 5.52 minutes.

Optical Rotation: $[\alpha]_{20}=+26@589$ nm (c=1, MeOH).

C$_{26}$H$_{33}$N$_3$O$_4$ (MW=451.571); mass spectroscopy (MH+) 452

Step B—Synthesis of (S)- and (R)-5-(L-tert-Leucinyl) amino-7-methyl-5,7-dihydro-6H-dibenz[b,d]azepin-6-one Hydrochloride In separate reaction flasks, each of the isomers from Step A was dissolved in dioxane and treated with excess HCl(g). After stirring for 17 hours, the title compounds were isolated as colorless solids after evaporation and vacuum drying.

Isomer 1:

C$_{21}$H$_{25}$N$_3$O$_2$.HCl (MW=387.91); mass spectroscopy (MH+free base) 352.

Optical Rotation: $[\alpha]_2=-34@589$ nm (c=1, MEOH).

Isomer 2:

C$_{21}$H$_{25}$N$_3$O$_2$.HCl (MW=387.91); mass spectroscopy (MH+free base) 352.

Optical Rotation: $[\alpha]_{20}=+108@589$ nm (c=1, MeOH).

Example 19

Synthesis of 5-(L-Alaninyl)amino-7-methyl-5,7-dihydro-6H-dibenz[b,d]azepin-6-one Hydrochloride Step A—Synthesis of 5-(N-Boc-L-Alaninyl)amino-7-methyl-5,7-dihydro-6H-dibenz[b,d]azepin-6-one Following General Procedure D and using N-Boc-L-alanine (Aldrich) and 5-amino-7-methyl-5,7-dihydro-6H-dibenz[b,d]azepin-6-one (Example 1), the title compound was prepared.

Step B—Synthesis of 5-(L-Alaninyl)amino-7-methyl-5, 7-dihydro-6H-dibenz[b,d]azepin-6-one Hydrochloride Following General Procedure E and using the product from Step A, the title compound was prepared.

Example 20

Synthesis of 5-(L-Valinyl)amino-7-methyl-5,7-dihydro-6H-dibenz[b,d]azepin-6-one Hydrochloride Step A—Synthesis of 5-(N-Boc-L-Valinyl)amino-7-methyl-5,7-dihydro-6H-dibenz[b,d]azepin-6-one Following General Procedure D and using N-Boc-L-valine (Aldrich) and 5-amino-7-methyl-5,7-dihydro-6H-dibenz[b,d]azepin-6-one (Example 1), the title compound was prepared.

Step B—Synthesis of 5-(L-Valinyl)amino-7-methyl-5,7-dihydro-6H-dibenz[b,d]azepin-6-one Hydrochloride Following General Procedure E and using the product from Step A, the title compound was prepared.

Example 21

Synthesis of 5-(L-Alaninyl)amino-9-fluoro-7-methyl-5,7-dihydro-6H-dibenz[b,d]azepin-6-one Hydrochloride Step A—Synthesis of 5-(N-Boc-L-Alaninyl)amino-9-fluoro-7-methyl-5,7-dihydro-6H-dibenz[b,d]azepin-6-one Following General Procedure D and using N-Boc-L-alanine (Aldrich) and 5-amino-9-fluoro-7-methyl-5,7-dihydro-6H-dibenz[b,d]azepin-6-one (Example 12), the title compound was prepared.

Step B—Synthesis of 5-(L-Alaninyl)amino-9-fluoro-7-methyl-5,7-dihydro-6H-dibenz[b,d]azepin-6-one Hydrochloride Following General Procedure E and using the product from Step A, the title compound was prepared.

Example 22

Synthesis of 5-(L-Alaninyl)amino-10-fluoro-7-methyl-5,7-dihydro-6H-dibenz[b,d]azepin-6-one Hydrochloride Step A—Synthesis of 5-(N-Boc-L-Alaninyl)-amino-10-fluoro-7-methyl-5,7-dihydro-6H-dibenz[b,d]azepin-6-one Following General Procedure D and using N-Boc-L-alanine (Aldrich) and 5-amino-10-fluoro-7-methyl-5,7- dihydro-6H-dibenz[b,d]azepin-one (Example 13), the title compound was prepared.

Step B—Synthesis of 5-(L-Alaninyl)amino-10-fluoro-7-methyl-5,7-dihydro-6H-dibenz[b,d]azepin-6-one Hydrochloride Following General Procedure E and using the product from Step A, the title compound was prepared.

Example 23

Synthesis of 5-(L-Alaninyl)amino-13-fluoro-7-methyl-5,7-dihydro-6H-dibenz[b,d]azepin-6-one Hydrochloride Step A—Synthesis of 5-(N-Boc-L-Alaninyl)amino-13-fluoro-7-methyl-5 7-dihydro-6H-dibenz[b,d]azepin-6-one Following General Procedure D and using N-Boc-L-alanine (Aldrich) and 5-amino-13-fluoro-7-methyl-5,7-dihydro-6H-dibenz[b,d]azepin-6-one (Example 14), the title compound was prepared.

Step B—Synthesis of 5-(L-Alaninyl)amino-13-fluoro-7-methyl-5,7-dihydro-6H-dibenz[b,d]azepin-6-one Hydrochloride Following General Procedure E and using the product from Step A, the title compound was prepared.

Example 24

Synthesis of 5-(L-Alaninyl)amino-7-cyclopropylmethyl-5,7-dihydro-6H-dibenz[b,d]azepin-6-one Hydrochloride Step A—Synthesis of 5-(N-Boc-L-Alaninyl)amino-7-cyclopropylmethyl-5,7-dihydro-6H-dibenz[b,d]azepin-6-one Following General Procedure D and using N-Boc-L-alanine (Aldrich) and 5-amino-7-cyclopropylmethyl-5,7-dihydro-6H-dibenz[b,d]azepin-6-one (Example 8), the title compound was prepared.

Step B—Synthesis of 5-(L-Alaninyl)amino-7-cyclopropylmethyl-5,7-dihydro-6H-dibenz[b,d]azepin-6-one Hydrochloride Following General Procedure E and using the product from Step A, the title compound was prepared.

Example 25

Synthesis of 5-(L-Alaninyl)amino-7-phenbutyl-5,7-dihydro-6H-dibenz[b,d]azepin-6-one Hydrochloride Step A—Synthesis of 5-(N-Boc-L-Alaninyl)amino-7-phenbutyl-5,7-dihydro-6H-dibenz[b,d]azepin-6-one Following General Procedure D and using N-Boc-L-alanine (Aldrich) and 5-amino-7-phenbutyl-5,7-dihydro-6H-dibenz[b,d]azepin-6-one (Example 7), the title compound was prepared.

Step B—Synthesis of 5-(L-Alaninyl)amino-7-phenbutyl-5,7-dihydro-6H-dibenz[b,d]azepin-6-one Hydrochloride Following General Procedure E and using the product from Step A, the title compound was prepared.

Example 26

Synthesis of 5-(L-Valinyl)amino-7-cyclopropylmethyl-5,7-dihydro-6H-dibenz[b,d]azepin-6-one Hydrochloride Step A—Synthesis of 5-(N-Boc-L-Valinyl)amino-7-cyclopropylmethyl-5,7-dihydro-6H-dibenz[b,d]azepin-6-one Following General Procedure D and using N-Boc-L-valine (Aldrich) and 5-amino-7-cyclopropylmethyl-5,7-dihydro-6H-dibenz[b,d]azepin-6-one (Example 8), the title compound was prepared.

Step B—Synthesis of 5-(L-Valinyl)amino-7-cyclopropylmethyl-5,7-dihydro-6H-dibenz[b,d]azepin-6-one Hydrochloride Following General Procedure E and using the product from Step A, the title compound was prepared.

Example 27

Synthesis of 5-(L-Valinyl)amino-7-phenbutyl-5,7-dihydro-6H-dibenz[b,d]azepin-6-one Hydrochloride Step A—Synthesis of 5-(N-Boc-L-Valinylamino-7-phenbutyl-5,7-dihydro-6H-dibenz[b,d]azepin-6-one Following General Procedure D and using N-Boc-L-valine (Aldrich) and 5-amino-7-phenbutyl-5,7-dihydro-6H-dibenz[b,d]azepin-6-one (Example 7), the title compound was prepared.

Step B—Synthesis of 5-(L-Valinyl)amino-7-phenbutyl-5,7-dihydro-6H-dibenz[b,d]azepin-6-one Hydrochloride Following General Procedure E and using the product from Step A, the title compound was prepared.

Example 28

Synthesis of 5-(L-Valinyl)amino-7-hexyl-5,7-dihydro-6H-dibenz[b,d]azepin-6-one Hydrochloride Step A—Synthesis of 5-(N-Boc-L-Valinyl)amino-7-hexyl-5,7-dihydro-6H-dibenz[b,d]azepin-6-one Following General Procedure D and using N-Boc-L-valine (Aldrich) and 5-amino-7-hexyl-5,7-dihydro-6H-dibenz[b,d]azepin-6-one (Example 11), the title compound was prepared.

Step B—Synthesis of 5-(L-Valinyl)amino-7-hexyl-5,7-dihydro-6H-dibenz[b,d]azepin-6-one Hydrochloride Following General Procedure E and using the product from Step A, the title compound was prepared.

Physical data were as follows:

$^1$H-nmr (DMSO-$d_6$): δ=2.17 (bm, 1H); 3.98, 4.07 (doublets, 1H); 4.27 (m, 1H); 5.24, 5.33 (doublets, 1H).

(MW=407.55, free base); mass spectroscopy (MH+) 408.1.

Example 29

Synthesis of 5-(L-Valinyl)amino-9-fluoro-7-methyl-5,7-dihydro-6H-dibenz[b,d]azepin-6-one Hydrochloride Step A—Synthesis of 5-(N-Boc-L-Valinyl)amino-9-fluoro-7-methyl-5,7-dihydro-6H-dibenz[b,d]azepin-6-one Following General Procedure D and using N-Boc-L-valine (Aldrich) and 5-amino-9-fluoro-7-methyl-5,7-dihydro-6H-dibenz[b,d]azepin6-one (Example 12), the title compound was prepared.

Step B—Synthesis of 5-(L-Valinyl)amino-9-fluoro-7-methyl-5,7-dihydro-6H-dibenz[b,d]azepin-6-one Hydrochloride Following General Procedure E and using the product from Step A, the title compound was prepared.

Physical data were as follows:

$^1$H-nmr (DMSO-$d_6$): δ=2.05–2.27 (bm, 1H); 3.96, 4.07 (doublets, 1H); 5.26, 5.32 (doublets, 1H).

(MW=355.41, free base); mass spectroscopy (MH+) 356.3.

Anal. Calcd for $C_{20}H_{22}FN_3O_2 \cdot HCl$; C, 61.30 H, 5.92 N, 10.72. Found: C, 61.15 H, 6.22 N, 10.69.

Example 30

Synthesis of 5-(L-Valinyl)amino-10-fluoro-7-methyl-5,7-dihydro-6H-dibenz[b,d]azepin-6-one Hydrochloride Step A—Synthesis of 5-(N-Boc-L-Valinyl)amino-10-fluoro-7-methyl-5,7-dihydro-6-dibenz[b,d]azepin-6-one Following General Procedure D and using N-Boc-L-valine (Aldrich) and 5-amino-10-fluoro-7-methyl-5,7-dihydro-6H-dibenz[b,d]azepin-6-one (Example 13), the title compound was prepared.

Step B—Synthesis of 5-(L-Valinyl)amino-10-fluoro-7-methyl-5,7-dihydro-6-dibenz[b,d]azepin-6-one Hydrochloride Following General Procedure E and using the product from Step A, the title compound was prepared.

Physical data were as follows:

$^1$H-nmr (DMSO-$d_6$): δ=2.05–2.30 (bm, 1H); 3.97, 4.06 (doublets, 1H); 5.23, 5.32 (doublets, 1H).

(MW=355.41, free base); mass spectroscopy (MH+) 356.3.

Anal. Calcd for $C_{20}H_{22}FN_3O_2 \cdot HCl$; C, 61.30 H, 5.92 N, 10.72. Found: C, 61.04 H, 5.90 N, 11.01.

Example 31

Synthesis of 5-(L-Valinyl)amino-13-fluoro-7-methyl-5,7-dihydro-6H-dibenz[b,d]azepin-6-one Hydrochloride Step A—Synthesis of 5-(N-Boc-L-Vainyl)amino-13-fluoro-7-methyl-5,7-dihydro-6H-dibenz[b,d]azepin-6-one Following General Procedure D and using N-Boc-L-valine (Aldrich) and 5-amino-13-fluoro-7-methyl-5,7-dihydro-6H-dibenz[b,d]azepin-6-one (Example 14), the title compound was prepared.

Step B—Synthesis of 5-(L-Valinyl)amino-13-fluoro-7-methyl-5,7-dihydro-6H-dibenz[b,d]azepin-6-one Hydrochloride Following General Procedure E and using the product from Step A, the title compound was prepared.

Physical data were as follows:

$^1$H-nmr (DMSO-$d_6$): δ=2.05–2.28 (bm, 1H); 3.98, 4.07 (doublets, 1H); 5.27, 5.34 (doublets, 1H).

(MW=355.41, free base); mass spectroscopy (MH+) 356.4.

Anal. Calcd for $C_{20}H_{22}FN_3O_2 \cdot HCl$; C, 61.30 H, 5.92 N, 10.72. Found: C, 61.24 H, 6.07 N, 10.86.

Example 32

Synthesis of 5-Amino-9,13-difluoro-7-methyl-5,7-dihydro-6H-dibenz[b,d]azepin-6-one Following the procedure of Example 12 and using 2-bromo-4-fluoroaniline (Lancaster) in Step B, the title compound was prepared.

Physical data were as follows:

Step D: Synthesis of 9,13-Difluoro-5,7-dihydro-6H-dibenz[b,d]azepin-6-one (MW=245.23); mass spectroscopy (MH+) 246.0.

Step F: Synthesis of 5-Amino-9,13-difluoro-7-methyl-5,7-dihydro-6H-dibenz[b,d]azepin-6-one $^1$H-nmr (CDCl$_3$): δ=2.14 (s, 2H); 3.31 (s, 3H); 4.32 (s, 1H).

(MW=274.3); mass spectroscopy (MH+) 275.0.

Example 33

Synthesis of 5-Amino-10,13-difluoro-7-methyl-5,7-dihydro-6H-dibenz[b,d]azepin-6-one Following the procedure of Example 12 and using 2-bromo-4-fluorotoluene (Lancaster) in Step A and 2-bromo-4-fluoroaniline (Lancaster) in Step B, the title compound was prepared.

Physical data were as follows:

Step D: Synthesis of 10,13-Difluoro-5,7-dihydro-6H-dibenz[b,d]azepin-6-one (MW=245.23); mass spectroscopy (MH+) 246.0.

Step E: Synthesis of 10,13-Difluoro-5,7-methyl-5,7-dihydro-6H-dibenz[b,d]azepin-6-one $^1$H-nmr (CDCl$_3$): δ=3.30 (s, 3H), 3.35 (d, 1H), 3.58 (d, 1H).

Step F: Synthesis of 5-Amino-10,13-difluoro-7-methyl-5,7-dihydro-6H-dibenz[b,d]azepin-6one $^1$H-nmr (CDCl$_3$): δ=2.06 (s, 2H); 3.32 (s, 3H); 4.27 (s, 1H).

(MW=274.3); mass spectroscopy (MH+) 275.0.

Example 34

Synthesis of 9-Amino-5,6-dihydro-4H-quino[8,1-ab][3]benzazepin-8(9H)-one Hydrochlororide Step A—Synthesis of 8-Phenylquinoline A degassed solution of 8-bromoquinoline (1.0 g, 4.81 mmol) (Aldrich) in dioxane (50 mL)/H$_2$O (10 mL) was treated with phenylboronic acid (0.64 g, 5.29 mmol) (Aldrich), Pd(Ph$_3$P)$_4$ (0.050 g, 0.04 mmol) and K$_2$CO$_3$ (0.73 g, 5.29 mmol). After refluxing for 4 h under a N$_2$ atmosphere the reaction was allowed to cool, diluted with EtOAc and separated. After drying over Na$_2$SO$_4$ and SiO$_2$ chromatography (95:5 Hexanes/EtOAc) the titled compound was isolated as a colorless oil.

Physical data were as follows:

$^1$H-nmr (CDCl$_3$): δ=8.97 (d, 1H), 8.22 (dd, 1H), 7.87–7.39 (m, 9H).

$C_{15}H_{11}N$ (MW=205); mass spectroscopy (MH+) 206.

Step B—Synthesis of 8-Phenyl-1,2,3,4-tetrahydroquinoline

The product from Step A (0.99 g, 4.82 mmol) was hydrogenated according to the procedure described by Honel, M., et. al., J.C.S. Perkin I, (1980), 1933–1938.

Physical data were as follows:

$^1$H-nmr (CDCl$_3$): δ=7.46 (m, 3H), 7.38 (m, 2H), 6.98 (m, 2H), 6.70 (m, 1H), 3.27 (t, 2H), 2.86 (t, 2H), 1.96 (m, 2H).

$C_{15}H_{15}N$ (MW=209); mass spectroscopy (MH+) 210.

Step C—Synthesis of 1-Chloromethylacetyl-8-phenyl-1,2,3,4-tetrahydroquinoline

The product from Step B (1.0 g, 4.78 mmol) was dissolved in CH$_2$Cl$_2$ (20 mL)/H$_2$O (20 mL) and treated with NaHCO$_3$ (0.602 g, 7.18 mmol) followed by chloroacetyl chloride (0.478 ml, 5.26 mmol). After stirring for 17 h at 23° C., the reaction was diluted with CH$_2$Cl$_2$, washed with saturated NaHCO$_3$, dried over Na$_2$SO$_4$ and purified by SiO$_2$ chromatography (CHCl$_3$/Hexanes 9:1). The product was isolated as a colorless solid.

Physical data were as follows:

C$_{17}$H$_{16}$ClNO (MW=286.77); mass spectroscopy (MH+) 287.

Anal. Calcd for C$_{17}$H$_{16}$ClNO; C, 71.45 H, 5.64 N, 4.90. Found: C, 71.63 H, 5.60 N, 4.87.

Step D—Synthesis of 5,6-Dihydro-4H-quino[8,1-ab][3]benzazepin-8(9H)-one

The product from Step C (0.89 g, 3.11 mmol) was mixed thoroughly with AlCl$_3$ (0.87 g, 6.54 mmol) at 23° C. and the mixture heated neat at 100° C. for 5–7 minutes. After vigorous gas evolution, the molten mixture was allowed to cool and extracted with several portions of CH$_2$Cl$_2$/NaHCO$_3$ (sat). The combined organic layers were dried over Na$_2$SO$_4$ and the title compound was purified by chromatography (SiO$_2$, CHCl$_3$/hexanes 9:1), yielding a colorless oil which solidified upon standing.

Physical data were as follows:

C$_{17}$H$_{15}$NO (MW=249.312); mass spectroscopy (MH+) 250.

Anal. Calcd for C$_{17}$H$_{15}$NO; C, 81.90 H, 6.06 N, 5.62. Found: C, 81.75 H, 6.11 N, 5.86.

Step E—Synthesis of 9-Oximo-5,6-Dihydro-4H-quino[8,1-ab][3]benzazepin-8(9H)-one

The product from Step D (0.490 g, 1.97 mmol) was dissolved in THF and butyl nitrite (0.46 mL, 3.93 mmol) and treated with KHMDS (0.5 M, 4.52 mL, 2.26 mmol) at 0° C. After stirring for 1 h, the reaction was quenched with cold 1 N HCl, extracted with EtOAc, the combined organic layers dried over Na$_2$SO$_4$ and the product purified by SiO$_2$ chromatography (CHCl$_3$/MeOH, 99:1). The title compound was isolated as a colorless solid.

Physical data were as follows:

C$_{17}$H$_{14}$N$_2$O$_2$ (MW=278.3); mass spectroscopy (MH+) 279.

Anal. Calcd for C$_{17}$H$_{14}$N$_2$O$_2$.0.3317 mol H$_2$O; C, 71.82 H, 5.19 N, 9.85. Found: C, 71.85 H, 5.09 N, 9.59.

Step F—Synthesis of 9-Amino-5,6-Dihydro-4H-quino[8,1-ab][3]benzazepin-8(9H)-one

The product from Step E (0.360 g, 1.29 mmol) was hydrogenated over Ra/Ni (0.05 g) in EtOH (50 mL)/ NH$_3$ (anhydrous) (5.0 mL) at 100° C. and 500 psi for 10 h. The catalyst was removed by filtration and the resulting filtrate chromatographed over SiO$_2$ (CHCl$_3$/MeOH, 98:2) yielding the titled compound as a colorless oil which solidified upon standing.

Physical data were as follows:

C$_{17}$H$_{16}$N$_2$O (MW=264.326); mass spectroscopy (MH+) 266.

Anal. Calcd for C$_{17}$H$_{16}$N$_2$O; C, 77.25 H, 6.10 N, 10.60. Found: C, 77.23 H, 6.15 N, 10.49.

Example 35

Synthesis of 9-(N'-L-Alaninyl)amino-5,6dihydro-4H-quino[8,1-ab][3]benzazepin-8(9H)-one Hydrochloride Step A—Synthesis of 9-(N'-Boc-L-Alaninyl)amino-5,6-Dihydro-4H-quino[8,1-ab][3]benzazepin-8(9H)-one Following General Procedure D and using N-Boc-Alanine (Aldrich) and 9-amino-5,6-dihydro-4H-quino[8,1-ab][3]benzazepin-8(9H)-one (from Example 34), the title compound was prepared.

Physical data were as follows:

C$_{25}$H$_{29}$N$_3$O$_4$ (MW=435.521); mass spectroscopy: (MH+) 436.

Anal. Calcd for C$_{25}$H$_{29}$N$_3$O$_4$.0.4102 mol H$_2$O; C, 67.79 H, 6.79 N, 9.49;

Found: C, 67.83 H, 6.91 N, 9.29.

Step B—Synthesis of 9-(N'-L-Alaninyl)amino-5,6-dihydro-4H-quino[8,1-ab][3]benzazepin-8(9H)-one Hydrochloride Following General Procedure E and using the product from Step A, the title compound was prepared.

Physical data were as follows:

C$_{20}$H$_{21}$N$_3$O$_2$HCl (MW=371.6); mass spectroscopy (MH+ free base) 335.

Example 36

Synthesis of 7-Amino-1,3,4,7,12,12a-hexahydropyrido[2,1-b][3]benzazepin-6(2H)-one Step A—Synthesis of N-Chloroacetyl-2-benzylpiperidine Following General Procedure F and using 2-benzylpyridine, the title compound was prepared.

Physical data were as follows:

(MW=251.8); mass spectroscopy (MH+) 252.0.

Step B—Synthesis of 1,3,4,7,12,12a-hexahydropyrido[2,1-b][3]benzazepin-6(2H)-one Following General Procedure G and using N-chloroacetyl-2-benzylpiperidine, the title compound was prepared.

Physical data were as follows:

$^1$H-nmr (CDCl$_3$): δ=1.3–1.9 (6H); 2.42 (t, 1H); 3.08 (m, 2H); 3.47 (m, 1H); 3.96 (q, 2H); 4.66 (d, 1H); 7.2 (m, 4H).

(MW=215.3); mass spectroscopy (MH+) 216.1.

Step C—Synthesis of 7-Oximo-1,3,4,7,12,12a-hexahydropyrido[2,1-b][3]benzazepin-6(2H)-one Following General Procedure A (Step B) and using 1,3,4,7,12,12a-hexahydropyrido[2,1-b][3]benzazepin-6(2H)-one (from Step B), the title compound was prepared.

Physical data were as follows:

(MW=244.3); mass spectroscopy (MH+) 245.0.

Step D—Synthesis of 7-Amino-1,3,4,7,12,12a-hexahydropyrido[2,1-b][3]benzazepin-6(2H)-one Following General Procedure A (Step C) and using 7-oximo-1,3,4,7,12,12a-hexahydropyrido[2,1-b][3]benzazepin-6(2H)-one (from Step C), the title compound was prepared.

Physical data were as follows:

$^1$H-nmr (CDCl$_3$): δ=1.3–1.9 (6H); 2.42 (t, 1H); 3.08 (m, 2H); 3.47 (m, 1H); 3.96 (q, 2H); 4.66 (d, 1H); 7.2 (m, 4H).

(MW=230.3); mass spectroscopy (MH+) 231.1.

Example 37

Synthesis of 1-(N'-L-Alaninyl)amino-4,5,6,7-tetrahydro-3,7-methano-3H-3-benzazonin-2(1H)-one Step A—Synthesis of N-Chloroacetyl-3-phenylpiperidine Following General Procedure F and using 3-phenylpyridine hydrochloride (Aldrich), the title compound was prepared.

Step B—Synthesis of 4,5,6,7-Tetrahydro-3,7-methano-3H-3-benazonin-2(1H)-one

Following General Procedure G and using N-chloroacetyl-3-phenylpiperidine, the title compound was prepared.

Physical data were as follows:

$^1$H-nmr (CDCl$_3$): d=1.32–1.57 (2H); 2.08 (m, 2H); 2.81 (t, 1H); 3.13 (bs, 1H); 3.37 (m, 2H); 4.36 (m, 2H); 4.50 (d, 1H).

(MW=201.3); mass spectroscopy (MH+) 202.1.

Step C—Synthesis of 1-Oximo-4,5,6,7-tetrahydro-3,7-methano-3H-3-benzazonin-2(1H)-one Following General Procedure A (Step B) and using the product from Step B, the title compound was prepared.

Step D—Synthesis of 1-Amino-4,5,6,7-tetrahydro-3,7-methano-3H-3-benzazonin-2(1H)-one Following General Procedure A (Step C) and using the product from Step C', the title compound was prepared.

Physical data were as follows:

$^1$H-nmr (CDCl$_3$): δ=2.86 (t, 1H); 3.17 (bs, 1H); 3.39 (dd, 1H); 4.40 (d, 1H); 4.50 (d, 1H); 5.39 (s, 1H).

(MW=216.3); mass spectroscopy (MH+) 217.4.

Step E—Synthesis of 1-(N'-Boc-L-Alaninyl)amino-4,5,6,7-tetrahydro-3,7-methano-3H-3-benzazonin-2(1H)-one Following General Procedure D and using N-tert-Boc-L-alanine (Aldrich) and the product from Step D, the title compound was prepared.

Physical data were as follows:

(MW=387.48); mass spectroscopy (MH+) 388.1.

Step F—Synthesis of 1-(N'-L-Alaninyl)amino4,5,6,7-tetrahydro-3,7-methano-3H-3-benzazonin-2(1H)-one Following General Procedure E and using the product from Step E, the title compound was prepared.

Physical data were as follows:

$^1$H-nmr (CDCl$_3$): δ=2.85 (t, 1H); 3.16 (bs, 1H); 3.40 (dd, 1H); 3.67 (m, 1H); 4.35 (d, 1H); 4.56 (d, 1H); 6.40 (d, 1H).

(MW=287.4); mass spectroscopy (MH+) 288.1.

Example 38 Omitted

Example 39

Synthesis of 1,3-Dihydro-3-amino-1-methyl-4-phenyl-(2H)-1,5-benzodiazepin-2-one

Step A—Synthesis of 1,3-Dihydro-4-phenyl-(2H)-1,5-benzodiazepin-2-one (CAS No. 16439-95-5)

The following procedure is adapted from G. Vemin et al., *Chemica Scripta* 1980, 16, 157–162. A mixture of 1,2-phenylenediamine (5.00 g, 46.2 mmol, Aldrich) and ethyl benzoylacetate (9.77 g, 50.8 mmol, Aldrich) in toluene (150 mL) was heated to reflux for 4 hours, while removing water with a Dean-Stark trap. Upon cooling to ambient temperature, the product crystallized and was collected by filtration. The precipitate was rinsed with toluene (100 mL) to afford the title intermediate (8.0 g, 73%) as an off-white solid, m.p. 208–209° C.

Physical data were as follows:

$C_{15}H_{12}N_2O$ (MW=236.27), mass spectroscopy, MH+ 237.2.

Analytical for $C_{15}H_{12}N_2O$: Theory, C, 76.25; H, 5.12; N, 11.86. Found, C, 76.52; H, 4.96; N, 11.75.

$^1$H-NMR (CDCl$_3$, 250 MHz): δ=9.39 (bs, 1H), 8.08–8.11 (m, 2H), 7.51–7.45 (m, 4H), 7.27–7.18 (m, 2H), 7.13–7.09 (m, 1H), 3.56 (s, 2H).

Step B—Synthesis of 1,3-Dihydro-1-methyl-4-phenyl-(2H)-1,5-benzodiazepin-2-one (CAS No. 58876-61-2)

To a solution of the product from Step A (6.00 g, 25.4 mmol) in DMF (120 mL) was added cesium carbonate (9.11 g, 27.9 mmol) and iodomethane (1.74 mL, 27.9 mmol). The mixture was stirred at ambient temperature overnight, then diluted with EtOAc (300 mL) and washed with water (200 mL). The organic layer was dried over Na$_2$SO$_4$, filtered, and concentrated. HPLC purification eluting with hexanes/EtOAc (6:4) afforded the title intermediate 5.80 g (92%) as a yellow oil.

Physical data were as follows:

$C_{16}H_{14}N_2O$ (MW=250.30), mass spectroscopy, MH+ 251.1.

Analytical for $C_{16}H_{14}N_2O$: Theory, C, 76.78, H, 5.64, N, 11.19. Found, C, 76.97, H, 5.34, N, 11.11.

$^1$H-NMR (CDCl$_3$, 300 MHz): δ=8.16–8.10 (m, 2H), 7.50–7.42 (m, 4H), 7.33–7.23 (m, 3H), 4.14 (bd, 1H, J=10.25 Hz), 3.38 (s, 3H), 2.99 (bd, 1H, J=11.71 Hz).

Step C—Synthesis of 1,3-Dihydro-3-oximido-1-methyl-4-pheny-(2H)-1,5-benzodiazepin-2-one This step was conducted using the general procedure of G. A. Showell et al., *J. Med. Chem.* 1994, 37, 719. To a solution of the product from Step B (1.0 g, 4.0 mmol) in toluene (32 mL) at −20° C. was added potassium t-butoxide (1.12 g, 10.0 mmol) in two portions. The resulting orange solution was stirred for 20 minutes, then isoamyl nitrite (0.64 mL, 4.8 mmol) was added and the solution stirred for an additional 5 hrs at −20° C. The reaction was quenched with H$_2$O (8 mL) containing citric acid (840 mg). After 10 minutes, Et$_2$O (8 mL) was added and the suspension stirred at ambient temperature overnight. The mixture was diluted with EtOAc (200 mL) and washed with water (100 mL). The organic layer was dried over Na$_2$SO$_4$, filtered, and concentrated. HPLC purification eluting with hexanes /EtOAc (1:1) afforded the title intermediate (1.10 g, 98%) as a yellow solid exhibiting an ~10:1 mixture of oxime isomers, m.p. 233–234° C.

Physical data were as follows:

$C_{16}H_{13}N_3O_2$ (MW 279.30), mass spectroscopy, MH+ 280.2, MH− 278.2.

Analytical for $C_{16}H_{13}N_3O_2$: Theory, C, 68.81; H, 4.69; N, 15.04. Found, C, 68.79; H, 4.69; N, 14.77.

$^1$H NMR (D$_6$-DMSO, 300 MHz): δ=12.26 (bs, 1H), 7.91–7.88 (m, 2H), 7.58–7.48 (m, 5H), 7.40–7.30 (m, 2H), 3.38 (s, 3H).

Step D—Synthesis of 1,3-Dihydro-3-(oximido-ethyl-carbamoyl)-1-methyl-4-phenyl-(2H)-1,5-benodiazepin-2-one To a solution of the product from Step C (1.14 g, 4.08 mmol) in CH$_2$Cl$_2$ (50 mL) was added Et$_3$N (568 μL, 4.08 mmol) followed by ethyl isocyanate (387 μL, 4.89 mmol) and the solution stirred at ambient temperature overnight. Then the solution was diluted with CH$_2$Cl$_2$ (200 mL) and washed with water (100 mL). The organic layer was dried over Na$_2$SO$_4$, filtered, and concentrated. HPLC purification eluting with hexanes/EtOAc (1:1) afforded the title intermediate (1.30 g, 92%) as an ~4:1 mixture of oxime isomers as pale yellow solid, m.p. 178–179° C.

Physical data were as follows:

$C_{19}H_{18}N_3O_3$ (MW 350.38), mass spectroscopy, MH− 351.5.

Analytical for $C_{19}H_{18}N_4O_3$: Theory, C, 65.13; H, 5.18; N, 15.99. Found, C, 65.41; H, 5.27; N, 16.03.

¹H-NMR (CDCl₃, 300 Mhz) (major isomer): δ=7.98–7.95 (m, 2H), 7.53–7.44 (m, 4H), 7.32–7.28 (m, 3H), 5.88 (bt, 1H, J=5.09 Hz), 3.48 (s, 3H), 3.28–3.16 (m, 2H), 1.10 (t, 3H, J=7.1 Hz).

Step E—Synthesis of 1,3-Dihydro-3-amino-1-methyl-4-phenyl-(2H)-5-benzodiazepin-2-one To a stirred mixture of the product from Step D (2.5 g, 7.1 mmol) in glacial AcOH (44 mL), H₂O (22 mL) and MeOH (64 mL) was added zinc dust (1.76 g, 26.9 mmol). The reaction mixture stirred for 1 hour at room temperature, monitoring by TLC. The reaction mixture was poured into aq. 1N HCl (100 mL), and further diluted with water (100 mL), then washed with EtOAc (100 mL). The aqueous layer was made basic (to pH ~9–10) with 2N aq. NaOH and the product extracted into cold EtOAc (200 mL). The organic layer was dried over Na₂SO₄, filtered, and concentrated to give 1.28 g (55%) of the title intermediate as a light orange solid.

Physical data were as follows:

$C_{16}H_{15}N_3O$ (MW 265.32), mass spectroscopy, $MH^+$ 266.1.

Example 40

Synthesis of 1,3-Dihydro-3-(L-alaninyl)-amino-1-methyl-4-phenyl-(2H)-1,5-benzodiazepin-2-one Hydrochloride Step A—Synthesis of 1,3-Dihydro-3-[N'-(t-butoxycarbonyl)-L-alaninyl]-amino-1-methyl-4-phenyl-(2H)-1,5-benzodiazepin-2-one To a solution of the product from Example 39, Step E (0.720 g, 2.7 mmol) in THF (20 mL) was added (L)-Boc-alanine (0.588 g, 2.98 mmol), HOBT (0.403 g, 2.98 mmol), EDC (0.573 g, 2.98 mmol), and N,N-diisopropylethylamine (0.52 mL, 2.98 mmol). The resulting mixture was stirred at ambient temperature overnight. The reaction mixture was diluted with EtOAc (100 mL), then washed with H₂O (100 mL), 1M aq. K₂CO₃ (50 mL), and brine (50 mL). The organic layer was dried over Na₂SO₄, filtered, and concentrated. HPLC purification eluting with hexanes/EtOAc (6:4) afforded 700 mg (60%) of the title intermediate as a yellow solid, m.p. 90–91° C.

Physical data were as follows:

$C_{24}H_{28}N_4O_4$ (MW 436.51), mass spectroscopy, $MH^+$ 437.3, $MH^-$ 435.4.

5 Anal. Calcd. for $C_{24}H_{28}N_4O_4$: Theory, C; 66.04; H, 6.47; N, 12.84. Found, C, 65.91; H, 6.60; N, 12.70.

Step B—Synthesis of 1,3-Dihydro-3-(L-alaninyl)-amino-1-methyl-4-phenyl-(2H)-1,5-benzodiazepin-2-one Hydrochloride Through a solution of the product from Step A (1.5 g, 3.5 mmol) in 1,4-dioxane (200 mL) was passed a stream of HCl gas for 5 minutes. The reaction flask was capped and the solution stirred overnight at ambient temperature. The solution was concentrated to give 0.5 g (39%) of the title intermediate as a white solid, m.p. 196–198° C.

Physical data were as follows:

$C_{19}H_{21}N_4O_2Cl$ (MW 372.85), mass spectroscopy, $MH^+$ (minus HCl) 337.2, $MH^-$ (minus HCl) 335.

Exact Mass. Calcd. for :$C_{19}H_{21}N_4O_2$: Theory 337.1664, Found .337.1650

Example 41

Synthesis of 1,3,4,5-Tetrahydro-3-amino-1-methyl-4-phenyl-(2H)-1,5-benzodiazepin-2-one To a mixture of 10% Pd/C (200 mg) in EtOH (15 mL) was added the product from Example 39, Step D (200 mg, 0.571 mmol) and the vessel atmosphere charged with hydrogen via a balloon. The reaction mixture was stirred overnight at ambient temperature. The mixture was filtered through Celite and the filtrate concentrated to afford 144.0 mg (95%) of the title intermediate as a pale yellow amorphous solid.

Physical data were as follows:

$C_{13}H_{17}N_3O$ (MW 267.330)

Exact Mass. Calcd. for $C_{16}H_{18}N_3O_2$: Theory 268.1450, Found 268.1432.

Example 42

Synthesis of 1,3,4,5-Tetrahydro3-(L-alaninyl)-amino-1-methyl-4-phenyl-(2H)-1,5-benzodiazepin-2-one Hydrochloride Step A—Synthesis of 1,3,4,5-Tetrahydro-3-[N'-(t-butoxycarbonyl)-L-alaninyl]-amino-1-methyl-4-phenyl-(2H)-1,5-benzodiazepin-2-one To a solution of the product from Example 41 (1.5 g, 5,6 mmol) in THF (100 mL) was added (L)-Boc-alanine (1.15 g, 6.2 mmol), HOBT (0.831 g, 6.2 mmol), EDC (1.18 g, 6.2 mmol), and N,N-diisopropylethylamine (1.07 ml, 6.2 mmol). The resulting mixture was stirred at ambient temperature overnight. The mixture was diluted with EtOAc (200 mL) and washed with H₂O (200 mL). The organic layer was dried over Na₂SO₄, filtered, and concentrated. HPLC purification eluting with hexanes/EtOAc (6:4) afforded 1.2 g (49%) of the title intermediate as a white solid, m.p. 92–93° C.

Physical data were as follows:

$C_{24}H_{30}N_4O_4$ (MW 438.525), mass spectroscopy, $MH^+$ 439.2.

Exact Mass. Calcd. for $C_{24}H_{31}N_4O_4$: Theory 439.2345, Found .439.2325

Step B—Synthesis of 1,3,4,5-Tetrahydro3-(L-alaninyl)-amino-1-methyl-4-phenyl-(2H)-1,5-benzodiazepin-2-one Hydrochloride Through a solution of the product from Step A (1.2 g, 2.7 mmol) in 1,4-dioxane (200 mL) was passed a stream of HCl gas for 5 minutes. The reaction flask was capped and the solution stirred overnight at ambient temperature. The solution was concentrated to give 1.0 g (100%) of the title intermediate as a white solid, m.p 200–202° C.

Physical data were as follows:

$C_{19}H_{23}N_4O_2Cl$ (MW 374.870), mass spectroscopy, $MH_+$ 375.3, $MH^-$ 373.2.

Exact Mass. for :$C_{19}H_{23}N_4O_2$: Theory 339.1821, Found 339.1824.

Example 43

Synthesis of 1,3-Dihydro-3-amino-1-methyl-4-isopropyl-(2H)-1,5benzodiazepin-2-one Step A—Synthesis of 1,3-Dihydro-4-isopropyl-(2H)-1,5-benzodiazepin-2-one The following procedure is adapted from G. Vernin et al., *Chemica Scripta* 1980, 16, 157–162. A mixture of 1,2-phenylenediamine (1.86 g, 17.2 mmol, Aldrich) and ethyl isobutylracetate (3.0 g, 18.9 mmol, Aldrich) in toluene (80 mL) was heated to reflux under nitrogen for 4 hours, while removing water with a Dean-Stark trap. Upon cooling to ambient temperature, the product crystallized and was collected by filtration, rinsing with toluene (100 mL), then slurried in Et₂O and filtered to give 2.16 g (62%) of the title intermediate as an off-white solid, m.p. 167–168° C.

Physical data were as follows:

$C_{12}H_{14}N_2O$ (MW 202.26), mass spectroscopy, MH⁺203.1.

Analytical for $C_{12}H_{14}N_2O$: Theory, C, 71.26, H, 6.97, N, 13.85. Found, C, 71.13, H, 6.67, N, 14.06.

¹H-NMR (D₆-DMSO, 300 MHz): δ=10.33 (bs, 1H), 7.24–7.10 (m, 4H), 3.03 (s, 2H), 2.77 (septet, 1H, J=6.86), 1.16 (d, 6H, J=6.59 Hz).

Step B—Synthesis of 1,3-Dihydro-1-methyl-4-isopropyl-(2H)-1,5-benzodiazepin-2-one To a solution of the product from Step A (2.18 g, 10.8 mmol) in DMF (20 mL) was added cesium carbonate (3.87 g, 11.8 mmol), and iodomethane (0.74 mL, 11.8 mmol). The mixture was stirred at ambient temperature overnight, then diluted with EtOAc (200 mL), and washed with water (100 mL). The organic layer was dried over Na₂SO₄, filtered, and concentrated. HPLC purification eluting with hexanes/EtOAc (3:7) afforded 1.90 g (88%) of the title intermediate as a yellow oil. Physical data were as follows:

$C_{13}H_{16}N_2O$ (MW 216.282), mass spectroscopy, MH⁺ 217.1.

Exact Mass. for $C_{13}H_{17}N_2O$: Theory 217.1341; Found, 217.1327.

¹H-NMR (CDCl₃, 300 MHz): δ=7.30–7.15 (m, 4H), 3.49 (bd, 1H, J=11.71 Hz), 3.36 (s, 3H), 2.81 (septet, 1H, J=6.83 Hz), 2.74 (bd, 1H, J=12.81 Hz), 1.24 (bd, 6H, J=6.22 Hz).

Step C—Synthesis of 1,3-Dihydro-3-oximido-1-methyl-4-isopropyl-(2H)-1,5-benzodiazepin-2-one This step was conducted following the general procedure of G. A. Showell et al., *J Med. Chem.* 1994, 37, 719. To a solution of the product from Step C (1.0 g, 4.9 mmol) in toluene (30 mL) at −20° C. was added potassium t-butoxide (1.38 g, 12.3 mmol) in two portions. The resultant pale yellow solution was stirred at −20° C. for 20 minutes, then allowed to warm to 0° C. with stirring for 5 minutes. Isoamyl nitrite (0.80 mL, 5.9 mmol) was added to the orange solution and the solution stirred at −20° C. for an additional 5 hrs. The reaction quenched with H₂O (8 mL) containing citric acid (840 mg) and stirred 10 minutes allowing the mixture to warm. Then, Et₂O (8 mL) was added and the suspension stirred at ambient temperature overnight. The mixture was diluted with EtOAc (200 mL) and washed with water (100 mL). The organic layer was dried over Na₂SO₄, filtered, and concentrated. HPLC purification eluting with hexanes/EtOAc (3:7) afforded 760 mg (63%) of the title intermediate as an ~3:1 mixture of oxime isomers, and as a pale yellow solid, m.p. 140–144° C.

Physical data were as follows:

$C_{13}H_{15}N_3O_2$ (MW 245.28), mass spectroscopy, MH⁺ 246.3, MH⁻244.4

Exact Mass.for $C_{13}H_{16}N_3O_2$: Theory 246.1243; Found 246.1237

¹H-NMR (D₆-DMSO, 300 Mhz) (major isomer): δ=12.25 (s, 1H), 7.51–7.44 (m, 1H), 7.33–7.21 (m, 3H), 3.35 (s, 3H), 3.14 (septet, 1H, J=6.95 Hz), 1.24 (d, 3H, J=6.59), 1.12 (d, 3H, J=7.32).

Step D—Synthesis of 1,3-Dihydro-3-(oximido-ethyl-carbamoyl)-1-methyl-4-isopropyl-(2H)-1,5-benzodiazepin-2-one To a solution of the product from Step C (4.0 g, 16.3 mmol) in CH₂Cl₂ (200 mL) was added Et₃N (2.73 mL, 19.6 mmol) followed by ethyl isocyanate (1.55 mL, 19.6 mmol) and the solution stirred at ambient temperature overnight. The solution was diluted with CH₂Cl₂ (300 mL), and washed with water (150 mL ) then brine (150 mL). The organic layer was dried over Na₂SO₄, filtered, and concentrated. The resulting solid was slurried in Et₂O/hexanes (1:1) and collected by vacuum filtration washing with Et₂O/hexanes (1:1, 100 mL) to afford 3.51 g (68%) of the title intermediate as a white solid, m.p. 177–179° C.

Physical data were as follows:

$C_{16}H_{20}N_4O_3$ (MW 316.36), mass spectroscopy, MH⁺ 317.1.

Analytical for $C_{16}H_{20}N_4O_3$: Theory, C, 60.75; H; 6.37; N, 17.71. Found, C; 60.67; H; 6.37; N, 17.47.

Step E—Synthesis of 1,3-Dihydro-3-amino-1-methyl-4-isoproyl-(2H)-1,5-benodiazepin-2-one To a stirred mixture of the product from Step D (2.0 g, 7.57 mmol) in glacial AcOH (44 mL), H₂O (22 mL), and MeOH (64 mL) was added zinc dust (1.77 g, 27.0 mmol). The reaction mixture stirred for 1 hour at room temperature, monitoring by TLC. The reaction mixture was diluted with 1N aq. HCl (100 mL) and water (100 mL), then washed with EtOAc (100 mL). Aqueous layer made basic to pH ~9–10 with 2N aq. NaOH and the product extracted into cold EtOAc (200 mL). The organic layer was dried over Na₂SO₄, filtered, and concentrated to give 1.06 g (61%) of the title intermediate as a tan solid.

Physical data were as follows:

$C_{13}H_{17}N_3O$ (MW 231.297), mass spectroscopy, MH⁺ 232.1.

Exact Mass. Calcd. for $C_{13}H_{18}N_3O_2$: Theory 232.1450, Found 232.1448.

Example 44

Synthesis of 1,3-Dihydro-3-(L-alaninyl)-amino-1-methyl-4-isopropyl-(2H)-1,5-benzodiazepin-2-one Hydrochloride Step A—Synthesis of 1,3-Dihydro-3-[N'-(t-butxycarbonyl)-L-alaninyl]-amino-1-methyl-4-isopropyl-(2H)-1,5-benzodiazepin-2-one To a solution of the product from Example 43, Step E (1.06 g, 5.0 mmol) in THF (100 mL) was added (L)-Boc-alanine (944 mg, 5.0 mmol), HOBT (682 mg, 5.0 mmol), EDC (968 mg, 5.0 mmol), and N,N-diisopropylethylamine (0.88 ml, 5.0 mmol). The resulting mixture was stirred at ambient temperature overnight. The mixture was diluted with EtOAc (200 mL) then washed with H₂O (200 mL), 1M aq. K₂CO₃ (100 mL), and brine (100 mL). The organic layer was dried over Na₂SO₄, filtered, and concentrated. HPLC purification eluting with hexanes/EtOAc (6:4) afforded 1.45 g (74%) of the title intermediate as a thick yellow oil.

Physical data were as follows:

$C_{21}H_{30}N_4O_4$ (MW 402.492), mass spectroscopy, MH⁺403.4.

Exact Mass. Calcd. for $C_{21}H_{31}N_4O_4$: Theory 403.2345, Found 403.2343.

Step B—Synthesis of 1,3-Dihydro-3-(L-alaninyl)-amino-1-methyl-4-isopropyl-(2H)-1,5-benzodiazepin-2-one Hydrochloride Through a solution of the product from Step B (1.35 g, 3.47 mmol) in 1,4-dioxane (200 mL) was passed a stream of HCl gas for 5 minutes. The reaction flask was capped and the solution stirred overnight at ambient temperature. The solution was concentrated to give 480 mg (41%) of the title intermediate as a white solid, m.p 190–196° C.

Physical data were as follows:

$C_{16}H_{23}N_4O_2Cl$ (MW 338.837), mass spectroscopy, $MH^+$ 303.2 (minus HCl).

Analytical for :$C16H_{23}N_4O_2Cl.5H_2O$ Theory, C;55.24; H, 6.95; N, 16.10. Found, C; 55.12; H, 6.60; N, 15.59.

Exact Mass. for :$C_{16}H_{23}N_4O_2$: Theory 303.1821, Found 303.1803.

Example 45

Synthesis of 1,3,4,5-tetrahydro-3-amino-1-methyl-4-isopropyl-(2H)-1,5-benzodiazepin-2-one To a suspension of 10% Pd/C (900 mg) in EtOH (160 mL) was added the product from Example 43, Step D (1.6 g, 6.9 mmol) and the flask charged with a hydrogen atmosphere via a balloon. The reaction mixture was stirred overnight at ambient temperature. Then filtered through Celite and the filtrate concentrated to give 1.19 g (70%) of the title intermediate as a pale yellow oil.

Physical data were as follows:

$C_{13}H_{19}N_3O$ (MW 233.313).

Exact Mass. Calcd. for $C_{13}H_{20}N_3O_2$: Theory 234.1606, Found 234.1583.

Example 46

Synthesis of 1,3,4,5-Tetrahydro-3-(L-alaninyl)-amino-1-methyl-4-isopropyl-(2H)-1,5-benzodiazepin-2-one Hydrochloride Step A—Synthesis of 1,3,4,5-Tetrahydro-3-[N'-(t-butoxycarbonyl)-L-alaninyl]-amino-1-methyl-4-isopropyl-(2H)-1,5-benzodiazepin-2-one To a solution of the product from Example 45 (1.09 g, 4.6 mmol) in THF (75 mL) was added (L)-Boc-alanine (960 mg, 5.1 mmol), HOBT (693 mg, 5.1 mmol), EDC (985 mg, 5.1 mmol), and N,N-diisopropylethylamine (897 μl, 5.1 mmol). The resulting mixture was stirred ambient temperature overnight. The mixture was diluted with EtOAc (200 mL), then washed with $H_2O$ (200 mL). The organic layer was dried over $Na_2SO_4$, filtered, and concentrated. HPLC purification eluting with hexanes/EtOAc (6:4) afforded 1.5 g (80%) of the title intermediate as a white solid, m.p. 194–195° C.

Physical data were as follows:

$C_{21}H_{32}N_4O_4$ (MW 403.508), mass spectroscopy, $MH^+$ 405.5.

Analytical for $C_{21}H_{32}N_4O_4$: Theory, C; 62.35, H; 7.97, N, 13.85. Found, C; 62.62, H; 7.80, N, 14.14.

Step B—Synthesis of 1,3,4,5-Tetrahydro-3-(L-alaninyl)-amino-1-methyl-4-isopropyl-(2H)-1,5-benzodiazepin-2-one Hydrochloride Through a solution of the product from Step A (1.5 g, 3.7 mmol) in 1,4-dioxane (200 mL) was passed a stream of HCl gas for 5 minutes. The reaction flask was capped and the solution stirred overnight at ambient temperature. The solution was concentrated to give 0.9 g (71%) of the title intermediate as a white solid, m.p. 202–203° C.

Physical properties were as follows:

$C_{16}H_{25}N_4O_2Cl$ (MW 340.853), mass spectroscopy, $MH^+$ (minus HCl) 305.2.

Exact Mass. Calcd. for $C_{16}H_{25}N_4O_2$: Theory 305.1997, Found 305.1967.

Example 47

Synthesis of 1,3-Dihydro-3-[(L)-norleucinyl]amino-1-methyl-4isopropyl-(2H)-1,5-benzodiazepin-2-one Hydrochloride Step A—Synthesis of 1,3-Dihydro-3-[N'-(t-butoxycarbonyl)-L-norleucinyl]-amino-1-methyl-4-isopropyl-(2H)-1,5-benzodiazepin-2-one To a solution of the product from Example 43, Step E (2.50 g, 10.8 mmol) in THF (200 mL) was added (L)-Boc-Nva-OH (2.58 g, 11.9 mmol, Bachem), HOBT (1.60 g, 11.9 mmol), EDC (2.28 g, 11.9 mmol), and N,N-diisopropylethylamine (2.07 mL, 11.9 mmol). The resulting mixture was stirred at ambient temperature overnight. The mixture was diluted with EtOAc (300 mL) and washed with 1N aq. HCl (100 mmL), 1M aq. $K_2CO_3$ (100 mL), and brine (100 mL). The organic layer was dried over $Na_2SO_4$, filtered, and concentrated. HPLC purification eluting with hexanes/EtOAc (6:4) afforded 3.20 g (69%) of the title intermediate as a pale yellow solid.

Physical data were as follows:

$C_{23}H_{34}N_4O_4$ (MW 430.546), mass spectroscopy, $MH^+$ 430.4, $MH^-$ 429.4

Exact Mass. Calcd. for $C_{23}H_{35}N_4O_4$: Theory 431.2658, Found 431.2658.

Step B—Synthesis of 1,3-Dihydro-3-[(L)-norleucinyl]-amino-1-methyl-4-isopropyl-(2H)-1,5-benzodiazepin-2-one Hydrochloride Through a solution of the product from Step A (1.35 g, 3.47 mmol) in 1,4-dioxane (200 mL) was passed a stream of HCl gas for 5 minutes. The reaction flask was capped and the solution stirred overnight at ambient temperature. The solution was concentrated to give 480 mg (41%) of the title intermediate as a white solid, m.p 190–196° C.

Physical data were as follows:

$C_{16}H_{23}N_4O_2Cl$ (MW 338.837), mass spectroscopy, $MH^+$ 303.2 (minus HCl).

Analytical for $C_{16}H_{23}N_4O_2Cl$ $0.5H_2O$: Theory, C, 55.24; H, 6.95; N, 16.10. Found, C, 55.12; H, 6.60; N, 15.59.

Exact Mass. For $C_{16}H_{23}N_4O_2$: Theory 303.1821, Found 303.1803.

Example 48

Synthesis of 1,3,4,5-Tetrahydro-3-[(L)-norleucinyl]-amino-1-methyl-4-isopropyl-(2H)-1,5-benzodiazepin-2-one Hydrochloride Step A—Synthesis of 1,3,4,5-Tetrahydro-3-[N'-(t-butoxycarbonyl-L-norleucinyl]-amino-1-methyl-4-isopropyl-(2H)-1,5-benzodiazepin-2-one To a solution of the product from Example 45 (1.62 g, 6.92 mmol) in THF (120 mL) was added (L)-Boc-Nva-OH (1.65 g, 7.60 mmol, Bachem), HOBT (1.03 g, 7.60 mmol), EDC (1.46 g, 7.6 mmol), N,N-diisopropylethylamine (1.32 mL, 7.6 mmol). The resulting mixture was stirred at ambient temperature overnight. The mixture was diluted with EtOAc (200 mL) and washed with $H_2O$ (200 mL). The organic layer was dried over $Na_2SO_4$, filtered, and concentrated. HPLC purification eluting with hexanes/EtOAc (6:4) afforded 1.74 g (58%) of the title intermediate as a white solid, m.p. 186–187° C.

Physical data were as follows:

$C_{23}H_{36}N_4O_4$ (MW 432.561), mass spectroscopy, $MH^+$ 433.4, $MH^-$ 431.4

Exact Mass. Calcd. for $C_{23}H_{37}N_4O_4$: Theory 433.2817, Found 433.2815.

Step B—Synthesis of 1,3,4,5-Tetrahydro-3-[(L)-norleucinyl]-amino-1-methyl-4-isopropyl-(2H)-1,5-benzodiazepin-2-one Hydrochloride Through a solution of the product from Step A (1.78 g, 4.1 mmol) in 1,4-dioxane (200 mL) was passed a stream of HCl gas for 5 minutes. The reaction flask was capped and the solution stirred overnight at ambient temperature. The solution was concentrated to give 1.43 g (95%) of the title intermediate as a white solid, m.p. 200–210° C.

Physical data were as follows:

$C_{18}H_{29}N_4O_2Cl$ (MW 368.906), mass spectroscopy, MH$^+$ 334.3 (minus HCl), MH$^-$ 333.2.(minus HCl).

Exact Mass. Calcd. for $C_{18}H_{29}N_4O_2$: Theory 333.2290, Found 333.2272.

Example 49

Synthesis of 1,3-Dihydro-3-(L-norleucinyl)-amino-1-methyl-4-phenyl-(2H)-1,5-benzodiazepin-2-one Hydrochloride Step A—Synthesis of 1,3-Dihydro-3-[N'-(t-butoxycarbonyl)-L-norleucinyl]-amino-1-methyl-4-phenyl-(2H)-1,5-benzodiazepin-2-one To a solution of the product from Example 39, Step E (2.35 g, 8.85 mmol) in THF (160 mL) was added (L)-Boc-Nva-OH (2.11 g, 9.73 mmol), HOBT (1.31 g, 9.73 mmol), EDC (1.86 g, 9.73 mmol), and N,N-diisopropylethylamine (1.70 mL, 9.73 mmol). The resulting mixture was stirred at ambient temperature overnight. The reaction mixture was diluted with EtOAc (480 mL), then washed with H$_2$O (160 mL), saturated NaHCO$_3$ (160 mL), and brine (160 mL). The organic layer was dried over Na$_2$SO$_4$, filtered, and concentrated. HPLC purification eluting with hexane/EtOAc (8:2 to 1:1) afforded 2.04 g of the title intermediate as a yellow foam (50% yield), m.p. 102–105° C.

Physical data were as follows:

Exact Mass, Calc. For $C_{25}H_{33}N_4O_4$:465.2502, found: 465.2502.

Step B—Synthesis of 1,3-Dihydro-3-(L-norleucinyl)-amino-1-methyl-4-phenyl-(2H)-1,5-benzodiazepin-2-one Hydrochloride Through a solution of the product from Step A (2.04 g, 4.39 mmol) in 1,4-dioxane (100 mL) was passed a stream of HCl gas for 15 minutes at 0° C. The reaction flask was capped and the solution stirred overnight at ambient temperature. The solution was concentrated to give 1.83 g of the title intermediate as a yellow solid, m.p.184–187° C.

Physical data were as follows:

Exact Mass. Calc. For $C_{21}H_{24}N_4O_3$: 365.1977, found: 365.1968.

Example 50

Synthesis of 3-Amino-1-methyl-5-phenyl-1,3,4,5-tetrahydro-(2H)-1,5-benzodiazepin-2-one Step A—Synthesis of 5-Phenyl-1,3,4,5-tetrahydro-(2H)-1,5-benzodiazepine-2-one (CAS. No. 32900-17-7)

Following the procedure described in WO 96/40653, PCT US 96/08331, Step 1-A using N-phenyl-1,2-phenylenediamine (Aldrich) and methyl acrylate (Aldrich), the title intermediate was prepared.

Physical data was as follows:

$C_{15}H_{14}N_2O$ (MW 238.29), Mass spectroscopy, MH$^+$ 239.2.

Anal. Calcd. for $C_{15}H_{14}N_2O$: C, 75.61; H, 5.92; N, 11.76. Found C, 75.88; H, 5.94; N, 11.69.

Step B—Synthesis of 1-Methyl-5-phenyl-1,3,4,5-tetrahydro-(2H)-1,5-benzodiazepine-2-one Following the General Procedure J using the product from Step A and methyl iodide (Aldrich), the title intermediate was prepared. HPLC purification eluting with EtOAc/hexanes (1:1) afforded the title intermediate as a light pink solid.

Physical data were as follows:

$C_{16}H_{16}N_2O$ (MW 252.32), Mass spectroscopy, MH$^+$ 253.2

Anal. Calcd. for $C_{16}H_{16}N_2O$: C, 76.16; H; 6.39; N, 11.10. Found C, 76.00; H, 6.19; N, 11.13.

Step C—Synthesis of 3-Azido-1-methyl-5-phenyl-1,3,4,5-tetrahydro-(2H)-1,5-benzodiazepine-2-one Following the General Procedure H using the product from Step B, the title intermediate was prepared. HPLC purification eluting with hexane/EtOAc (6:4) afforded a the title intermediate as a thick yellow oil.

Physical data were as follows:

$C_{16}H_{15}N_5O$ (MW 293.33), Mass spectroscopy, MH$^+$ 294.2.

Step D—Synthesis of 3-Amino 1-methyl-5-phenyl-1,3,4,5-tetrahydro-(2H)-1,5-benzodiazepine-2-one Following General Procedure I using the product from Step C, the title intermediate was prepared. The title intermediate was prepared as a thick yellow oil and used without further purification.

Physical data were as follows:

$C_{16}H_{17}N_3O$ (MW 267.33), Mass spectroscopy, MH$^+$ 268.4

Example 51

Synthesis of 3-(N'-L-Alaninyl)amino-1-methyl-5-phenyl-1,3,4,5-tetrahydro-(2H)-1,5-benzodiazepin-2-one Step A—Synthesis of 3-[N'-(t-Butoxycarbonyl)-L-alaninyl]-amino-1-methyl-5-phenyl-1,3,4,5-tetrahydro-(2H)-1,5-benzodiazepine-2-one Following General Procedure D with the product from Example 50, Step D and Boc-L-alanine (Nova Biochem), the title intermediate was prepared. HPLC purification eluting with CH$_2$Cl$_2$/MeOH (97:3) afforded the title intermediate as an amorphous white solid.

Physical data were as follows:

$C_{24}H_{30}N_4O_4$ (MW 438.52), Mass spectroscopy, MH$^+$ 439.2, MH$^-$ 437.4.

Anal. Calcd. for $C_{24}H_{30}N_4O_4$: C, 65.73; H, 6.90; N, 12.78. Found C, 65.70; H, 6.65; N, 12.48.

Step B—Synthesis of 3-(L-Alaninyl)-amino-1-methyl-5-phenyl-1,3,4,5-tetrahydro-(2H)-1,5-benzodiazepine-2-one Following General Procedure E using the product from Step A, the title intermediate was prepared. HPLC purification eluting with CH$_2$Cl$_2$/MeOH (95:5) afforded the title intermediate as a mixture of diastereomers. A second HPLC purification eluting with CH$_2$Cl$_2$/MeOH (99:1 gradient, raising the MeOH concentration by 1% every 10 minutes) afforded the separated diastereomers (isomer A and isomer B) as pale yellow solids.

Physical data were as follows:

First eluting isomer (isomer A):

$C_{19}H_{22}N_4O_2$ (MW 338.41), mass spectroscopy, 338.4.

Second eluting isomer (isomer B):

$C_{19}H_{22}N_4O_2$ (MW 338.41), mass spectroscopy, MH$^+$339.0.

Example 52

Synthesis of 3-(L-Valinyl)-amino-1-methyl-5-phenyl-1,3,4,5-tetrahydro-(2H)-1,5-benzodiazepin-2-one Step A—Synthesis of 3-[N'-(t-Butoxycarbonyl)-L-valinyl]-amino-1-methyl-5-phenyl-1,3,4,5-tetrahydro-(2H)-1,5-benzodiazepin-2-one Following General Procedure D using the product from Example 50 and Boc-L-valine (Nova Biochem), the title intermediate was prepared. HPLC purification eluting with hexanes/EtOAc (7:3) afforded the title intermediate as a white solid.

Physical data were as follows:

$C_{26}H_{34}N_4O_4$ (MW 466.58). mass spectroscopy, MH$^+$ 467.4, MH$^-$ 465.3.

Anal calcd. for $C_{26}H_{34}N_4O_4$: Theory, C, 66.93; H, 7.35; N, 12.01. Found, C, 66.79; H, 7.14; N, 11.76.

Step B—Synthesis of 3-(L-Valinyl)-amino-1-methyl-5-phenyl-1,3,4,5-tetrahydro-(2H)-1,5-benzodiazepin-2-one Following the General Procedure E using the product from Step A, the title compound was prepared. HPLC purification eluting with $CH_2Cl_2$/MeOH (95:5), and a second HPLC purification eluting with (99:1), afforded the individual isomers A (first eluting) and B (second eluting) of the title compound.

Physical data were as follows:

$C_{21}H_{26}N_4O_2$ (MW 366.46). mass spectroscopy MH$^+$ 367.2 (similar for both isomers).

First eluting isomer (A):

Anal calcd. for $C_{21}H_{26}N_4O_2$: Theory, C, 68.83; H, 7.15; N, 15.29. Found, C, 68.68; H, 7.06; N, 15.17.

Specific rotation in MeOH, 1 mL cell, 0.5% C at 589=+85.01°.

Second eluting isomer (B):

Exact mass anal calcd. for $C_{21}H_{27}N_4O_2$: Theory 367.2134. Found, 367.2120.

Specific rotation in MeOH, 1 mL cell, 0.5% C at 589=−17.52°.

Example 53

Synthesis of 3-[L-(O-Benzyl)-threoninyl]-amino-1-methyl-5-phenyl-1,3,4,5-tetrahydro-(2H)-1,5-benzodiazepin-2-one Step A—Synthesis of 3-[N'-(t-Butoxycarbonyl)-L-(O-benzyl)-threoninyl]-amino-1-methyl-5-phenyl-1,3,4,5-tetrahydro-(2H)-1,5-benzodiazepin-2-one Following General Procedure K using the product from Example 50 and Boc-O-benzyl-L-threonine (Sigma), the title intermediate was prepared. HPLC purification eluting with hexanes/EtOAc (4:1 to 3:1 gradient) afforded separation of the individual isomers, A and B, of the title intermediate.

Step B—Synthesis of 3-[L-(O-Benzyl)-threoninyl]-amino-1-methyl-5-phenyl-1,3,4,5-tetrahydro-(2H)-1,5-benzodiazepin-2-one Following General Procedure E using the individual isomers, A and B, from Step A, the title compound was prepared.

Physical data were as follows:

$C_{27}H_{30}N_4O_3$ (MW 458.56), mass spectroscopy, MH$^+$ 459.6, MH$^-$ 457.5 (similar for both isomers).

Product from isomer A:

Specific rotation in MeOH, 1 mL cell, 0.5% C at 589=−173.72°.

Product from isomer B:

Specific rotation in MeOH, 1 mL cell, 0.5% C at 589=+91.22°.

Example 54

Synthesis of 3-(S)-Phenylglycinyl]-amino-5-phenyl-1-methyl-1,3,4,5-tetrahydro-(2H)-1,5-benzodiazepine-2-one Step A—Synthesis of 3-[N'-(t-Butoxycarbonyl)-(S)-phenylglycinyl]-amino-1-methyl-5-phenyl-1,3,4,5-tetrahydro-(2H)-1,5-benzodiazepine 2-one Following modified General Procedure L using the product from Example 50 and Boc-L-Phenylglycine (Nova Biochem), the title intermediate was prepared. The modification was that the reaction was only stirred for 6 hours. HPLC purification eluting with 80/20 hexanes/EtOAc afforded the separated diastereomers; isomer 1 (first eluting) and isomer 2 (second eluting).

Physical data were as follows:

$C_{29}H_{32}N_4O_4$ (MW 500.60); mass spectroscopy for isomer 1: MH$^+$ 501.2; MH$^-$, 499.3; mass spectroscopy for isomer 2: MH$^+$ 501.2; MH$^-$, 499.3.

Step B—Synthesis of 3-((S)-Phenylglycinyl)-amino-1-methyl-5-phenyl-1,3,4,5-tetrahydro-(2H)-1,5-benzodiazepine 2-one Following the General Procedure E using the products (Isomers 1 and 2 brought through reaction sequence separately) from Step A, the title intermediates were prepared. HPLC purification eluting with 95/5 methylene chloride/methanol afforded the title intermediates as a light yellow oils.

Physical data were as follows:

$C_{24}H_{24}N_4O_2$ (MW 400.48); mass spectroscopy for isomer 1: MH$^+$, 401.3; MH$^-$, 399.2; mass spectroscopy for isomer 2: MH$^+$, 401.2; MH$^-$, 399.3.

Example 55

Synthesis of 3-Amino-1,5-bis-methyl-1,3,4,5-tetrahydro-(2H)-1,5-benzodiazepine-2-one Step A—synthesis of N,N'-Dimethyl-1,2-phenylenediamine (CAS No. 3213-79-4)

Following the literature procedures of H. Stetter, *Chem. Ber.*, 1953, 86, 161 and G. W. H. Cheeseman, *J. Chem. Soc.*, 1955, 3308, the title intermediate was prepared from 1,2-phenylenediamine (Aldrich) as a low melting solid.

Physical data was as follows:

$C_8H_{12}N_2$ (MW 136); mass spectroscopy, 136.1.

Exact mass anal. Cacld. for $C_8H_{13}N_2$: Theory, 137.1079, Found, 137.081

Step B—Synthesis of 1,5-Bis-methyl-1,3,4,5-tetrahydro-(2H)-1,5-benzodiazepine-2-one To a solution of the product from Step A (400 mg, 2.94 mmols) in 5M Aq. HCl (30 mL) was added acrylic acid (0.202 mL, 3.23 mmols, Aldrich) and the mixture heated to reflux for 18 hours. The black mixture was allowed to cool, then poured onto ice and the pH adjusted to 10 with 5M Aq. NaOH. The product was extracted into $CH_2Cl_2$ (200 mL) and washed with water (100 mL) and brine (100 mL). The organic phase was dried over $Na_2SO_4$, filtered, and concentrated to give a black oil. HPLC purification eluting with hexanes/EtOAc (1:1) afforded 364 mg of the title intermediate as a brown oil.

Physical data were as follows:

$C_{11}H_{14}N_2O$ (MW 190.25); mass spectroscopy, MH$^+$ 191.4.

Anal. Calcd. for $C_{11}H_{14}N_2O$: Theory, C, 69.45; H, 7.42; N, 14.72; Found, C, 69.26; H, 7.40; N, 14.64.

Step C—Synthesis of 3-Azido-1,5-bis-methyl-1,3,4,5-tetrahydro-(2H)-1,5-benzodiazepine-2-one Following General Procedure H using the product from Step B, the title intermediate was prepared. HPLC purification eluting with hexanes/EtOAc (7:3) afforded the title intermediate as a light brown oil.

Physical data were as follows:

$C_{11}H_{13}N_5O$ (MW 231.26), mass spectroscopy, MH+ 232.2

Exact mass Anal. Calcd. for $C_{11}H_{14}N_5O$: Theory, 232.1198; Found, 232.1196.

Step D—Synthesis of 3-Amino-1,5-bis-methyl-1,3,4,5-tetrahydro-(2H)-1,5-benzodiazepine-2-one Following General Procedure I using the product from Step C, the title intermediate was prepared and used without chromatographic purification.

Physical data were as follows:

$C_{11}H_{15}N_3O$ (MW 205.26), mass spectroscopy MH+ 206.2.

Exact mass Anal. Calcd. for $C_{11}H_{16}N_3O$: Theory, 206.1293; Found, 206.1295.

Example 56

Synthesis of 3-(L-Alaninyl)-amino-1,5-bis-methyl-1,3,4,5-tetrahydro-(2H)-1,5-benzodiazepine-2-one Step A—Synthesis of 3-[N'-(t-Butoxycarbonyl)-L-alaninyl]-amino-1,5-bis-methyl-1,3,4,5-tetrahydro-(2H)-1,5-benzodiazepine-2-one Following General Procedure D using the product from Example 55 and Boc-L-alanine (Nova Biochem), the title intermediate was prepared. HPLC purification eluting with EtOAc/hexanes (6:4) afforded the title intermediate as a white foamy solid.

Physical data were as follows:

$C_{19}H_{28}N_4O_4$ (MW 376.45), mass spectroscopy MH+, 377.4, MH−, 375.3.

Anal. Calcd. for $C_{19}H_{28}N_4O_4$: Theory, C, 60.62; H, 7.50; N, 14.88. Found, C, 60.68; H, 7.42; N, 14.38.

Step B—Synthesis of 3-(L-Alaninyl)-amino-1,5-bis-methyl-1,3,4,5-tetrahydro-(2H)-1,5-benzodiazepine-2-one Following the General Procedure E using the product from Step A, the title compound was prepared. HPLC purification eluting with EtOAc/hexanes (6:4) afforded the title compound as a thick yellow oil.

Physical data were as follows:

$C_{14}H_{20}N_4O_2$: (MW 276.34), mass spectroscopy, MH+, 277.2.

The following examples illustrate how a compound prepared from a synthetic intermediate of this invention could be assayed to determine its ability to inhibit β-amyloid production in a cell or tested to determine its ability to suppress β-amyloid release and/or synthesis in vivo.

Example 57

Cellular Screen for the Detection of Inhibitors of β-Amyloid Production

Using the procedure of this example, compounds can be assayed for their ability to inhibit β-amyloid production in a cell line possessing the Swedish mutation. This screening assay employs cells (K293=human kidney cell line) which are stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569[15] and Citron et al.[16]. This mutation is commonly called the Swedish mutation and the cells, designated as "293 751 SWE", are plated in Corning 96-well plates at 2–4×10⁴ cells per well in Dulbecco's minimal essential media (Sigma, St. Louis, Mo.) plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media are removed and replaced with 200 μL of a compound to be tested (drug) containing media per well for a two hour pretreatment period and cells are incubated as above. Drug stocks are prepared in 100% dimethyl sulfoxide such that at the final drug concentration used in the treatment, the concentration of dimethyl sulfoxide does not exceed 0.5% and, in fact, usually equals 0.1%.

At the end of the pretreatment period, the media are again removed and replaced with fresh drug containing media as above and cells are incubated for an additional two hours. After treatment, plates are centrifuged in a Beckman GPR at 1200 rpm for five minutes at room temperature to pellet cellular debris from the conditioned media. From each well, 100 μL of conditioned media or appropriate dilutions thereof are transferred into an ELISA plate precoated with antibody 266 [P. Seubert, Nature (1992) 359:325–327[17]] against amino acids 13–28 of β-amyloid peptide as described in International Patent Application Publication No. 94/10569[15] and stored at 4° C. overnight. An ELISA assay employing labeled antibody 3D6 [P. Seubert, Nature (1992) 359:325–327[17]] against amino acids 1–5 of β-amyloid peptide is run the next day to measure the amount of β-amyloid peptide produced.

Cytotoxic effects of the compounds are measured by a modification of the method of Hansen, et al.[18]. To the cells remaining in the tissue culture plate is added 25 μL of a 3-(4,5-dimethylthiazol-2-yl)-2,5-diphenyltetrazolium bromide (MTT) (Sigma, St. Louis, Mo.) stock solution (5 mg/mL) to a final concentration of 1 mg/mL. Cells are incubated at 37° C. for one hour, and cellular activity is stopped by the addition of an equal volume of MTT lysis buffer (20% w/v sodium dodecylsulfate in 50% dimethylformamide, pH 4.7). Complete extraction is achieved by overnight shaking at room temperature. The difference in the $OD_{562\ nm}$ and the $OD_{650\ nm}$ is measured in a Molecular Device's $UV_{max}$ microplate reader as an indicator of the cellular viability.

The results of the β-amyloid peptide ELISA are fit to a standard curve and expressed as ng/mL β-amyloid peptide. In order to normalize for cytotoxicity, these results are divided by the MTT results and expressed as a percentage of the results from a drug free control. All results are the mean and standard deviation of at least six replicate assays.

The test compounds are assayed for β-amyloid peptide production inhibition activity in cells using this assay. The results of this assay can be used to demonstrate that the compounds prepared from the intermediates of this invention inhibit β-amyloid peptide production by at least 30% as compared to control when employed at 10 μg/mL.

Example 58

In Vivo Suppression of β-Amyloid Release and/or Synthesis

This example illustrates how the compounds prepared from the intermediate compounds of this invention could be tested for in vivo suppression of β-amyloid release and/or synthesis. For these experiments, 3 to 4 month old PDAPP mice are used [Games et al., (1995) Nature 373:523–527[19]]. Depending upon which compound is being tested, the compound is usually formulated at between 1 and 10 mg/mL.

Because of the low solubility factors of the compounds, they may be formulated with various vehicles, such as corn oil (Safeway, South San Francisco, Calif.); 10% ethanol in corn oil; 2-hydroxypropyl-β-cyclodextrin (Research Biochemicals International, Natick Mass.); and carboxy-methylcellulose (Sigma Chemical Co., St. Louis Mo.).

The mice are dosed subcutaneously with a 26 gauge needle and 3 hours later the animals are euthanized via $CO_2$ narcosis and blood is taken by cardiac puncture using a 1 cc 25 G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/mL aprotinin, 5 mM EDTA, pH 8.0, 10 μg/mL leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1–40) and β-amyloid (aa 1–42) consists of two monoclonal antibodies (mAb) to β-amyloid. The capture antibody, 266 [P. Seubert, *Nature* (1992) 359:325–327[17]], is specific to amino acids 13–28 of β-amyloid. The antibody 3D6 [Johnson-Wood et al., *PNAS USA* (1997) 94:1550–1555[20]], which is specific to amino acids 1–5 of β-amyloid, is biotinylated and served as the reporter antibody in the assay. The 3D6 biotinylation procedure employs the manufacturer's (Pierce, Bockford Ill.) protocol for NHS-biotin labeling of immundglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/mL (11 pM) and shows no cross-reactivity to the endogenous murine β-amyloid peptide at concentrations up to 1 ng/mL.

The configuration of the sandwich ELISA quantitating the level of β-amyloid (aa 1–42) employs the mAb 21F12 [Johnson-Wood et al., *PNAS USA* (1997) 94:1550–1555[20]] (which recognizes amino acids 33–42 of β-amyloid) as the capture antibody. Biotinylated 3D6 is also the reporter antibody in this assay which has a lower limit of sensitivity of ~125 pg/mL (28 pM).

The 266 and 21F12 capture mAbs are coated at 10 μg/mL into 96 well immunuoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/mL in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park Calif.) measuring the difference in absorbance at 450 mn and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 mL Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

Formulations other than those described above can also be used for oral delivery and intravenous delivery to a mammal. For oral delivery, the compound can be mixed with either 100% corn oil or, alternatively, in a solution containing 80% corn oil, 19.5% oleic acid and 0.5% labrafil. The compound can be mixed with the above solutions in concentrations ranging from 1 mg/mL to 10 mg/mL. The compound in solution is preferably administered orally to the mammal at a dose volume of 5 mL/kg of body weight. For IV delivery, the compound is preferably mixed with a solution of 3% ethanol, 3% solutol HS-15 and 94% saline. The compound is preferably mixed with the above solution in concentrations ranging from 0.25 mg/mL to 5 mg/mL. The compound in solution is preferably administered by IV to the mammal at a dose volume of 2 mL/kg of body weight.

From the foregoing description, various modifications and changes in the composition and method will occur to those skilled in the art. All such modifications coming within the scope of the appended claims are intended to be included therein.

What is claimed is:

1. A compound of formula I:

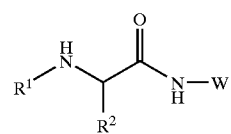

wherein

W is a substituted ε-caprolactam selected from the group consisting of:

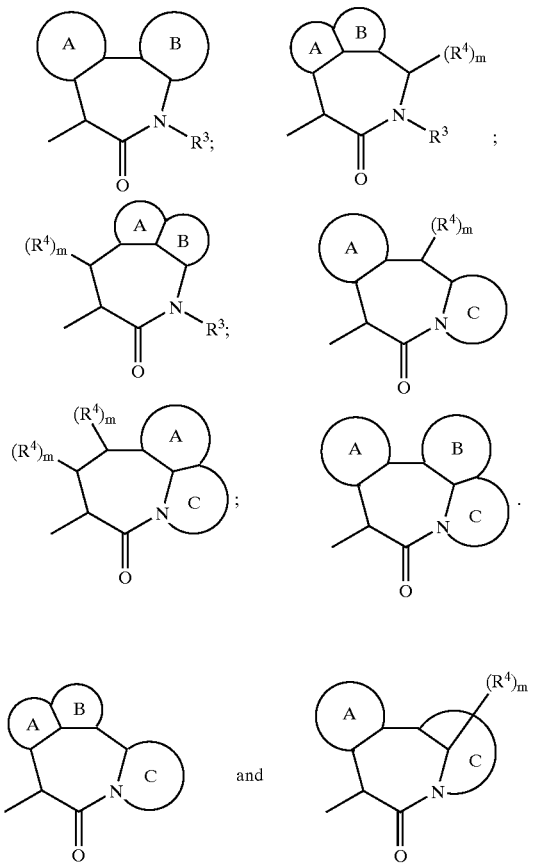

wherein
ring A, together with the atoms of the ε-caprolactam to which it is attached, forms a carbocyclic or heterocyclic ring selected from the group consisting of:
A) aryl having from 6 to 14 ring carbon atoms substituted with from 1 to 5 substituents selected from the group consisting of:
1) acyloxy selected from alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl is defined in R herein; wherein substituted alkyl is defined in S herein; wherein cycloalkyl is defined in B herein; wherein substituted cycloalkyl is defined in C herein; wherein aryl is defined in A herein; wherein heteroaryl is defined in F herein; and wherein heterocyclic is defined in G herein;
2) hydroxy;
3) acyl selected from alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— wherein alkyl is defined in R herein; wherein substituted alkyl is defined in S herein; wherein cycloalkyl is defined in B herein; wherein substituted cycloalkyl is defined in C herein; wherein aryl is defined in A herein; wherein heteroaryl is defined in F herein; and wherein heterocyclic is defined in G herein;
4) alkyl as defined in R herein;
5) alkoxy having the formula alkyl-O— wherein alkyl is defined in R herein;
6) alkenyl as defined in T herein;
7) alkynyl as defined in V herein;
8) substituted alkyl as defined in S herein;
9) substituted alkoxy of the formula substituted alkyl-O— where substituted alkyl is as defined in S herein;
10) substituted alkenyl as defined in U herein;
11) substituted alkynyl as defined in W herein;
12) amino having the formula —NH$_2$—;
13) substituted amino having the formula —N(R)$_2$ where each R is independently selected from the group consisting of hydrogen, alkyl, substituted alkyl alkenyl, substituted alkenyl, alkynyl, substituted alkynyl, aryl, cycloalkyl, substituted cycloalkyl, heteroaryl, heterocyclic and where both R groups are joined to form a heterocyclic group; wherein alkyl is defined in R herein; substituted alkyl is defined in S herein; wherein alkenyl is defined in T herein; wherein substituted alkenyl is defined in U herein; wherein alkynyl is defined in V herein; wherein substituted alkynyl is defined in W herein; wherein aryl is defined in A herein; wherein cycloalkyl is defined in B herein; wherein substituted cycloalkyl is defined in C herein; wherein heteroaryl is defined in F herein; and wherein heterocyclic is defined in G herein;
14) aminoacyl having the formula —NRC(O)R wherein each R is independently hydrogen, alkyl, substituted alkyl aryl, heteroaryl or heterocyclic; wherein alkyl is defined in R herein; wherein substituted alkyl is defined in S herein; wherein aryl is defined in A herein; wherein heteroaryl is defined in F herein; and wherein heterocyclic is defined in G herein;
15) acylamino having the formula —C(O)NRR where each R is independently hydrogen, alkyl, substituted alkyl, aryl, heteroaryl, or heterocyclic or where both R groups are joined to form a heterocyclic group; wherein alkyl is defined in R herein; wherein substituted alkyl is defined in S herein; wherein aryl is defined in A herein; wherein heteroaryl is defined in F herein; and wherein heterocyclic is defined in G herein;
16) alkaryl of the formula -alkylene-aryl having 1 to 8 carbon atoms in the alkylene moiety wherein aryl is defined in A herein and alkylene is a divalent alkyl where alkyl is defined in R herein;
17) aryl as defined in A herein;
18) aryloxy having the formula -aryl-O wherein aryl is defined in A herein;
19) azido;
20) carboxyl;
21) carboxylalkyl having the formula —C(O)Oalkyl and —C(O)O— substituted alkyl wherein alkyl as defined in R herein and substituted alkyl is defined in S herein;
22) cyano;
23) halo selected from fluoro, chloro, bromo and iodo;
24) nitro;
25) heteroaryl as defined in F herein;
26) heterocyclic as defined in G herein;
27) aminoacyloxy having the formula —NRC(O)OR wherein each R is independently hydrogen, alkyl, substituted alkyl, aryl, heteroaryl or heterocyclic; wherein alkyl is defined in R herein; wherein substituted alkyl is defined in S herein; wherein aryl is defined in A herein; wherein heteroaryl is defined in F herein; and wherein heterocyclic is defined in G herein;

28) oxyacylamino having the formula —OC(O)NRR where each R is independently hydrogen, alkyl, substituted alkyl, aryl, heteroaryl, or heterocyclic wherein alkyl is defined in R herein; wherein substituted alkyl is defined in S herein; wherein aryl is defined in A herein; wherein heteroaryl is defined in F herein; and wherein heterocyclic is defined in G herein;
29) thioalkoxy having the formula —S-alkyl, wherein alkyl as defined in R herein;
30) substituted thioalkoxy having the formula —S-substituted alkyl, wherein substituted alkyl is defined in S herein;
31) thioaryloxy having the formula aryl-S— wherein aryl is defined in A herein;
32) thioheteroaryloxy having the formula heteroaryl-S— wherein heteroaryl is defined F herein;
33) —SO-alkyl wherein alkyl is defined in R herein;
34) —SO-substituted alkyl wherein substituted alkyl is defined in S herein;
35) —SO-aryl wherein aryl is defined in A herein;
36) —SO-heteroaryl wherein heteroaryl is defined in F herein;
37) —$SO_2$-alkyl wherein alkyl is defined in R herein;
38) —$SO_2$-substituted alkyl wherein substituted alkyl is defined in S herein;
39) —$SO_2$-aryl wherein aryl is defined in A herein;:
40) —$SO_2$-heteroaryl wherein heteroaryl is defined in F herein; and
41) trihalomethyl wherein halo is defined in A23 herein;

B) cycloalkyl of from 3 to 12 carbon atoms;
C) substituted cycloalkyl having 3 to 12 carbon atoms and from 1 to 5 substituents selected from the group consisting of:
1) alkoxy as defined in A5 herein;
2) substituted alkoxy as defined in A9 herein;
3) cycloalkyl as defined in B herein;
4) substituted cycloalkyl as defined in C herein;:
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto having the formula =O;
21) thioketo having the formula =S;
22) thiol having the formula —SH;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy having the formula —O-heteroaryl wherein heteroaryl is defined in F herein;
29) heterocyclic as defined in G herein;
30) heterocyclooxy having the formula —O-heterocyclic wherein heterocyclic is defined in G herein;
31) hydroxyamino;
32) alkoxyamino wherein alkoxy is defined in A5 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —$SO_2$-alkyl as defined in A37 herein;
39) —$SO_2$-substituted alkyl as defined in A38 herein;
40) —$SO_2$-aryl as defined in A39 herein; and
41) —$SO_2$-heteroaryl as defined in A40 herein;

D) cycloalkenyl of from 4 to 8 carbon atoms;
E) substituted cycloalkenyl having from 4 to 8 carbon atoms and from 1 to 5 substituents selected from the group consisting of:
1) alkoxy as defined in A5 herein;
2) substituted alkoxy as defined in A9 herein;
3) cycloalkyl as defined in B herein;
4) substituted cycloalkyl as defined in C herein;
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto as defined in C20 herein;
21) thioketo as defined in C21 herein;
22) thiol as defined in C22 herein;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy as defined in C28 herein;
29) heterocyclic as defined in G herein;
30) heterocyclooxy as defined in C30 herein;
31) hydroxyamino;
32) alkoxyamino as defined in C32 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —$SO_2$-alkyl as defined in A37 herein;
39) —$SO_2$-substituted alkyl as defined in A38 herein;
40) —$SO_2$-aryl as defined in A39 herein; and
41) —$SO_2$-heteroaryl as defined in A40 herein;

F) heteroaryl of from 1 to 15 ring carbon atoms and 1 to 4 ring heteroatoms selected from oxygen, nitrogen and sulfur, substituted with from 1 to 5 substituents selected from:
1) acyloxy as defined in A1 herein;
2) hydroxy;
3) acyl as defined in A3 herein;
4) alkyl as defined in R herein;
5) alkoxy as defined in A5 herein;
6) alkenyl as defined in T herein;

7) alkynyl as defined in V herein;
8) substituted alkyl as defined in S herein;
9) substituted alkoxy as defined in A9 herein;
10) substituted alkenyl as defined in U herein;
11) substituted alkynyl as defined in W herein;
12) amino as defined in A12 herein;
13) substituted amino as defined in A13 herein;
14) aminoacyl as defined in A14 herein;
15) acylamino as defined in A15 herein;
16) alkaryl as defined in A16 herein;
17) aryl as defined in A herein;
18) aryloxy as defined in A18 herein;
19) azido;
20) carboxyl;
21) carboxylalkyl as defined in A21 herein;
22) cyano;
23) halo as defined in A23 herein;
24) nitro;
25) heteroaryl as defined in F herein;
26) heterocyclic as defined in G herein;
27) aminoacyloxy as defined in A27 herein;
28) oxyacylamino as defined in A28 herein;
29) thioalkoxy as defined in A29 herein;
30) substituted thioalkoxy as defined in A30 herein;
31) thioaryloxy as defined in A31 herein;
32) thioheteroaryloxy as defined in A32 herein;
33) —SO-alkyl as defined in A33 herein;
34) —SO-substituted alkyl as defined in A34 herein;
35) —SO-aryl as defined in A35 herein;
36) —SO-heteroaryl as defined in A36 herein;
37) —SO$_2$-alkyl as defined in A37 herein;
38) —SO$_2$-substituted alkyl as defined in A38 herein;
39) —SO$_2$-aryl as defined in A39 herein;
40) —SO$_2$-heteroaryl as defined in A40 herein; and
41) trihalomethyl as defined in A41 herein;

G) heterocyclic of from 1 to 15 ring carbon atoms and from 1 to 4 ring atoms selected from nitrogen, sulfur and oxygen, substituted with from 1 to 5 substituents selected from:
1) alkoxy as defined in A5 herein;
2) substituted alkoxy as defined in A9 herein;
3) cycloalkyl as defined in B herein;
4) substituted cycloalkyl as defined in C herein;
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto as defined in C20 herein;
21) thioketo as defined in C21 herein;
22) thiol as defined in C22 herein;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy as defined in C28 herein;
29) heterocyclic as defined in G herein;
30) heterocyclooxy as defined in C30 herein;
31) hydroxyamino;
32) alkoxyamino as defined in C32 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —SO$_2$-alkyl as defined in A37 herein;
39) —SO$_2$-substituted alkyl as defined in A38 herein;
40) —SO$_2$-aryl as defined in A39 herein; and
41) —SO$_2$-heteroaryl as defined in A40 herein;

ring B, together with the atoms of the ε-caprolactam to which it is attached, forms a carbocyclic or heterocyclic ring selected from the group consisting of:
H) aryl as defined in A herein;
I) cycloalkyl as defined in B herein;
J) substituted cycloalkyl as defined in C herein;
K) cycloalkenyl as defined in D herein;
L) substituted cycloalkenyl as defined in E herein;
M) heteroaryl as defined in F herein; and
N) heterocyclic as defined in G herein;

ring C, together with the atoms of the ε-caprolactam to which it is attached, forms a heteroaryl as defined in F herein or heterocyclic ring as defined in G herein;

$R^1$ is selected from the group consisting of:
O) hydrogen; and
P) an amino-blocking group being any group, bound to an amino group, which prevents undesired reactions from occurring at the amino group and which may be removed by conventional chemical and/or enzymatic procedures to reestablish the amino group;

$R^2$ is selected from the group consisting of:
Q) hydrogen;
R) alkyl of from 1 to 20 carbon atoms;
S) substituted alkyl of from 1 to 20 carbon atoms, having from 1 to 5 substituents selected from:
1) alkoxy as defined in A5 herein;
2) substituted alkoxy as defined in A9 herein;
3) cycloalkyl as defined in B herein;
4) substituted cycloalkyl as defined in C herein;
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto as defined in C20 herein;
21) thioketo as defined in C21 herein;
22) thiol as defined in C22 herein;
23) thioalkoxy as defined in A29 herein;
24) substituted thioalkoxy as defined in A30 herein;
25) aryl as defined in A herein;
26) aryloxy as defined in A18 herein;

27) heteroaryl as defined in F herein;
28) heteroaryloxy as defined in C28 herein;
29) heterocyclic as defined in G herein;
30) heterocyclooxy as defined in C30 herein;
31) hydroxyamino;
32) alkoxyamino as defined in C32 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —$SO_2$-alkyl as defined in A37 herein;
39) —$SO_2$-substituted alkyl as defined in A38 herein;
40) —$SO_2$-aryl as defined in A39 herein; and
41) —$SO_2$-heteroaryl as defined in A40 herein;

T) alkenyl of from 2 to 10 carbon atoms and 1–2 sites of alkenyl unsaturation;
U) substituted alkenyl having from 1 to 3 substituents selected from the group consisting of:
1) alkoxy as defined in A5 herein;
2) substituted alkoxy as defined in A9 herein;
3) cycloalkyl as defined in B herein;
4) substituted cycloalkyl as defined in C herein;
5) cycloalkoxy wherein alkoxy is defined in A5 herein
6) substituted cycloalkoxyl wherein substituted alkoxy is defined in A9 herein;
7) acyl as defined in A3 herein;
8) acylamino as defined in A 15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) cyano;
15) halogen wherein halo is defined in A23 herein;
16) hydroxyl;
17) carboxyl;
18) carboxylalkyl as defined in A21 herein;
19) keto as defined in C20 herein;
20) thioketo as defined in C21 herein;
21) thiol as defined in C22 herein;
22) thioalkoxy as defined in A29 herein;
23) substituted thioalkoxy as defined in A30 herein;
24) aryl as defined in A herein;
25) heteroaryl as defined in F herein;
26) heterocyclic as defined in G herein;
27) heterocyclooxy as defined in C30 herein;
28) nitro;
29) —SO-alkyl as defined in A33 herein;
30) —SO-substituted alkyl as defined in A34 herein;
31) —SO-aryl as defined in A35 herein;
32) —SO-heteroaryl as defined in A36 herein;
33) —$SO_2$-alkyl as defined in A37 herein;
34) —$SO_2$-substituted alkyl as defined in A38 herein;
35) —$SO_2$-aryl as defined in A39 herein; and
36) —$SO_2$-heteroaryl as defined in A40 herein;

V) alkynyl of from 2 to 10 carbon atoms and from 1–2 sites of alkynyl unsaturation;
W) substituted alkynyl of from 1 to 3 substituents selected from:
1) alkoxy as defined in A5 herein;
2) substituted alkoxy as defined in A9 herein;
3) cycloalkyl as defined in B herein;
4) substituted cycloalkyl as defined in C herein;
5) cycloalkoxy as defined in U5 herein;
6) substituted cycloalkoxyl as defined in U6 herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) cyano;
15) halogen wherein halo is defined in A23 herein;
16) hydroxyl;
17) carboxyl;
18) carboxylalkyl as defined in A21 herein;
19) keto as defined in C20 herein;
20) thioketo as defined as C21 herein;
21) thiol as defined as C22 herein;
22) thioalkoxy as defined in A29 herein;
23) substituted thioalkoxy as defined in A30 herein;
24) aryl as defined in A herein;
25) heteroaryl as defined in F herein;
26) heterocyclic as defined in G herein;
27) heterocyclooxy as defined in C30 herein;
28) nitro;
29) —SO-alkyl as defined in A33 herein;
30) —SO-substituted alkyl as defined in A34 herein;
31) —SO-aryl as defined in A35 herein;
32) —SO-heteroaryl as defined in A36 herein;
33) —$SO_2$-alkyl as defined in A37 herein;
34) —$SO_2$-substituted alkyl as defined in A38 herein;
35) —$SO_2$-aryl as defined in A39 herein; and
36) —$SO_2$-heteroaryl as defined in A40 herein;

X) aryl as defined in A herein;
Y) cycloalkyl as defined in B herein;
Z) heteroaryl as defined in F herein; and
AA) heterocyclic as defined in G herein;

$R^3$ is selected from the group consisting of:
BB) hydrogen;
CC) alkyl as defined in R herein;
DD) substituted alkyl as defined in S herein;
EE) alkenyl as defined in T herein;
FF) substituted alkenyl as defined in U herein;
GG) alkynyl as defined in as defined in V herein;
HH) substituted alkynyl as defined in W herein;
II) acyl as defined in A3 herein;
JJ) aryl as defined in A herein;
KK) cycloalkyl as defined in B herein;
LL) substituted cycloalkyl as defined in C herein;
MM) cycloalkenyl as defined in D herein;
NN) substituted cycloalkenyl as defined in E herein;
OO) heteroaryl as defined in F herein; and
PP) heterocyclic as defined in G herein;

each $R^4$ is independently selected from the group consisting of:
QQ) alkyl as defined in R herein;
RR) substituted alkyl as defined in S herein;
SS) alkenyl as defined in T herein;
TT) substituted alkenyl as defined in U herein;
UU) alkynyl as defined in V herein;
VV) substituted alkynyl as defined in W herein;
WW) aryl as defined in A herein;
XX) cycloalkyl as defined in B herein;
YY) substituted cycloalkyl as defined in C herein;
ZZ) cycloalkenyl as defined in D herein;

AAA) substituted cycloalkenyl as defined in E herein;
BBB) heteroaryl as defined in F herein; and
CCC) heterocyclic as defined in G herein;
m is an integer from 0 to 2; or salts thereof.

2. A compound of formula II:

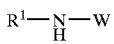

II wherein
W is a substituted ε-caprolactam selected from the group consisting of:

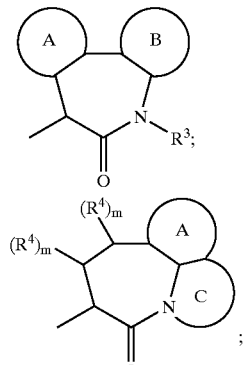

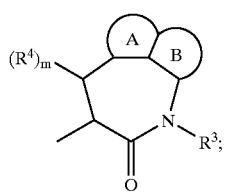

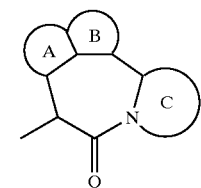

and wherein
ring A, together with the atoms of the ε-caprolactam to which it is attached, forms a carbocyclic or heterocyclic ring selected from the group consisting of:
A) aryl having from 6 to 14 ring carbon atoms substituted with from 1 to 5 substituents selected from the group consisting of:
1) acyloxy selected from alkyl-C(O)O—, substituted alkyl —C(O)O—, cycloalkyl-C(O)O—, substituted cycloalkyl-C(O)O—, aryl-C(O)O—, heteroaryl-C(O)O—, and heterocyclic-C(O)O— wherein alkyl is defined in R herein; wherein substituted alkyl is defined in S herein; wherein cycloalkyl is defined in B herein; wherein substituted cycloalkyl is defined in C herein; wherein aryl is defined in A herein; wherein heteroaryl is defined in F herein; and wherein heterocyclic is defined in G herein;
2) hydroxy;
3) acyl selected from alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— wherein alkyl is defined in R herein; wherein substituted alkyl is defined in S herein; wherein cycloalkyl is defined in B herein; wherein substituted cycloalkyl is defined in C herein; wherein aryl is defined in A herein; wherein heteroaryl is defined in F herein; and wherein heterocyclic is defined in G herein;
4) alkyl as defined in R herein;
5) alkoxy having the formula alkyl-O— wherein alkyl is defined in R herein;
6) alkenyl as defined in T herein;
7) alkynyl as defined in V herein;
8) substituted alkyl as defined in S herein;
9) substituted alkoxy of the formula substituted alkyl-O— where substituted alkyl is as defined in S herein;
10) substituted alkenyl as defined in U herein;
11) substituted alkynyl as defined in W herein;
12) amino having the formula —NH$_2$—;
13) substituted amino having the formula —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, heteroaryl, heterocyclic and where both R groups are joined to form a heterocyclic group; wherein alkyl is defined in R herein; substituted alkyl is defined in S herein; wherein alkenyl is defined in T herein; wherein substituted alkenyl is defined in U herein; wherein alkynyl is defined in V herein; wherein substituted alkynyl is defined in W herein; wherein aryl is defined in A herein; wherein cycloalkyl is defined in B herein; wherein substituted cycloalkyl is defined in C herein; wherein heteroaryl is defined in F herein; and wherein heterocyclic is defined in G herein;
14) aminoacyl having the formula —NRC(O)R wherein each R is independently hydrogen, alkyl, substituted alkyl, aryl, heteroaryl or heterocyclic; wherein alkyl is defined in R herein; wherein substituted alkyl is defined in S herein; wherein aryl is defined in A herein; wherein heteroaryl is defined in F herein; and wherein heterocyclic is defined in G herein;
15) acylamino having the formula —C(O)NRR where each R is independently hydrogen, alkyl, substituted alkyl, aryl, heteroaryl, or heterocyclic or where both R groups are joined to form a heterocyclic group; wherein alkyl is defined in R herein; wherein substituted alkyl is defined in S herein; wherein aryl is defined in A herein; wherein heteroaryl is defined in F herein; and wherein heterocyclic is defined in G herein;
16) alkaryl of the formula -alkylene-aryl having 1 to 8 carbon atoms in the alkylene moiety wherein aryl is defined in A herein and alkylene is a divalent alkyl where alkyl is defined in R herein;
17) aryl as defined in A herein;
18) aryloxy having the formula -aryl-O wherein aryl is defined in A herein;
19) azido;
20) carboxyl;
21) carboxylalkyl having the formula —C(O)Oalkyl and —C(O)O— substituted alkyl wherein alkyl as defined in R herein and substituted alkyl is defined in S herein;
22) cyano;
23) halo selected from fluoro, chloro, bromo and iodo;

24) nitro;
25) heteroaryl as defined in F herein;
26) heterocyclic as defined in G herein;
27) aminoacyloxy having the formula —NRC(O)OR wherein each R is independently hydrogen, alkyl, substituted alkyl, aryl, heteroaryl or heterocyclic; wherein alkyl is defined in R herein; wherein substituted alkyl is defined in S herein; wherein aryl is defined in A herein; wherein heteroaryl is defined in F herein; and wherein heterocyclic is defined in G herein;
28) oxyacylamino having the formula —OC(O)NRR where each R is independently hydrogen, alkyl, substituted alkyl, aryl, heteroaryl, or heterocyclic wherein alkyl is defined in R herein; wherein substituted alkyl is defined in S herein; wherein aryl is defined in A herein; wherein heteroaryl is defined in F herein; and wherein heterocyclic is defined in G herein;
29) thioalkoxy having the formula —S-alkyl, wherein alkyl as defined in R herein; 30) substituted thioalkoxy having the formula —S-substituted alkyl, wherein substituted alkyl is defined in S herein;
31) thioaryloxy having the formula aryl-S— wherein aryl is defined in A herein;
32) thioheteroaryloxy having the formula heteroaryl-S— wherein heteroaryl is defined F herein;
33) —SO-alkyl wherein alkyl is defined in R herein;
34) —SO-substituted alkyl wherein substituted alkyl: is defined in S herein;
35) —SO-aryl wherein aryl is defined in A herein;
36) —SO-heteroaryl wherein heteroaryl is defined in F herein;
37) —$SO_2$-alkyl wherein alkyl is defined in R herein;
38) —$SO_2$-substituted alkyl wherein substituted alkyl is defined in S herein;
39) —$SO_2$-aryl wherein aryl is defined in A herein;
40) —$SO_2$-heteroaryl wherein heteroaryl is defined in F herein; and
41) trihalomethyl wherein halo is defined in A23 herein;

B) cycloalkyl of from 3 to 12 carbon atoms;
C) substituted cycloalkyl having 3 to 12 carbon atoms and from 1 to 5 substituents selected from the group consisting of:
1) alkoxy as defined in A5 herein;
2) substituted alkoxy as defined in A9 herein;
3) cycloalkyl as defined in B herein;
4) substituted cycloalkyl as defined in C herein;.
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto having the formula =O;
21) thioketo having the formula =S;
22) thiol having the formula —SH;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy having the formula —O-heteroaryl wherein heteroaryl is defined in F herein;
29) heterocyclic as defined in G herein;
30) heterocyclooxy having the formula —O-heterocyclic wherein heterocyclic is defined in G herein;
31) hydroxyamino;
32) alkoxyamino wherein alkoxy is defined in A5 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —$SO_2$-alkyl as defined in A37 herein;
39) —$SO_2$-substituted alkyl as defined in A38 herein;
40) —$SO_2$-aryl as defined in A39 herein; and
41) —$SO_2$-heteroaryl as defined in A40 herein;

D) cycloalkenyl of from 4 to 8 carbon atoms;
E) substituted cycloalkenyl having from 4 to 8 carbon atoms and from 1 to 5 substituents selected from the group consisting of:
1) alkoxy as defined in A5 herein;
2) substituted alkoxy as defined in A9 herein;
3) cycloalkyl as defined in B herein;
4) substituted cycloalkyl as defined in C herein;
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto as defined in C20 herein;
21) thioketo as defined in C21 herein;
22) thiol as defined in C22 herein;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy as defined in C28 herein;
29) heterocyclic as defined in G herein;
30) heterocyclooxy as defined in C30 herein;
31) hydroxyamino;
32) alkoxyamino as defined in C32 herein;
33) nitro;
34) —SO-alkyl as defined in A33 herein;
35) —SO-substituted alkyl as defined in A34 herein,
36) —SO-aryl as defined in A35 herein;
37) —SO-heteroaryl as defined in A36 herein;

38) —SO$_2$-alkyl as defined in A37 herein;
39) —SO$_2$-substituted alkyl as defined in A38 herein;
40) —SO$_2$-aryl as defined in A39 herein; and
41) —SO$_2$-heteroaryl as defined in A40 herein;

F) heteroaryl of from 1 to 15 ring carbon atoms and 1 to 4 ring heteroatoms selected from oxygen, nitrogen and sulfur, substituted with from 1 to 5 substituents selected from:
1) acyloxy as defined in A1 herein;
2) hydroxy;
3) acyl as defined in A3 herein;
4) alkyl as defined in R herein;
5) alkoxy as defined in A5 herein;
6) alkenyl as defined in T herein;
7) alkynyl as defined in V herein;
8) substituted alkyl as defined in S herein;
9) substituted alkoxy as defined in A9 herein;
10) substituted alkenyl as defined in U herein;
11) substituted alkynyl as defined in W herein;
12) amino as defined in A12 herein;
13) substituted amino as defined in A13 herein;
14) aminoacyl as defined in A14 herein;
15) acylamino as defined in A15 herein;
16) alkaryl as defined in A16 herein;
17) aryl as defined in A herein;
18) aryloxy as defined in A18 herein;
19) azido;
20) carboxyl;
21) carboxylalkyl as defined in A21 herein;
22) cyano;
23) halo as defined in A23 herein;
24) nitro;
25) heteroaryl as defined in F herein;
26) heterocyclic as defined in G herein;
27) aminoacyloxy as defined in A27 herein;
28) oxyacylamino as defined in A28 herein;
29) thioalkoxy as defined in A29 herein;
30) substituted thioalkoxy as defined in A30 herein ;
31) thioaryloxy as defined in A31 herein;
32) thioheteroaryloxy as defined in A32 herein;
33) —SO-alkyl as defined in A33 herein;
34) —SO-substituted alkyl as defined in A34 herein;
35) —SO-aryl as defined in A35 herein;
36) —SO-heteroaryl as defined in A36 herein;
37) —SO$_2$-alkyl as defined in A37 herein;
38) —SO$_2$-substituted alkyl as defined in A38 herein;
39) —SO$_2$-aryl as defined in A39 herein;
40) —SO$_2$-heteroaryl as defined in A40 herein; and
41) trihalomethyl as defined in A41 herein;

G) heterocyclic of from 1 to 15 ring carbon atoms and from 1 to 4 ring atoms selected from nitrogen, sulfur and oxygen, substituted with from 1 to 5 substituents selected from:
1) alkoxy as defined in A5 herein;
2) substituted alkoxy as defined in A9 herein;
3) cycloalkyl as defined in B herein;
4) substituted cycloalkyl as defined in C herein;
5) cycloalkenyl as defined in D herein;
6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto as defined in C20 herein;
21) thioketo as defined in C21 herein;
22) thiol as defined in C22 herein;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy as defined in C28 herein;
29) heterocyclic as defined in G herein;
30) heterocyclooxy as defined in C30 herein;
31) hydroxyamino;
32) alkoxyamino as defined in C32 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —SO$_2$-alkyl as defined in A37 herein;
39) —SO$_2$-substituted alkyl as defined in A38 herein;
40) —SO$_2$-aryl as defined in A39 herein; and
41) —SO$_2$-heteroaryl as defined in A40 herein;

ring B, together with the atoms of the ε-caprolactam to which it is attached, forms a carbocyclic or heterocyclic ring selected from the group consisting of:
H) aryl as defined in A herein;
I) cycloalkyl as defined in B herein;
J) substituted cycloalkyl as defined in C herein;
K) cycloalkenyl as defined in D herein;
L) substituted cycloalkenyl as defined in E herein;
M) heteroaryl as defined in F herein; and
N) heterocyclic as defined in G herein;

ring C, together with the atoms of the ε-caprolactam to which it is attached, forms a heteroaryl as defined in F herein or heterocyclic ring as defined in G herein;

$R^1$ is selected from the group consisting of:
O) hydrogen; and
P) an amino-blocking group being any group, bound to an amino group, which prevents undesired reactions from occurring at the amino group and which may be removed by conventional chemical and/or enzymatic procedures to reestablish the amino group;

$R^3$ is selected from the group consisting of:
Q) hydrogen;
[R) alkyl as defined in R herein;
S) substituted alkyl as defined in S herein;
T) alkenyl as defined in T herein;
U) substituted alkenyl as defined in U herein;
V) alkynyl as defined in as defined in V herein;
W) substituted alkynyl as defined in W herein;]
R) alkyl of from 1 to 20 carbon atoms;
S) substituted alkyl of from 1 to 20 carbon atoms having from 1 to 5 substituents selected from:
1) alkoxy as defined in A5 herein;
2) substituted alkoxy as defined in A9 herein;
3) cycloalkyl as defined in B herein;
4) substituted cycloalkyl as defined in C herein;
5) cycloalkenyl as defined in D herein;

6) substituted cycloalkenyl as defined in E herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) oxyacylamino as defined in A28 herein;
15) cyano;
16) halogen wherein halo is defined in A23 herein;
17) hydroxyl;
18) carboxyl;
19) carboxylalkyl as defined in A21 herein;
20) keto as defined in C20 herein;
21) thioketo as defined in C21 herein;
22) thiol as defined in C22 herein;
23) thioalkoxy as defined in A29 herein;
24) substituted thioalkoxy as defined in A30 herein;
25) aryl as defined in A herein;
26) aryloxy as defined in A18 herein;
27) heteroaryl as defined in F herein;
28) heteroaryloxy as defined in C28 herein;
29) heterocyclic as defined in G herein;
30) heterocyclooxy as defined in C30 herein;
31) hydroxyamino;
32) alkoxyamino as defined in C32 herein;
33) nitro;
34) —SO-alkyl as defined in A33 herein;
35) —SO-substituted alkyl as defined in A34 herein;
36) —SO-aryl as defined in A35 herein;
37) —SO-heteroaryl as defined in A36 herein;
38) —SO$_2$-alkyl as defined in A37 herein;
39) —SO$_2$-substituted alkyl as defined in A38 herein;
40) —SO$_2$-aryl as defined in A39 herein; and
41) —SO$_2$-heteroaryl as defined in A40 herein;

T) alkenyl of from 2 to 10 carbon atoms and 1–2 sites of alkenyl unsaturation;

U) substituted alkenyl having from 1 to 3 substituents selected from the group consisting of:
1) alkoxy as defined in A5 herein;
2) substituted alkoxy as defined in A9 herein;
3) cycloalkyl as defined in B herein;
4) substituted cycloalkyl as defined in C herein;
5) cycloalkoxy wherein alkoxy is defined in A5 herein;
6) substituted cycloalkoxyl wherein substituted alkoxy is defined in A9 herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) cyano;
15) halogen wherein halo is defined in A23 herein;
16) hydroxyl;
17) carboxyl;
18) carboxylalkyl as defined in A21 herein;
19) keto as defined in C20 herein;
20) thioketo as defined in C21 herein;
21) thiol as defined in C22 herein;
22) thioalkoxy as defined in A29 herein;
23) substituted thioalkoxy as defined in A30 herein;
24) aryl as defined in A herein;
25) heteroaryl as defined in F herein;
26) heterocyclic as defined in G herein;
27) heterocyclooxy as defined in C30 herein;
28) nitro;
29) —SO-alkyl as defined in A33 herein;
30) —SO-substituted alkyl as defined in A34 herein;
31) —SO-aryl as defined in A35 herein;
32) —SO-heteroaryl as defined in A36 herein;
33) —SO$_2$-alkyl as defined in A37 herein;
34) —SO$_2$-substituted alkyl as defined in A38 herein;
35) —SO$_2$-aryl as defined in A39 herein; and
36) —SO$_2$-heteroaryl as defined in A40 herein;

V) alkynyl of from 2 to 10 carbon atoms and from 1–2 sites of alkynyl unsaturation;

W) substituted alkynyl of from 1 to 3 substituents selected from:
1) alkoxy as defined in A5 herein;
2) substituted alkoxy as defined in A9 herein;
3) cycloalkyl as defined in B herein;
4) substituted cycloalkyl as defined in C herein;
5) cycloalkoxy as defined in U5 herein;
6) substituted cycloalkoxyl as defined in U6 herein;
7) acyl as defined in A3 herein;
8) acylamino as defined in A15 herein;
9) acyloxy as defined in A1 herein;
10) amino as defined in A12 herein;
11) substituted amino as defined in A13 herein;
12) aminoacyl as defined in A14 herein;
13) aminoacyloxy as defined in A27 herein;
14) cyano;
15) halogen wherein halo is defined in A23 herein;
16) hydroxyl;
17) carboxyl;
18) carboxylalkyl as defined in A21 herein;
19) keto as defined in C20 herein;
20) thioketo as defined as C21 herein;
21) thiol as defined as C22 herein;
22) thioalkoxy as defined in A29 herein;
23) substituted thioalkoxy as defined in A30 herein;
24) aryl as defined in A herein;
25) heteroaryl as defined in F herein;
26) heterocyclic as defined in G herein;
27) heterocyclooxy as defined in C30 herein;
28) nitro;
29) —SO-alkyl as defined in A33 herein;
30) —SO-substituted alkyl as defined in A34 herein;
31) —SO-aryl as defined in A35 herein;
32) —SO-heteroaryl as defined in A36 herein;
33) —SO$_2$-alkyl as defined in A37 herein;
34) —SO$_2$-substituted alkyl as defined in A38 herein;
35) —SO$_2$-aryl as defined in A39 herein; and
36) —SO$_2$-heteroaryl as defined in A40 herein;

X) acyl as defined in A3 herein;
Y) aryl as defined in A herein;
Z) cycloalkyl as defined in B herein;
AA) substituted cycloalkyl as defined in C herein;
BB) cycloalkenyl as defined in D herein;
CC) substituted cycloalkenyl as defined in E herein;
DD) heteroaryl as defined in F herein; and
EE) heterocyclic as defined in G herein;

each $R^4$ is independently selected from the group consisting of:
FF) alkyl as defined in R herein;
GG) substituted alkyl as defined in S herein;
HH) alkenyl as defined in T herein;
II) substituted alkenyl as defined in U herein;
JJ) alkynyl as defined in V herein;

KK) substituted alkynyl as defined in W herein;

each R⁴ is independently selected from the group consisting of:

FF) alkyl as defined in R herein;

GG) substituted alkyl as defined in S herein;

HH) alkenyl as defined in T herein;

II) substituted alkenyl as defined in U herein;

JJ) alkynyl as defined in V herein;

KK) substituted alkynyl as defined in W herein;

LL) aryl as defined in A herein;

MM) cycloalkyl as defined in B herein;

NN) substituted cycloalkyl as defined in C herein;

OO) cycloalkenyl as defined in D herein;

PP) substituted cycloalkenyl as defined in E herein;

QQ) heteroaryl as defined in F herein; and

RR) heterocyclic as defined in G herein;

m is an integer from 0 to 2; or salts thereof.

3. The compound of claims 1 or 2 wherein $R^1$ is selected from the group consisting of hydrogen, tert-butoxycarbonyl, benzyloxycarbonyl, acetyl, 1-(1'-adamantyl)-1-methylethoxycarbonyl, allyloxycarbonyl, benzyloxymethyl, 2-p-biphenyliso-propyloxycarbonyl, tert-butyldimethylsilyl, benzoyl, benzyl, 9-fluorenylmethyloxy-carbonyl, 4-methylbenzyl, 4-methoxybenzyl, 2-nitrophenylsulfenyl, 3-nitro-2-pyridine-sulfenyl, trifluoroacetyl, 2,4,6-trimethoxybenzyl and trityl.

4. The compound of claim 3 wherein $R^1$ is selected from the group consisting of hydrogen and tert-butoxycarbonyl.

5. The compound of claim 1 wherein $R^2$ is selected from the group consisting of hydrogen, alkyl, substituted alkyl, alkenyl, cycloalkyl, aryl, heteroaryl and heterocyclic.

6. The compound of claim 5 wherein $R^2$ is selected from the group consisting of hydrogen, methyl, ethyl, n-propyl, isopropyl, n-butyl, isobutyl, sec-butyl, tert-butyl, —CH₂CH(CH₂CH₃)₂, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH₂-cyclopropyl, —CH₂-cyclohexyl, —CH₂CH₂-cyclopropyl, —CH₂CH₂-cyclohexyl, —CH₂-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH₃)₂NCH₂CH₂CH₂O-benzyl, p-(CH₃)₃COC(O)CH₂O-benzyl, p-(HOOCCH₂O)-benzyl, 2-aminopyrid-6-yl, p-(N-morpholino-CH₂CH₂O)-benzyl, —CH₂CH₂C(O)NH₂, —CH₂-imidazol-4-yl, —CH₂-(3-tetrahydrofuranyl), —CH₂-thiophen-2-yl, —CH₂(1-methyl)cyclopropyl, —CH₂-thiophen-3-yl, thiophen-3-yl, thiophen-2-yl, —CH₂—C(O)O-t-butyl, —CH₂—C(CH₃)₃, —CH₂CH(CH₂CH₃)₂, -2-methylcyclopentyl, -cyclohex-2-enyl, —CH[CH(CH₃)₂]COOCH₃, —CH₂CH₂N(CH₃)₂, —CH₂C(CH₃)═CH₂, —CH₂CH═CHCH₃, —CH₂OH, —CH(OH)CH₃, —CH(O-t-butyl)CH₃, —CH(O—CH₂Ph)CH₃, —CH₂OCH₃, —(CH₂)₄NH-Boc, —(CH₂)₄NH₂, —CH₂-pyridyl, pyridyl, —CH₂-naphthyl, —CH₂-(4-morpholinyl), p-(4-morpholinyl-CH₂CH₂O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH₂CH₂SCH₃, thien-2-yl and thien-3-yl.

7. The compound of claims 1 or 2 wherein $R^3$ is selected from the group consisting of hydrogen, alkyl, substituted alkyl and cycloalkyl.

8. The compound of claim 7 wherein $R^3$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl and cyclohexyl.

9. The compound of claims 1 or 2 wherein W is a substituted ε-caprolactam selected from the group consisting of:

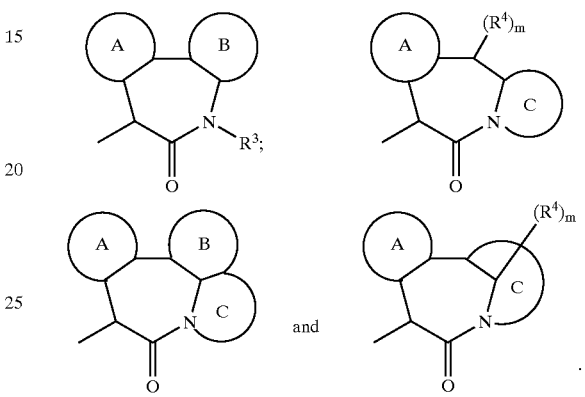

10. The compound of claim 9 wherein rings A and B are the same or different and each is independently selected from the group consisting of aryl, cycloalkyl, cycloalkenyl, heteroaryl and heterocyclic.

11. The compound of claim 10 wherein rings A and B are independently selected from the group consisting of aryl and cycloalkyl.

12. The compound of claim 11 wherein rings A and B are independently aryl.

13. The compound of claim 9 wherein W is a substituted ε-caprolactam of the formula:

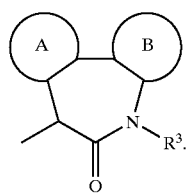

14. The compound of claim 13 wherein rings A and B are the same or different and each is independently selected from the group consisting of aryl, cycloalkyl, cycloalkenyl, heteroaryl and heterocyclic.

15. The compound of claim 14 wherein rings A and B are independently selected from the group consisting of aryl and cycloalkyl.

16. The compound of claim 15 wherein rings A and B are independently aryl.

17. The compounds of claim 15 wherein rings A and B are independently cycloalkyl.

18. The compound of claim 13 wherein W is a substituted ε-caprolactam of the formula:

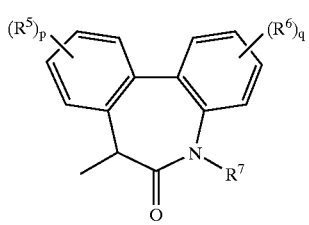

wherein
- each $R^5$ is independently selected from the group consisting of acyl, acylamino, acyloxy, alkenyl, substituted alkenyl, alkoxy, substituted alkoxy, alkl, substituted alkyl, alkynyl, substituted alkynyl, amino, substituted amino, aminoacyl, acyl, aryloxy, carboxyl, carboxyalkyl, cyano, cycloalkyl, substituted cycloalkyl, halo, heteroalryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;
- each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;
- $R^7$ is selected from the group consisting of hydrogen, alkyl, substituted alkyl, alkenyl, substituted alkenyl, alkynyl, substituted alkynyl, acyl, aryl, cycloalkyl, substituted cycloalkyl, cycloalkenyl, substituted cycloalkenyl, heteroaryl and heterocyclic;
- p is an integer from 0 to 4; q is an integer from 0 to 4; and salts thereof.

19. The compound of claim 18 wherein $R^5$ and $R^6$ are independently selected from the group consisting of alkoxy, substituted alkoxy, alkyl substituted alkyl, amino, substituted amino, carboxyl, carboxyalkyl, cyano, halo, nitro, thioalkoxy and substituted thioalkoxy.

20. The compound of claim 18 wherein $R^7$ is selected from the group consisting of hydrogen, alkyl, substituted alkyl, acyl, aryl, cycloalkyl and substituted cycloalkyl.

21. The compound of claim 20 wherein $R^7$ is selected from the group consisting of hydrogen, methyl, 2-methypropyl, hexyl, methoxycarbonylmethyl, 3,3-dimethyl-2-oxobutyl, 4-phenylbutyl, cyclopropylmethyl, 2,2,2-trifluoroethyl and cyclohexyl.

22. The compound of claim 18 wherein W is a substituted ε-caprolactam selected from the group consisting of 5,7-dihydro-6H-dibenz[b,d]azepin-6-one-5-yl, 7-methyl-5,7-dihydro-6H-dibenz[b,d]azepin-6-one-5-yl, 7-(2-methylpropyl)-5,7-dihydro-6H-dibenz[b,d]azepin-6-one-5-yl, 7-(methoxyacetyl)-5,7-dihydro-6H-dibenz[b,d]azepin-6-one-5-yl, 7-(3,3-dimethylbutan-2-onyl)-5,7-dihydro-6H-dibenz[b,d]azepin-6-one-5-yl, 7-phenbutyl-5,7-dihydro-6H-dibenz[b,d]azepin-6-one-5-yl, 7-cyclopropymethyl-5,7-dihydro-6H-dibenz[b,d]azepin-6-one-5-yl, 7-(2',2',2'-trifluoroethyl)-5,7-dihydro-6H-dibenz[b,d]azepin-6-one-5-yl, 7-cyclohexyl-5,7-dihydro-6H-dibenz[b,d]azepin-6-one-5-yl, 7-hexyl-5,7-dihydro-6H-dibenz[b,d]azepin-6-one-5-yl, 9-fluoro-7-methyl-5,7-dihydro-6H-dibenz[b,d]azepin-6-one-5-yl, 10-fluoro-7-methyl-5,7-dihydro-6H-dibenz[b,d]azepin-6-one-5-yl, 13-fluoro-7-methyl-5,7-dihydro-6H-dibenz[b,d]azepin-6-one-5-yl and 7-methyl-1,2,3,4,5,7-hexahydro-6H-dicyclohexyl[b,d]azepin-6-one-5-yl.

23. The compound of claim 9 wherein W is a substituted ε-caprolactam of the formula:

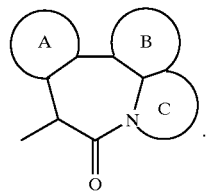

24. The compound of claim 23 wherein rings A and B are the same or different and each is independently selected from the group consisting of aryl, cycloalkyl, cycloalkenyl, heteroaryl and heterocyclic.

25. The compound of claim 24 wherein rings A and B are independently selected from the group consisting of aryl and cycloalkyl.

26. The compound of claim 25 wherein rings A and B are independently aryl.

27. The compound of claim 26 wherein W is a substituted ε-caprolactam of the formula:

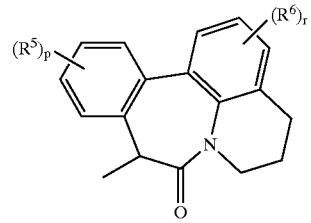

wherein
- each $R^5$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;
- each $R^6$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl;
- p is an integer from 0 to 4; r is an integer from 0 to 3; and salts thereof.

28. The compound of claim 27 wherein $R^5$ and $R^6$ are independently selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy.

29. The compound of claim 9 wherein W is a substituted ε-caprolactam of the formula:

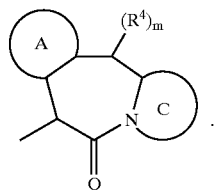

30. The compound of claim 29 wherein ring A is selected from the group consisting of aryl, cycloalkyl, cycloalkenyl, heteroaryl and heterocyclic.
31. The compound of claim 30 wherein ring A is selected from the group consisting of aryl and cycloalkyl.
32. The compound of claim 31 wherein ring A is aryl.
33. The compound of claim 32 wherein W is a substituted ε-caprolactam of the formula:

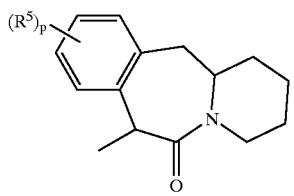

wherein
each $R^5$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted substituted alkyl, —SO-aryl, —SO-heteroaryl, —$SO_2$-alkyl, —$SO_2$-substituted alkyl, —$SO_2$-aryl, and —$SO_2$-heteroaryl;
p is an integer from 0 to 4; and salts thereof.
34. The compound of claim 33 wherein each $R^5$ is independently selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy.
35. The compound of claim 34 wherein each $R^5$ is independently selected from the group consisting of alkyl, substituted alkyl, alkoxy and halo.
36. The compound of claim 9 wherein W is a substituted ε-caprolactam of the formula:

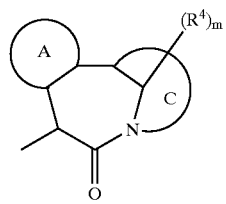

37. The compound of claim 36 wherein ring A is selected from the group consisting of aryl, cycloalkyl, cycloalkenyl, heteroaryl and heterocyclic.
38. The compound of claim 37 wherein ring A is selected from the group consisting of aryl and cycloalkyl.

39. The compound of claim 38 wherein ring A is aryl.
40. The compound of claim 39 wherein W is a substituted ε-caprolactam of the formula:

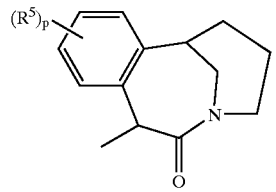

wherein each $R^5$ is independently selected from the group consisting of acyl, acylamino, acyloxy, alkenyl, substituted alkenyl, alkoxy, substituted alkoxy, alkyl, substituted alkyl, alkynyl, substituted alkynyl, amino, substituted amino, aminoacyl, aryl, aryloxy, carboxyl, carboxyalkyl, cyano, cycloalkyl, substituted cycloalkyl, halo, heteroaryl, heterocyclic, nitro, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl;

p is an integer from 0 to 4; and salts thereof.

41. The compound of claim 40 wherein $R^5$ is selected from the group consisting of alkoxy, substituted alkoxy, alkyl, substituted alkyl, amino, substituted amino, carboxyl, carboxyalkyl, cyano, halo, nitro, thioalkoxy and substituted thioalkoxy.

42. The compound of claims 1 or 2, wherein W is a substituted ε-caprolactam selected from the group consisting of:

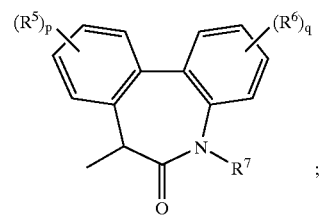

;

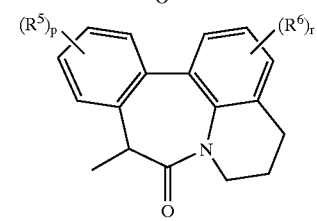

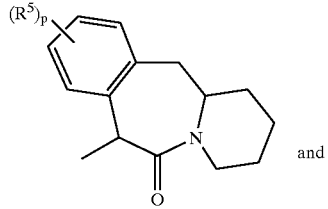

and

-continued

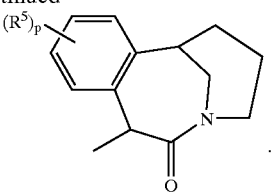

43. The compound of claim 42, wherein p, q and r are independently 0 or 1; each $R^5$ is independently selected from the group consisting of alkyl, substituted alkyl, cycloalkyl, alkoxy, and halo; each $R^6$ is independently selected from the group consisting of alkyl, substituted alkyl, cycloalkyl, alkoxy, and halo; and each $R^7$ is independently selected from the group consisting of alkyl, substituted alkyl, cycloalkyl and aryl.

44. The compound of claim 43, wherein p, q and r are 0.

45. The compound of claim 42, wherein p, q and r are independently 0, 1 or 2; each $R^5$ is independently selected from the group consisting of alkyl, substituted alkyl, alkoxy, and halo; each $R^6$ is independently selected from the group consisting of alkyl, substituted alkyl, alkoxy, and halo; and each $R^7$ is independently selected from the group consisting of alkyl, substituted alkyl, cycloalkyl and aryl.

46. The compound of claim 45, wherein p and q are independently 0 or 1.

47. A compound selected from the group consisting of:

5-amino-7-methyl-5,7-dihydro-6H-dibenz[b,d]azepin-6-one 5-(N-Boc-amino)-5,7-dihydro-6H-dibenz[b,d]azepin-6-one 5-(N-Boc-amino)-7-(2-methylpropyl)-5,7-dihydro-6H-dibenz[b,d]azepin-6-one 5-amino-7-(2-methylpropyl)-5,7-dihydro-6H-dibenz[b,d]azepin-6-one 5-(N-Boc-amino)-7-(methoxycarbonymethyl)-5,7-dihydro-6H-dibenz[b,d]azepin-6-one 5-amino-7-methoxcarbonylmethyl)-5,7-dihydro-6H-dibenz[b,d]azepin-6-one 5-(N-Boc-amino)-7-(3,3-dimethyl-butanonyl)-5,7-dihydro-6H-dibenz[b,d]azepin-6-one 5-amino-7-(3,3-dimethyl-2-butanonyl)-5,7-dihydro-6H-dibenz[b,d]azepin-6-one 5-amino-7-phenbutyl-5,7-dihydro-6H-dibenz[b,d]azepin-6-one 5-amino-7-cyclopropymethyl-5,7-dihydro-6H-dibenz[b,d]azepin-6-one 5-amino-7-(2',2',2'-trifluoroethyl)-5,7-dihydro-6H-dibenz[b,d]azepin-6-one 5-amino-7-cyclohexyl-5,7-dihydro-6H-dibenz[b,d]azepin-6-one 5-amino-7-hexyl-5,7-dihydro-6H-dibenz[b,d]azepin-6-one 5-amino-9-fluoro-7-methyl-5,7-dihydro-6H-dibenz[b,d]azepin-6-one 5-amino-10-fluoro-7-methyl-5,7-dihydro-6H-dibenz[b,d]azepin-6-one 5-amino-13-fluoro-7-methyl-5,7-dihydro-6H-dibenz[b,d]azepin-6-one 5-amino-7-methyl-1,2,3,4,5,7-hexahydro-6H-dicyclohexyl[b,d]azepin-6-one 5-(N-Boc-L-alaninyl)amino-7-methyl-5,7-dihydro-6H-dibenz[b,d]azepin-6-one 5-(L-alaninyl)amino-7-methyl-5,7-dihydro-6H-dibenz[b,d]azepin-6-one 5-(N-Boc-L-valinyl)amino-7-methyl -5,7-dihydro-6H-dibenz[b,d]azepin-6-one 5-(L-valinyl)amino-7-methyl-5,7-dihydro-6H-dibenz[b,d]azepin-6-one 5-(N-Boc-L-tert-leucinyl)amino-7-methyl-5,7-dihydro-6H-dibenz[b,d]azepin-6-one 5-(L-tert-leucinyl)amino-7-methyl-5,7-dihydro-6H-dibenz[b,d]azepin-6-one 5-(N-Boc-L-alaninyl)amino-9-fluoro-7-methyl-5,7-dihydro-6H-dibenz[b,d]azepin-6-one 5-(L-alaninyl)amino-9-fluoro-7-methyl-5,7-dihydro-6H-dibenz[b,d]azepin-6-one 5-(N-Boc-L-alaninyl)amino-10-fluoro-7-(methyl-5,7-dihydro-6H-dibenz[b,d]azepin-6-one 5-(L-alaninyl)amino-10-fluoro-7-methyl-5,7-dihydro-6H-dibenz[b,d]azepin-6-one 5-(N-Boc-L-alaninyl)amino-13-fluoro-7-methyl-5,7-dihydro-6H-dibenz[b,d]azepin-6-one 5-(L-alaninyl)amino-13-fluoro-7-methyl-5,7-dihydro-6H-dibenz[b,d]azepin-6-one 5-(N-Boc-L-alaninyl)amino-7-cyclopropylmethyl-5,7-dihydro-6H-dibenz[b,d]azepin-6-one 5-(L-alaninyl)amino-7-cyclopropylmethyl-5,7-dihydro-6H-dibenz[b,d]azepin-6-one 5-(N-Boc-L-alaninyl)amino-7-phenbutyl-5,7-dihydro-6H-dibenz[b,d]azepin-6-one 5-(L-alaninyl)amino-7-phenbutyl-5,7-dihydro-6H-dibenz[b,d]azepin-6-one 5-(N-Boc-L-valinyl)amino-7-cyclopropylmethyl-5,7-dihydro-6H-dibenz[b,d]azepin-6-one 5-(L-valinyl)amino-7-cyclopropylmethyl-5,7-dihydro-6H-dibenz[b,d]azepin-6-one 5-(N-Boc-L-valinyl)amino-7-phenbutyl-5,7-dihydro-6H-dibenz[b,d]azepin6-one 5-(L-valinyl)amino-7-phenbutyl-5,7-dihydro-6H-dibenz[b,d]azepin-6-one 5-(N-Boc-L-valinyl)amino-7-hexyl-5,7-dihydro-6H-dibenz[b,d]azepin-6-one 5-(L-valinyl)amino-7-hexyl-5,7-dihydro-6H-dibenz[b,d]azepin-6-one 5-(N-Boc-L-valinyl)amino-9-fluoro-7-methyl-5,7-dihydro-6H-dibenz[b,d]azepin-6-one 5-(L-valinyl)amino-9-fluoro-7-methyl-5,7-dihydro-6H-dibenz[b,d]azepin-6-one 5-(N-Boc-L-valinyl)amino-10-fluoro-7-methyl-5,7-dihydro-6H-dibenz[b,d]azepin-6-one 5-(L-valinyl)amino-10-fluoro-7-methyl-5,7-dihydro-6H-dibenz[b,d]azepin-6-one 5-(N-Boc-L-valinyl)amino-13-fluoro-7-methyl-5,7-dihydro-6H-dibenz[b,d]azepin-6-one 5-(L-valinyl)amino-13-fluoro-7-methyl-5,7-dihydro-6H-dibenz[b,d]azepin-6-one 5-amino-9,13-difluoro-7-methyl-5,7-dihydro-6H-dibenz[b,d]azepin-6-one 5-amino-10,13-difluoro-7-methyl-5,7-dihydro-6H-dibenz[b,d]azepin-6-one 5-aminohexahydropyrido[a]benz[d]azepin-6-one 9-amino-5,6-Dihydro-4H-quino[8,1-ab][3]benzazepin-8(9H)-one 9-(N'-Boc-L-alaninyl)amino-5,6-Dihydro-4H-quino[8,1-ab][3]benzazepin-8(9H)-one 9-(N'-L-alaninyl)amino-5,6-dihydro-4H-quino[8,1-ab][3]benzazepin-8(9H)-one 7-amino-1,3,4,7,12,12a-hexahydropyrido[2,1-b][3]benzazepin-6(2H)-one 1-amino-4,5,6,7-tetrahydro-3,7-methano-3H-3-benzazepin-2(1H)-one 1-(N'-Boc-L-alaninyl)amino4,5,6,7-tetrahydro-3,7-methano-3H-3-benzazepin-2(1H)-one 1-(N'-L-alaninyl)amino4,5,6,7-tetrahydro-3,7-methano-3H-3-benzazepin-2(1H)-one or salts thereof.

\* \* \* \* \*